United States Patent
Schilling et al.

(10) Patent No.: US 7,304,086 B2
(45) Date of Patent: *Dec. 4, 2007

(54) INHIBITORS OF GLUTAMINYL CYCLASE

(75) Inventors: Stephan Schilling, Halle/Saale (DE); Mirko Buchholz, Halle/Saale (DE); Andre Johannes Niestroj, Sennewitz (DE); Ulrich Heiser, Halle/Saale (DE); Hans-Ulrich Demuth, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 20 days.

This patent is subject to a terminal disclaimer.

(21) Appl. No.: 11/051,760

(22) Filed: Feb. 4, 2005

(65) Prior Publication Data

US 2005/0215573 A1    Sep. 29, 2005

Related U.S. Application Data

(63) Continuation-in-part of application No. 10/838,993, filed on May 5, 2004.

(60) Provisional application No. 60/634,364, filed on Dec. 8, 2004, provisional application No. 60/542,133, filed on Feb. 5, 2004.

(51) Int. Cl.
*A61K 31/417* (2006.01)
*A61K 31/428* (2006.01)
*C07D 233/82* (2006.01)
*C07D 233/64* (2006.01)

(52) U.S. Cl. ........................ 514/400; 514/367; 548/161; 548/335.5; 548/338.5

(58) Field of Classification Search .............. 548/341.5
See application file for complete search history.

(56) References Cited

U.S. PATENT DOCUMENTS

| | | | | |
|---|---|---|---|---|
| 4,576,957 | A | * | 3/1986 | Marsico et al. ............. 514/383 |
| 5,552,426 | A | | 9/1996 | Lunn et al. .................. 514/394 |
| 5,955,548 | A | * | 9/1999 | Dorwald et al. ......... 525/329.4 |
| 6,448,282 | B1 | | 9/2002 | Phillips et al. .............. 514/400 |
| 6,979,686 | B1 | * | 12/2005 | Naraian et al. .......... 514/235.8 |
| 2005/0026844 | A1 | * | 2/2005 | Hammock et al. ............. 514/18 |

FOREIGN PATENT DOCUMENTS

| | | | |
|---|---|---|---|
| DE | 3210009 A1 | | 10/1982 |
| JP | 07068933 A2 | * | 3/1995 |
| WO | WO 93/01812 | | 2/1993 |
| WO | WO 93/20061 | | 10/1993 |
| WO | WO 95/22327 | | 8/1995 |
| WO | WO 97/43278 | | 11/1997 |
| WO | WO 9907672 A1 | * | 2/1999 |
| WO | WO 99/20599 | | 4/1999 |
| WO | WO 9924035 A1 | * | 5/1999 |
| WO | WO 99/41220 | | 8/1999 |
| WO | WO 99/41224 | | 8/1999 |
| WO | WO 99/64420 | | 12/1999 |
| WO | WO 00/53596 | | 9/2000 |
| WO | WO 01/34594 A1 | | 5/2001 |
| WO | WO 02/13821 | | 2/2002 |
| WO | WO 02/16318 A1 | | 2/2002 |
| WO | WO 02016318 A1 | * | 2/2002 |
| WO | WO 02/066459 A1 | | 8/2002 |
| WO | WO 02/092103 A1 | | 11/2002 |
| WO | WO 02094813 A1 | * | 11/2002 |
| WO | WO 03/040174 A2 | | 5/2003 |
| WO | WO 03/070732 | | 8/2003 |
| WO | WO 03068738 | * | 8/2003 |
| WO | WO 03095421 A1 | * | 11/2003 |
| WO | WO 2004026815 A2 | * | 4/2004 |
| WO | WO 2004/089366 | | 10/2004 |
| WO | WO 2004/098591 A2 | | 11/2004 |
| WO | WO 2004/098625 A2 | | 11/2004 |

OTHER PUBLICATIONS

Haley et al. Giorn. Ital. Chemioterap. (1962) 6-9 (No. 3), 213-24. *Abstract from CAS attached.*
Hough et al. Pharmacology, Biochemistry and Behavior 1999, 65(1), 61-66. *Abstract from CAS attached.*
Morissette et al. Advanced Drug Delivery Reviews 2004, 56, 275-300.*
Wright, et al.; "Thromboxane Synthetase Inhibitors and Antihypertensive Agents. 4.N-[(1H-Imidazol-1-yl)alkyl] Derivatives of Quinazoline-2,4(1H,3H)-diones, Quinazolin-4(3H)-ones, and 1,2,3-Benzotriazin-4(3H)-ones"; *J. Med. Chem.*; 1987, 30, 2277-2283.
Moon, et al.; "Cholinergic Activity of Acetylenic Imidazoles and Related Compounds"; *J. Med. Chem.*; 1991, 34, 2314-2327.
Venkatachalam, et al.; "Anti-HIV Activity of Aromatic and Heterocyclic Thiazolyl Thiourea Compounds"; *Bioorganic & Medicinal Chemistry Letters*; (2001) 11, 523-528.
Clader, et al.; "Substituted (1,2-Diarylethyl)amide Acyl-CoA:Cholesterol Acyltransferase Inhibitors: Effect of Polar Groups on in Vitro and in Vivo Activity"; *J. Med. Chem.*; 1995, 38, 1600-1607.
Wright, et al.; "Thromboxane Synthetase Inhibitors and Antihypertensive Agents. 1. N-[(1H-Imidazol-1-yl)alkyl]aryl Amides and N-[(1H-1,2,4-Triazol-1-yl)alkyl]aryl Amides"; *J. Med. Chem.*; 1986, 29, 523-530.

(Continued)

Primary Examiner—Kamal A. Saeed
Assistant Examiner—Jason M Nolan
(74) Attorney, Agent, or Firm—Sonnenschein Nath & Rosenthal LLP

(57) ABSTRACT

The present invention relates to novel inhibitors of glutaminyl cyclase and combinations thereof for the treatment of neuronal disorders, especially Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

38 Claims, No Drawings

OTHER PUBLICATIONS

Liu, et al.; "Nonpeptide Somatostatin Agonists with $sst_4$ Selectivity: Synthesis and Structure-Activity Relationships of Thioureas"; *J. Med. Chem.*; 1998, 41, 4693-4705.

Ganellin, et al.; "Design of Potent Non-Thiourea $H_3$-Receptor Histamine Antagonists"; *J. Med. Chem.*; 1995, 38, 3342-3350.

Misquitta, et al.; "Characterization of the Inhibition of Glutaminyl Cyclase by Imidazole Derivatives and Phenanthrolines" *Federation of American Societies for Experimental Biology. Annual Meeting*; 2002, vol. 16, No. 4, p. A157.

Misquitta, et al.; "Inhibition Studies of Glutaminyl Cyclase"; *FASEB Journal*; 2001, vol. 15, No. 5, p. A1159.

Schilling, et al.; "Glutaminyl cyclases unfold glutamyl cyclase activity under mild acid conditions"; *FEBS Letters*; 2004, 563: 191-196.

Muggia, et al.; "Phase I study of amifostine (A) as a cytoprotector of the gencitabine/cisplatin (GP) combination"; *European Journal of Cancer, Pergamon Press, Oxford, GB*; (2001); 37: S71.

Tsavaris, et al.; "Amifostine, in a Reduced Dose, Protects Against Severe Diarrhea Associated with Weekly Fluorouracil and Folinic Acid Chemotherapy in Advanced Colorectal Cancer: A Pilot Study"; *Journal of Pain and Symptom Management*; (2003); 26(3): 849-854.

Poplin, et al.; "Randomized clinical trial of mitomycin-C with or without pretreatment with WR-2721 in patients with advanced colorectal cancer"; *Cancer Chemotherapy and Pharmacology*; (1994); 33: 415-419.

Kurbacher and Mallmann; Chemoprotection in Anticancer Therapy: The Emerging Role of Amifostine (WR-2721); *Anticancer Research*; (1998); 18: 2203-2210.

Schilling, et al.; "Identification of Human Glutaminyl Cyclase as a Metalloenzyme"; *The Journal of Biological Chemistry*; (2003); 278(50): 49773-49779.

International Search Report for PCT/EP04/011630 dated Apr. 22, 2005.

International Search Report for PCT/EP2004/004778 dated Apr. 13, 2005.

Visser, et al.; "Task-specific ionic liquids for the extraction of metal ions from aqueous solutions"; *Chem. Commun.*; 2001; 1: 135-136.

Dressman, et al.; "Solid Phase Synthesis of Urea Libraries Using a Diversifiable Thiophenoxy Carbonyl Linker"; *Tetrahedron Letters, Elsevier Science Publishers*; 1998; 39(22): 3631-3634.

International Search Report for PCT/EP2005/001153 dated Aug. 3, 2005.

* cited by examiner

INHIBITORS OF GLUTAMINYL CYCLASE

RELATED APPLICATIONS

This application is a Continuation-in-part application of U.S. application Ser. No. 10/838,993, filed May 5, 2004 and claims the benefit of U.S. Provisional Application Ser. No. 60/542,133, filed Feb. 5, 2004 and U.S. Provisional Application Ser. No. 60/634,364, filed Dec. 8, 2004. The entire teachings of the above applications are incorporated herein by reference.

FIELD OF THE INVENTION

The invention relates to glutaminyl cyclase (QC, EC 2.3.2.5) that catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are useful as pesticides.

Definitions

Enzyme Inhibitors

Reversible enzyme inhibitors: comprise competitive inhibitors, non-competitive reversible inhibitors, slow-binding or tight-binding inhibitors, transition state analogs and multisubstrate analogs.

Competitive Inhibitors Show
  i) non-covalent interactions with the enzyme,
  ii) compete with substrate for the enzyme active site, The principal mechanism of action of a reversible enzyme inhibitor and the definition of the dissociation constant can be visualized as follows:

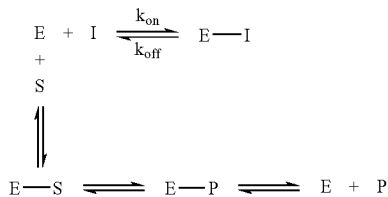

$$K_D = K_i = \frac{k_{off}}{k_{on}}$$

The formation of the enzyme-inhibitor [E–I] complex prevents binding of substrates, therefore the reaction cannot proceed to the normal physiological product, P. A larger inhibitor concentration [I] leads to larger [E–I], leaving less free enzyme to which the substrate can bind.

Non-Competitive Reversible Inhibitors
  i) bind at a site other than active site (allosteric binding site)
  ii) cause a conformational change in the enzyme which decreases or stops catalytic activity.

Slow-Binding or Tight-Binding Inhibitors
  i) are competitive inhibitors where the equilibrium between inhibitor and enzyme is reached slowly,
  ii) ($k_{on}$ is slow), possibly due to conformational changes that must occur in the enzyme or inhibitor
     a) are often transition state analogs
     b) are effective at concentrations similar to the enzyme conc. (subnanomolar $K_D$ values)
     c) due to $k_{off}$ values being so low these types of inhibitors are "almost" irreversible Transition State Analogs
are competitive inhibitors which mimic the transition state of an enzyme catalyzed reaction. Enzyme catalysis occurs due to a lowering of the energy of the transition state, therefore, transition state binding is favored over substrate binding.

Multisubstrate Analogs
For a reaction involving two or more substrates, a competitive inhibitor or transition state analog can be designed which contains structural characteristics resembling two or more of the substrates.

Irreversible enzyme inhibitors: drive the equilibrium between the unbound enzyme and inhibitor and enzyme inhibitor complex (E+I<--->E–I) all the way to the right with a covalent bond (~100 kcal/mole), making the inhibition irreversible.

Affinity Labeling Agents
Active-site directed irreversible inhibitors (competitive irreversible inhibitor) are recognized by the enzyme (reversible, specific binding) followed by covalent bond formation, and
  i) are structurally similar to substrate, transition state or product allowing for specific interaction between drug and target enzyme,
  ii) contain reactive functional group (e.g. a nucleophile, —COCH$_2$Br) allowing for covalent bond formation
  The reaction scheme below describes an active-site directed reagent with its target enzyme where $K_D$ is the dissociation constant and $k_{inactivation}$ is the rate of covalent bond formation.

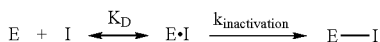

Mechanism-based enzyme inactivators (also called suicide inhibitors) are active-site directed reagents (unreactive) which binds to the enzyme active site where it is transformed to a reactive form (activated) by the enzyme's catalytic capabilities. Once activated, a covalent bond between the inhibitor and the enzyme is formed.

The reaction scheme below shows the mechanism of action of a mechanism based enzyme inactivator, where $K_D$ is the dissociation complex, $k_2$ is the rate of activation of the inhibitor once bound to the enzyme, $k_3$ is the rate of dissociation of the activated inhibitor, P, from the enzyme (product can still be reactive) from the enzyme and $k_4$ is the rate of covalent bond formation between the activated inhibitor and the enzyme.

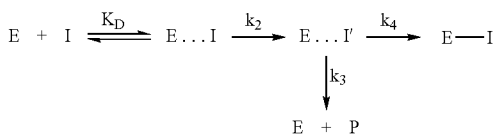

Inactivation (covalent bond formation, $k_4$) must occur prior to dissociation ($k_3$) otherwise the now reactive inhibitor is released into the environment. Partition ratio, $k_3/k_4$: ratio of released product to inactivation should be minimized for efficient inactivation of the system and minimal undesirable side reactions. A large partition ratio (favors dissocation) leads to nonspecific reactions.

Uncompetitive enzyme inhibitors: From the definition of uncompetitive inhibitor (an inhibitor which binds only to ES complexes) the following equilibria can be written:

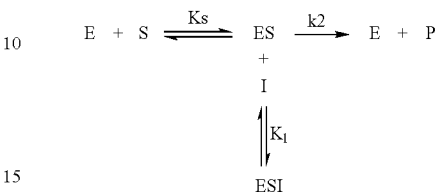

The ES complex dissociates the subtrate with a dissociation constant equal to Ks, whereas the ESI complex does not dissociate it (i.e has a Ks value equal to zero). The $K_m$'s of Michaelis-Menten type enzymes are expected to be reduced. Increasing substrate concentration leads to increasing ESI concentration (a complex incapable of progressing to reaction products), therefore the inhibition can not be removed.

Preferred according to the present invention are competitive enzyme inhibitors. Most preferred are competitive reversible enzyme inhibitors.

The terms "$k_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins were the proline is in amino acid position 3 or higher counted from the N-terminus of a peptide or protein substrate.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC.

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

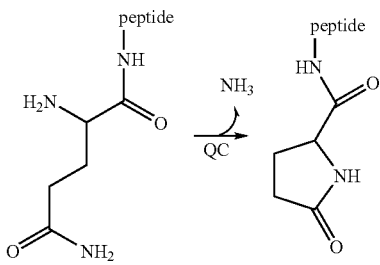

Scheme 2: Cyclization of L-homoglutamine by QC

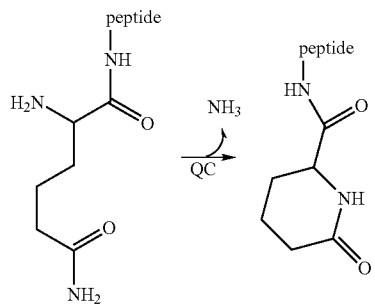

The term "EC" as used herein comprises the side activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

Scheme 3: N-terminal cyclization of uncharged glutamyl peptides by QC (EC)

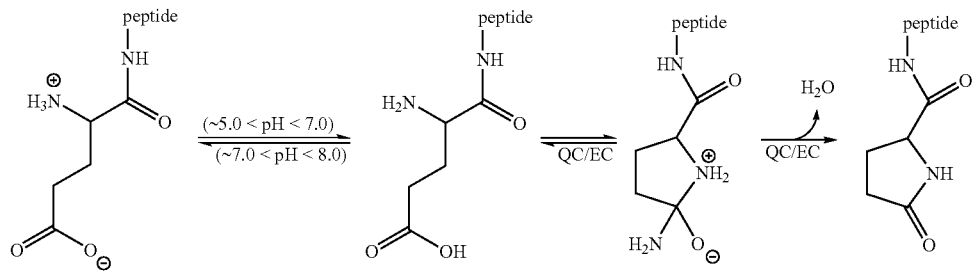

The term "QC-inhibitor" "glutaminyl cyclase inhibitor" is generally known to a person skilled in the art and means enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with a Ki for QC inhibition of 10 μM or less, more preferably of 1 μM or less, even more preferably of 0.1 μM or less or 0.01 μM or less, or most preferably 0.01 μM or less. Indeed, inhibitors with Ki values in the lower micromolar, preferably the nanomolar and even more preferably the picomolar range are contemplated. Thus, while the active agents are described herein, for convience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 1000 g/mole or less, 500 g/mole or less, preferably of 400 g/mole or less, and even more preferably of 350 g/mole or less and even of 300 g/mole or less.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: for example the term "pharmaceutically acceptable" embraces a veterinarily acceptable compound or a compound acceptable in human medicine and health care.

Throughout the description and the claims the expression "acyl", unless specifically limited, denotes a $C_{1-12}$ acyl residue, preferably a $C_{1-8}$ acyl residue and especially preferred a $C_{1-4}$ acyl residue. Examples of acyl include alkanoyl groups mentioned below and benzoyl.

"Peptides" are selected from dipeptides to decapeptides, preferred are dipeptides, tripeptides, tetrapeptides and pentapeptides. The amino acids for the formation of the "peptides" can be selected from those listed below.

Throughout the description and the claims the expression "alkyl", unless specifically limited, denotes a $C_{1-2}$ alkyl group, preferably a $C_{1-6}$ alkyl group. Alkyl groups may be straight chain or branched. Suitable alkyl groups include, for example, methyl, ethyl, propyl (e.g. n-propyl and isopropyl), (n-butyl, tert-butyl and sec-butyl), pentyl, hexyl, heptyl (e.g. n-heptyl) and octyl (e.g. n-octyl). The expression "alk", for example in the expression "alkoxy", and the expression "alkan", for example in the expression "alkanoyl", should be interpreted in accordance with the definition of "alkyl". Exemplary alkoxy groups include methoxy, ethoxy, butoxy (e.g. n-butoxy), heptyloxy (e.g. n-heptyloxy) and octyloxy (e.g. n-octyloxy). Exemplary alkanoyl (i.e. acyl groups) include ethanoyl (i.e. acetyl), propionyl and butyryl.

The expression "alkenyl", unless specifically limited, denotes a $C_{2-12}$ alkenyl group, preferably a $C_{2-6}$ alkenyl group, which contains at least one double bond at any desired location. Alkenyl groups may be straight chain or branched. Exemplary alkenyl groups include ethenyl, propenyl and butenyl.

The expression "alkynyl", unless specifically limited, denotes a $C_{2-12}$ alkynyl group, preferably a $C_{2-6}$ alkynyl group, which contains at least one triple bond at any desired location. Alkynyl groups may be straight chain or branched. Exemplary alkenyl groups include ethynyl, propynyl and butynyl.

The expression "cycloalkyl", unless specifically limited, denotes a $C_{3-12}$ cycloalkyl group, preferably a $C_{3-8}$ cycloalkyl group. Exemplary cycloalkyl groups include cylcopropyl, cyclobutyl, cyclopropyl, cyclohexyl, cycloheptyl and cyclooctyl. Cycloalkyl groups may be branched in which case the number of carbons indicates the total number of carbons in the moiety.

The expression "heterocyclic", unless specifically limited, denotes a cycloalkyl residue, wherein one or more (e.g. 1, 2 or 3) ring atoms are replaced by heteroatoms selected from N, S or O. Exemplary heterocyclic groups containing one hetero atom include pyrrolidine, tetrahydrofuran and piperidine. Such groups may be optionally substituted eg by alkyl, oxo or hydroxyl.

Concrete examples of a heterocyclic group comprise a substituted or unsubstituted oxirano, aziridino, oxacyclopropyl, azacyclopropyl, thiirano, oxetano, thietano, pyrrolidino, tetrahydrofurano, thiolano, 1,1-dioxo-thiolano, 1,3-dioxolano, thiazolidino, imidazolidino, oxazolidino, pyrazolidino, tetrahydropyrano, piperidino, urotropino, piperazino, N-methyl-piperazino, (2-(N-methyl)-N'-piperazinyl)-ethyl, (4N-(2'-hydroxyethyl)-1N-piperazinyl), (2-(4N-(2'-hydroxyethyl)-1N-piperazinyl)-ethyloxy), morpholino, 2-(N-morpholino)-ethyl group, as well as lactams, lactones, cyclic imides and cyclic anhydrides.

The expression "carbocylic", unless specifically limited, denotes a carbocylic group containing between 3 and 12 carbon atoms, more preferably between 3 and 8 carbon atoms. A carboyclic group, as used herein, refers to a group other than aryl or cycloalkyl which comprises at least one ring of carbon atoms without heteroatoms. Examples of carbocylic groups include bridged ring systems (e.g. bicyclo [2.2.1]heptenyl) and partially unsaturated ring systems.

The expression "aryl", unless specifically limited, denotes a $C_{6-12}$ aryl group, preferably a $C_{6-8}$ aryl group. Aryl groups will contain at least one aromatic ring (e.g. one, two or three rings), but may also comprise partially or fully unsaturated rings. An example of an aryl group with one aromatic ring is phenyl. Examples of aromatic groups with two aromatic rings include naphyl. Examples of aryl groups which contain partially or fully unsaturated rings include pentalene and indene. As noted below, aryl groups may optionally be substituted. Further examples for aryl groups are 4-fluoro-phenyl, 3-fluoro-phenyl, pentafluoro-phenyl, 4-hydroxyphenyl-, 3-nitro-phenyl-, 4-(trifluoromethyl)-phenyl-, 4-anilinyl-, 2-biphenylyl-, 3-biphenylyl-, 4-biphenylyl-, indenyl-, 1-naphthyl-, or 2-naphthyl-, 1-anthracenyl-, 2-anthracenyl-, 3-anthracenyl-groups.

Examples of -alkylaryl include phenylmethyl-(benzyl) and phenylethyl, 2-phenyleth-1-yl, p-tolyl-methyl-, p-tolyl-ethyl-, m-tolyl-methyl-, m-tolyl-ethyl-, o-tolyl-methyl-, o-tolyl-ethyl-, 2-(4-ethyl-phenyl)-eth-1-yl-, 2,3-dimethyl-phenyl-methyl-, 2,4-dimethyl-phenyl-methyl-, 2,5-dimethyl-phenyl-methyl-, 2,6-dimethyl-phenyl-methyl-, 3,4-dimethyl-phenyl-methyl-, 3,5-dimethyl-phenyl-methyl-, 2,4,6-trimethyl-phenyl-methyl-, 2,3-dimethyl-phenyl-ethyl-, 2,4-dimethyl-phenyl-ethyl-, 2,5-dimethyl-phenyl-ethyl-, 2,6-dimethyl-phenyl-ethyl-, 3,4-dimethyl-phenyl-ethyl-, 3,5-dimethyl-phenyl-ethyl-, 2,4,6-trimethyl-phenyl-ethyl-, benzhydryl(=diphenyl-methyl), benzhydryl(=diphenyl-ethyl), trityl(=triphenyl-methyl), trityl(=triphenyl-ethyl), α-styryl, β-styryl, cumyl, 2-ethyl-phenyl-methyl-, 3-ethyl-phenyl-methyl-, 4-ethyl-phenyl-methyl-, 2-ethyl-phenyl-ethyl-, 3-ethyl-phenyl-ethyl-, 4-ethyl-phenyl-ethyl-, 2-fluoro-benzyl, 1-methyl-2-fluoro-phen-6-yl-methyl-, 1-methyl-2-fluoro-phen-4-yl-methyl-, 1-methyl-2-fluoro-phen-6-yl-ethyl-, 1-methyl-2-fluoro-phen-4-yl-ethyl-, 1H-indenyl-methyl-, 2H-indenyl-methyl-, 1H-indenyl-ethyl-, 2H-indenyl-ethyl-, indanyl-methyl-, indan-1-on-2-yl-methyl-, indan-1-on-2-yl-ethyl-, tetralinyl-methyl-, tetralinyl-ethyl-, fluorenyl-methyl-, fluorenyl-ethyl-, (3-phenyl)-cyclopent-1-yl ?, dihydronaphthalinyl-methyl-, dihydronaphthalinyl-ethyl-, or (4-cyclohexyl)-phenyl-methyl-, (4-cyclohexyl)-phenyl-ethyl-.

The expression "heteroaryl", unless specifically limited, denotes as an aryl residue, wherein one or more (e.g. 1, 2, 3, or 4, preferably 1, 2 or 3) ring atoms are replaced by heteroatoms selected from N, S and O or else a 5-membered aromatic ring containing one or more (e.g. 1, 2, 3, or 4, preferably 1, 2 or 3) ring atoms selected from N, S and O. As noted below, heteroaryl groups may optionally be substituted. Exemplary heteroaryl groups include, pyridine (eg 2, 3 or 4-pyridine), pyrimidine, quinoline, pyrrole, furan, thiophene, oxazole, pyrazole, benzodioxolane, benzodioxane, benzothiophene, benzodioxepine, and thiazolyl, 1-imidazolyl, 2-imidazolyl, 4-imidazolyl, 3-phenyl-1-pyrrolyl, isoxazolyl, isothiazolyl, 3-pyrazolyl, 1,2,3-triazolyl, 1,2,4-triazolyl, tetrazolyl, pyridazinyl, pyrazinyl, indazolyl, 6-indolyl, benzimidazolyl, isochinolinyl, purinyl, carbazolinyl, acridinyl, and 2,3'-bifuryl groups.

Examples of -alkylheteroaryl include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridinomethyl-, 4-pyridino-ethyl-, 2-(thiazol-2-yl)-ethyl-, tetrahydroisochinolinyl-methyl-, tetrahydroisochinolinyl-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl, 4-methyl-pyrid in-3-ethyl.

The aforementioned aryl and heteroaryl groups may, where appropriate, optionally be substituted.

The expression "substitution" or "substituted" includes the substitution by one or more (e.g. 1, 2 or 3, preferably 1 or 2) monovalent or multivalent functional groups. Suitable substituent groups include alkyl, cycloalkyl, aryl (eg phenyl), heteroaryl (eg furyl), carbocylic, heterocyclic, alkoxy, cycloalkoxy, aryloxy, heteroaryloxy, carbocyclicoxy, hetercyclicoxy, alkenyloxy, alkynyloxy, alkenyl, alkynyl, acyl, alkanoyl, alkoxyalkanoyl, alkoxyalkyl, heteroarylalkyl, arylalkyl, arylalkyloxy, heteroarylalkyloxy, nitro, —S-alkyl (e.g. methylthio) halo (e.g. fluoro, chloro, bromo and iodo), cyano, hydroxyl, —$SO_2$alkyl, —$SO_2$aryl, —$SO_2$heteroaryl, —$SO_2$cycloalkyl —$SO_2$heterocyclic, —$CO_2$H, —$CO_2$alkyl, —NH2, —NHalkyl, —N(alkyl)$_2$ (e.g. dimethylamino), —CO—N(alkyl)$_2$ and —CO—NH(alkyl).

Alkyl groups including derivatives such as alkoxy together with alkenyl, alkynyl and cycloalkyl groups may optionally be halogen substituted e.g. substituted by fluoro. For example, halo substituted alkyl groups include trifluromethyl and halo substituted alkoxy groups include trifluoromethoxy.

The term "halogen" comprises fluorine (—F), chlorine (—Cl), bromine (—Br), and iodine (—I), respectively.

Amino acids which can be used in the present invention are L and D-amino acids, N-alkylated amino acids, N-methyl-amino acids, aza-amino acids; allo- and threo-forms of Ile and Thr, which can, e.g. be α-, β- or ω-amino acids, whereof α-amino acids are preferred.

Examples of amino acids are:

aspartic acid (Asp), glutamic acid (Glu), arginine (Arg), lysine (Lys), histidine (His), glycine (Gly), serine (Ser), cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-aminooctanoic acid (Aoa), acetidine-(2)-carboxylic acid (Ace), pipecolic acid (Pip), 3-aminopropionic acid, 4-aminobutyric acid and so forth, alpha-aminoisobutyric acid (Aib), sarcosine (Sar), ornithine (Orn), citrulline (Cit), homoarginine (Har), t-butylalanine (t-butyl-Ala), t-butylglycine (t-butyl-Gly), N-methylisoleucine (N-MeIle), phenylglycine (Phg), cyclohexylalanine (Cha), norleucine (Nle), cysteic acid (Cya) and methionine sulfoxide (MSO), acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic acids. Examples of ω̄-amino acids are e.g.: 5-Ara (aminoraleric acid), 6-Ahx (aminohexanoic acid), 8-Aoc (aminooctanoic aicd), 9-Anc (aminovanoic aicd), 10-Adc (aminodecanoic acid), 11-Aun (aminoundecanoic acid), 12-Ado (aminododecanoic acid). Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal) and (2-Nal), 4-aminophenylalanine (Phe(4-NH$_2$)), 4-benzoylphenylalanine (Bpa), diphenylalanine (Dip), 4-bromophenylalanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe (3,4-Cl$_2$)), 3-fluorophenylalanine (Phe(3-F)), 4-fluorophenylalanine (Phe(4-F)), 3,4-fluorophenylalanine (Phe(3,4-F$_2$)), pentafluorophenylalanine (Phe(F$_5$)), 4-guanidinophenylalanine (Phe(4-guanidino)), homophenylalanine (hPhe), 3-jodophenylalanine (Phe(3-J)), 4-jodophenylalanine (Phe(4-J)), 4-methylphenylalanine (Phe(4-Me)), 4-nitrophenylalanine (Phe-4-NO$_2$)), biphenylalanine (Bip), 4-phosphonomethylphenylalanine (Pmp), cyclohexylglycine (Ghg), 3-pyridinylalanine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4, -tetrahydroisoquinolin-3-carboxylic acid (Tic), propargylglycine (Pra), 6-hydroxynorleucine (NU(6-OH)), homotyrosine (hTyr), 3-jodotyrosine (Tyr(3-J)), 3,5-dijodotyrosine (Tyr(3,5-J$_2$)), methyltyrosine (Tyr(Me)), 2',6'-dimethyltyrosine (Dmt), 3-NO$_2$-tyrosine (Tyr(3-NO$_2$)), phosphotyrosine (Tyr(PO$_3$H$_2$)), alkylglycine, 1-aminoindane-1-carboxylic acid, 2-aminoindane-2-carboxylic acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly(NH$_2$)), diaminobutyric acid (Dab), 1,3-dihydro-2H-isoinole-carboxylic acid (Disc), homocylcohexylalanine (hCha), homophenylalanine (hPhe or Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienryl)-alanine (Tha).

"Peptides" are selected from dipeptides to decapeptides, preferred are dipeptides, tripeptides, tetrapeptides and pentapeptides. The amino acids for the formation of the "peptides" can be selected from those listed above.

An "aza-amino acid" is defined as an amino acid where the chiral α-CH group is replaced by a nitrogen atom, whereas an "aza-peptide" is defined as a peptide, in which the chiral α-CH group of one or more amino acid residues in the peptide chain is replaced by a nitrogen atom.

Other amino acid substitutions for those encoded in the genetic code can also be included in peptide compounds within the scope of the invention and can be classified within this general scheme. Proteinogenic amino acids are defined as natural protein-derived α-amino acids. Non-proteinogenic amino acids are defined as all other amino acids, which are not building blocks of common natural proteins.

"Peptide mimetics" per se are known to a person skilled in the art. They are preferably defined as compounds which have a secondary structure like a peptide and optionally further structural characteristics; their mode of action is largely similar or identical to the mode of action of the native peptide; however, their activity (e.g. as an antagonist or inhibitor) can be modified as compared with the native peptide, especially vis à vis receptors or enzymes. Moreover, they can imitate the effect of the native peptide (agonist). Examples of peptide mimetics are scaffold mimetics, non-peptidic mimetics, peptoides, peptide nucleic acids, oligopyrrolinones, vinylogpeptides and oligocarbamates. For the definitions of these peptide mimetics see Lexikon der Chemie, Spektrum Akademischer Verlag Heidelberg, Berlin, 1999.

The aim for using these mimetic structures is increasing the activity, increasing the selectivity to decrease side effects, protect the compound against enzymatic degradation for prolongation of the effect.

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt or solvate is also intended, provided such is possible or appropriate under the circumstances.

Salts and solvates of the compounds of formula (1) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulphuric, nitric, citric, tartaric, phosphoric, lactic, pyruvic, acetic, trifluoroacetic, triphenylacetic, sulphamic, sulphanilic, succinic, oxalic, fumaric, maleic, malic, mandelic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Examples of solvates include hydrates.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

Peptide Sequences

The peptides mentioned and used herein have the following sequences:

Aβ(1-42):
Asp-Ala-Glu-Phe-Arg-His-Asp-Ser-Gly-Tyr-Glu-Val-
His-His-Gln-Lys-Leu-Val-Phe-Phe-Ala-Glu-Asp-Val-
Gly-Ser-Asn-Lys-Gly-Ala-Ile-Ile-Gly-Leu-Met-Val-
Gly-Gly-Val-Val-Ile-Ala

Aβ(1-40):
Asp-Ala-Glu-Phe-Arg-His-Asp-Ser-Gly-Tyr-Glu-Val-
His-His-Gln-Lys-Leu-Val-Phe-Phe-Ala-Glu-Asp-Val-
Gly-Ser-Asn-Lys-Gly-Ala-Ile-Ile-Gly-Leu-Met-Val-
Gly-Gly-Val-Val

Aβ(3-42):
Glu-Phe-Arg-His-Asp-Ser-Gly-Tyr-Glu-Val-His-His-
Gln-Lys-Leu-Val-Phe-Phe-Ala-Glu-Asp-Val-Gly-Ser-
Asn-Lys-Gly-Ala-Ile-Ile-Gly-Leu-Met-Val-Gly-Gly-
Val-Val-Ile-Ala

Aβ(3-40):
Glu-Phe-Arg-His-Asp-Ser-Gly-Tyr-Glu-Val-His-His-
Gln-Lys-Leu-Val-Phe-Phe-Ala-Glu-Asp-Val-Gly-Ser-
Asn-Lys-Gly-Ala-Ile-Ile-Gly-Leu-Met-Val-Gly-Gly-
Val-Val

Aβ(1-11)a:
Asp-Ala-Glu-Phe-Arg-His-Asp-Ser-Gly-Tyr-Glu-NH$_2$

Aβ(3-11)a:
Glu-Phe-Arg-His-Asp-Ser-Gly-Tyr-Glu-NH$_2$

Aβ(1-21)a:
Asp-Ala-Glu-Phe-Arg-His-Asp-Ser-Gly-Tyr-Glu-Val-
His-His-Gln-Lys-Leu-Val-Phe-Phe-Ala-NH$_2$

Aβ(3-21)a:
Glu-Phe-Arg-His-Asp-Ser-Gly-Tyr-Glu-Val-His-His-
Gln-Lys-Leu-Val-Phe-Phe-Ala-NH$_2$

Gln$^3$-Aβ(3-40):
Gln-Phe-Arg-His-Asp-Ser-Gly-Tyr-Glu-Val-His-His-
Gln-Lys-Leu-Val-Phe-Phe-Ala-Glu-Asp-Val-Gly-Ser-
Asn-Lys-Gly-Ala-Ile-Ile-Gly-Leu-Met-Val-Gly-Gly-
Val-Val

Gln$^3$-Aβ(3-21)a:
Gln-Phe-Arg-His-Asp-Ser-Gly-Tyr-Glu-Val-His-His-
Gln-Lys-Leu-Val-Phe-Phe-Ala-NH$_2$

Gln$^3$-Aβ(1-11)a:
Asp-Ala-Gln-Phe-Arg-His-Asp-Ser-Gly-Tyr-Glu-NH$_2$

-continued

Gln$^3$-Aβ(3-11)a:
Gln-Phe-Arg-His-Asp-Ser-Gly-Tyr-Glu-NH$_2$

SUMMARY OF THE INVENTION

The present invention provides compounds that act as inhibitors of glutaminyl cyclase (QC, EC 2.3.2.5).

Physiological substrates of QC in mammals are, e.g. [Glu$^3$] amyloid β-protein (3-40/42), [Gln$^3$] amyloid β-protein (3-40/42), Gastrin, Neurotensin, FPP, CCL 2, CCL 7, CCL 8, CCL 16, CCL 18, Fractalkine, Orexin A, [Gln$^3$]-glucagon(3-29) and [Gln$^5$]-substance P(5-11). The compounds according to the present invention and pharmaceutical compositions comprising at least one compound according to the present invention are useful for the treatment of conditions that can be treated by modulation of QC activity.

By administering inhibitors of QC (EC) activity to a mammal it is possible to prevent or alleviate or treat neuronal disorders (Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia).

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a preferred embodiment, the present invention provides the use of inhibitors of QC (EC) activity in combination with other agents, especially for the treatment of neuronal disorders.

DETAILED DESCRIPTION OF THE INVENTION

The present invention provides novel inhibitors of QC (EC) of the formula 1,

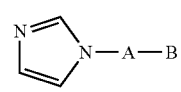

formula 1 wherein:
A is either:
    an alkyl chain, alkenyl chain or alkynyl chain;
or A is a group selected from:

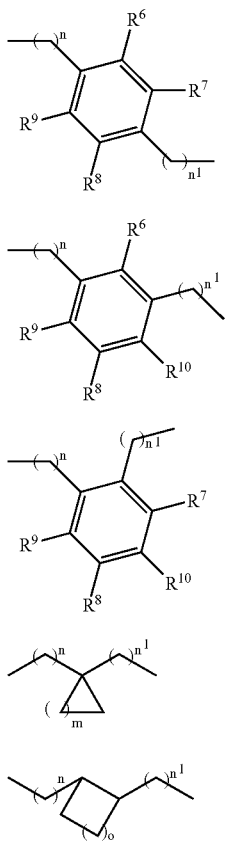

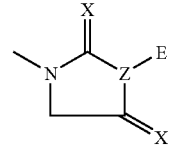
(I)

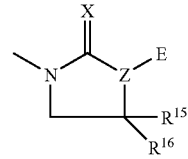
(II)

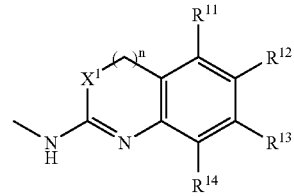
(III)

(IV)

(V)

wherein:
$R^6$, $R^7$, $R^8$, $R^9$ and $R^{10}$ are independently H or an alkyl chain, alkenyl chain, alkynyl chain, cycloalkyl, a carbocycle, aryl, heteroaryl, or a heterocycle;

n and $n^1$ are independently 1-5;

m is 1-5;

o is 0-4;

and B is a group selected from (VI)-(XIV):

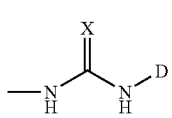
(VI)

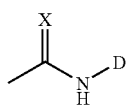
(VIa)

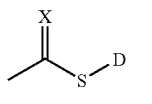
(VIb)

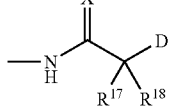
(VII)

-continued

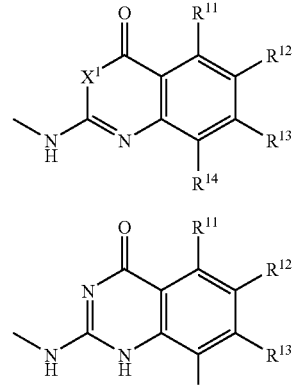
(VIII)

(IX)

(X)

(XI)

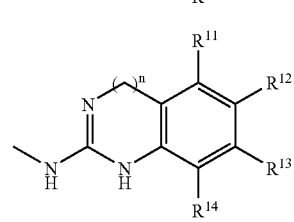
(XII)

(XIII)

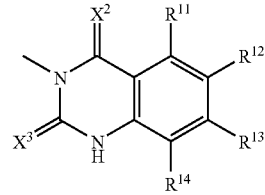
(XIV)

wherein:

D and E independently represent an alkyl chain, alkenyl chain, alkynyl chain, a cycloalkyl, carbocycle, aryl, -alkylaryl, heteroaryl, -alkylheteroaryl, acyl or a heterocycle.

X represents $CR^{20}R^{21}$, O, S, $NR^{19}$, with the proviso for formulas (VIII) and (IX) that, if Z=CH, X is O or S;

$R^{19}$ is selected from the group consisting of H, alkyl, cycloalkyl, aryl, heteroaryl, -oxyalkyl, -oxyaryl, carbonyl, amido, hydroxy, $NO_2$, $NH_2$, CN;

$R^{20}$ and $R^{21}$ are independently selected from H, alkyl, cycloalkyl, heterocycle, aryl, heteroaryl, -oxyalkyl, -oxyaryl, carbonyl, amido, $NO_2$, $NH_2$, CN, $CF_3$;

$X^1$, $X^2$ and $X^3$ are independently O or S provided that $X^2$ and $X^3$ are not both O;

Y is O or S, with the proviso that Y may not be O, when the carbocycle formed by $R^{17}$ and $R^{18}$ has 3 members in the ring;

Z is CH or N;

$R^{11}$, $R^{12}$, $R^{13}$ and $R^{14}$ can be independently selected from H, an alkyl chain, an alkenyl chain, an alkynyl chain, cycloalkyl, carbocycle, aryl, heteroaryl, a heterocycle, halogen, alkoxy-, -thioalkyl, carboxyl, carboxylic acid ester, carbonyl, carbamide, carbimide, thiocarbamide or thiocarbonyl, $NH_2$, $NO_2$;

$R^{15}$ and $R^{16}$ are independently of each other H or a branched or unbranched alkyl chain, or a branched or unbranched alkenyl chain;

$R^{17}$ and $R^{18}$ are independently selected from H or an alkyl chain, alkenyl chain, a alkynyl chain, a carbocycle, aryl, heteroaryl, heteroalkyl or can be connected to form a carbocycle with up to 6 ring atoms;

n is 0 or 1;

with the proviso that the following compounds:

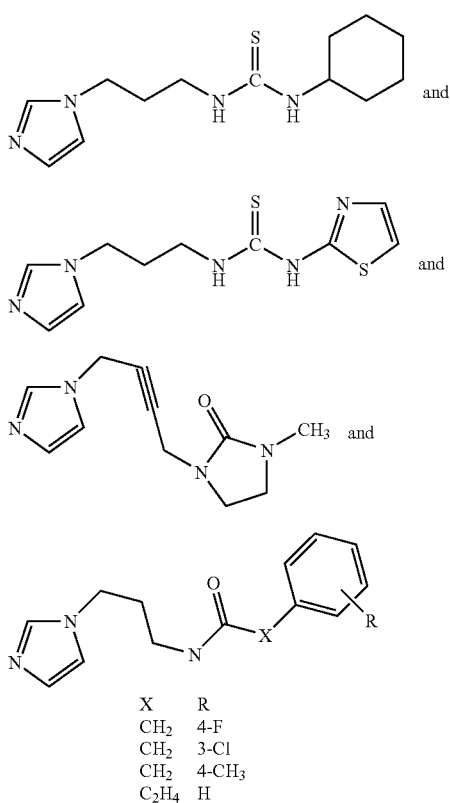

are excluded from formula 1.

When A is selected from an alkyl chain, alkenyl chain or alkynyl chain, preferably A is a $C_1$-$C_7$ alkyl chain, $C_1$-$C_7$ alkenyl chain or a $C_1$-$C_7$ alkynyl chain. In one embodiment of the invention A is an unbranched $C_{2-5}$ alkyl chain, in particular an unbranched $C_{3-4}$ alkyl chain, especially an unbranched $C_3$ alkyl chain. In a second embodiment of the invention A represents a $C_3$ alkyl chain which is substituted at the 2 position by one (i.e. in S or R configuration) or two methyl groups.

When A is selected from the formulae (I) to (V), preferably A is selected from groups (I) to (IV). In one embodiment of the invention A represents a group of formula (IV), wherein $n^1$ are each equal to 1 and m=1-4, especially m=1. In a second embodiment of the invention A represents a group of formula (I), (II) or (III), wherein n and $n^1$ are each equal to 1 and $R^6$, $R^7$, $R^8$, $R^9$ and $R^{10}$ represent H.

Preferably $R^6$, $R^7$, $R^8$, $R^9$ and $R^{10}$ represent H or methyl.

In one embodiment of the invention the group B is chosen from (VI), (VIa), (VIb), (VII), (X), (XI), (XII), (XIII) and (XIV). In a second embodiment of the invention group B represents formula (VI). In a third embodiment of the invention group B represents formula (VIa). In a fourth embodiment of the invention group B represents formula (VIb). In a fifth embodiment of the invention group B represents formula (VII). In a sixth embodiment of the invention group B represents formula (X). In a seventh embodiment of the invention group B represents formula (XI). In an eighth embodiment of the invention group B represents formula (XII). In another embodiment of the invention group B represents formula (XIII). In a further embodiment of the invention group B represents formula (XIV). In a preferred embodiment of the invention B represents a group of formula (VI) or (VII).

When B represents a group (IX) suitably A does not represent alkynyl.

Preferably D and E independently represent benzyl, aryl, heteroaryl or a heterocycle.

In one embodiment of the invention D and E represent aryl, in particular phenyl or napthyl, especially substituted phenyl. Preferred substituent groups when D represents phenyl include alkoxy-, -thioalkyl, halogen, or a carboxylic acid alkyl or aryl ester. Also preferred are fluoro, chloro, bromo, iodo, trifluoromethyl, trifluoromethoxy, methoxy, ethoxy, benzyloxy, cyano, acetyl, dimethyl amino, methylsulphanyl, nitro, oxazolyl, pyrazolyl, isopropyl, ethyl and methoxycarbonyl. Where a phenyl group is mono-substituted it is preferred that substitution is in the 4-position. Other suitable aryl groups which D and E may represent include dihydrobenzodioxine, benzodioxole, benzodithiole dihydrobenzodithiine, benzooxathiole and dihydrobenzooxathiine. A particularly preferred group which D or E may represent is 3,4-(dimethoxy)-phenyl, Preferably $R^{20}$ and $R^{21}$ represent $NO_2$, CN, $CF_3$ or, if $R^{20}$ is H, $R^{21}$ is $NO_2$, CN, $CF_3$, or, if $R^{21}$ is H, $R^{20}$ is $NO_2$, CN, $CF_3$.

In one embodiment, X or Y is S, O or $NR^1$. Preferably X or Y is S.

Preferably Z represents N.

In a preferred embodiment, $R^{11}$ and $R^{14}$ are H.

In a further preferred embodiment, $R^{12}$ and $R^{13}$ are independently selected from oxyalkyl or thioalkyl, halogen, or carboxylic acid alkyl ester or phenyl.

In a preferred embodiment, at least one of $R^{15}$ and $R^{16}$ is H, more preferably, $R^{15}$ and $R^{16}$ are both H.

In a preferred embodiment, one of $R^{17}$ and $R^{18}$ is H and the other is Me. Also preferred are compounds wherein one of $R^{17}$ and $R^{18}$ is H and the other is phenyl. Additionally preferred are compounds where $R^{17}$ and $R^{18}$ form a carbocycle with up to 6 members in the ring atoms.

Preferred compounds include those defined by Examples 13, 119 and 125 below.

The present invention provides compounds of formula 1 for use as a pharmaceutical. with the proviso that the compounds:

(a)
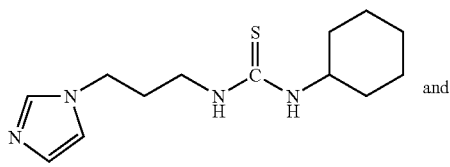
and (b)
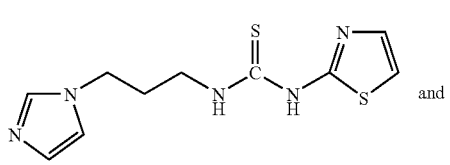
and (c)
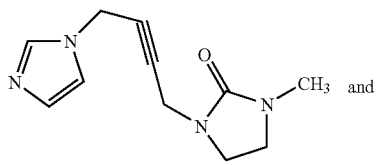
and (d)
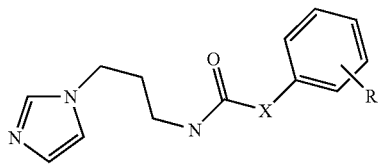

| X | R |
|---|---|
| CH$_2$ | 4-F |
| CH$_2$ | 3-Cl |
| CH$_2$ | 4-CH$_3$ |
| C$_2$H$_4$ | H | are excluded from formula 1.

The compound (a) of the proviso above is disclosed as compound 7 in Ganellin et al (1995) J Med Chem 38(17) 3342-3350. This paper discloses said compound as a weak inhibitor of the histamine H3 receptor.

The compound of proviso (b) is disclosed as compound 7 in Venkatachalam et al (2001) Bioorganic Med Chem Lett 11, 523-528. This discloses said compound as an HIV1 reverse transcriptase inhibitor.

The compound of proviso (c) is disclosed as compound 19b in Moon et al (1991) J Med Chem 34, 2314-2327. This paper discloses said compound as a cholinergic agonist with potential use in the treatment of Alzheimer's disease.

The compounds of proviso (d) are disclosed as compounds 99, 100 and 102-103 in Wright et al (1986) J Med Chem 29, 523-530. This paper discloses said compounds as thromoxane synthetase inhibitors.

Certain compounds which would be embraced by formula 1 if it were not for the proviso "provided that X$^2$ and X$^3$ are not both O" are disclosed in Wright et al (1987) J Med Chem 30, 2277-2283 as thromboxane synthetase inhibitors.

Certain compounds which would be embraced by formula 1 if it were not for the proviso "that Y may not be O, when the carbocycle formed by R$^{17}$ and R$^{18}$ has 3 members in the ring" are disclosed in EP 0 117 462 A2 as thromboxane synthetase inhibitors.

Furthermore, the present invention provides the use of inhibitors of QC of the formula 1, without the proviso excluding compounds (a)-(d) or the proviso that X$^2$ and X$^3$ are not both O or the proviso that Y may not be O, when the carbocycle formed by R$^{17}$ and R$^{18}$ has 3 members in the ring, for the preparation of a medicament for the treatment of diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

The present invention also provides inhibitors of QC of the formula 1, without the proviso excluding compounds (a)-(d) or the proviso that X$^2$ and X$^3$ are not both O or the proviso that Y may not be O, when the carbocycle formed by R$^{17}$ and R$^{18}$ has 3 members in the ring, for use in the treatment of diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

The present invention also provides a method of treatment for a disease selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia, comprising the administration of a therapeutically active amount of at least one compound of formula 1, without the proviso excluding compounds (a)-(d) or the proviso that X$^2$ and X$^3$ are not both O or the proviso that Y may not be O, when the carbocycle formed by R$^{17}$ and R$^{18}$ has 3 members in the ring, to a mammal, preferably a human.

Most preferably, the present invention provides a method of treatment and corresponding uses for a disease. selected from the group consisting of Alzheimer's disease, Down Syndrome, Parkinson disease and Chorea Huntington, comprising the administration of a therapeutically active amount of at least one compound of formula 1, without the proviso excluding compounds (a)-(d), to a mammal, preferably a human.

Suitably in the above mentioned methods and uses the compound is not the compound of proviso (c).

A further compound, that of formula 1* shown below, is also a novel inhbitor of QC:

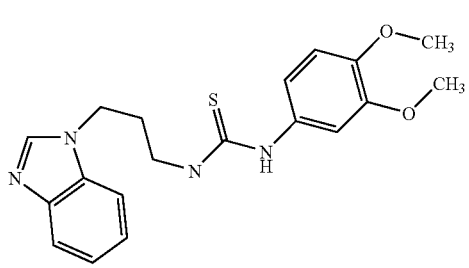

formula 1*

The compound of formula 1* may be employed in the methods and uses according to the invention in an analogous manner to the compounds of formula 1 described above.

In a further embodiment, the present invention provides novel inhibitors fo QC (EC) of the formula 1a,

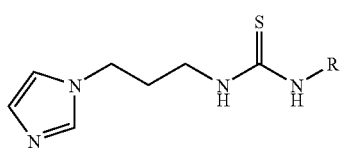

(1a)

wherein R is defined in examples 1 to 53.

| Example | R | ESI-MS (M + H) | Res. Act. (%) | IC$_{50}$ (μM) | K$_i$ (μM) |
|---|---|---|---|---|---|
| 1 | Methyl | 199.3 | 4.3 | | 13 |
| 2 | tert-Butyl | 241.4 | 60.7 | | 14.7 |
| 3 | Benzyl | 275.4 | 60.9 | | 5.67 |
| 4 | Phenyl | 261.4 | 42.3 | | 4.4 |
| 5 | 4-(fluoro)-phenyl | 279.35 | 42.0 | | 4.73 |
| 6 | 4-(chloro)-phenyl | 295.80 | | | 1.2 |
| 7 | 4-(ethyl)-phenyl | 289.41 | 28.7 | | 2.78 |
| 8 | 4-(trifluoromethyl)-phenyl | 329.4 | 38.5 | | 3.93 |
| 9 | 4-(methoxy-carbonyl)-Phenyl | 319.4 | | | 1.19 |
| 10 | 4-(acetyl)-phenyl | 303.4 | 17.0 | | 1.70 |
| 11 | 4-(methoxy)-phenyl | 291.4 | 9.7 | | 0.70 |
| 12 | bicyclo[2.2.1]hept-5-en-2-yl | 277.5 | 16.0 | | |
| 13 | 3,4-(dimethoxy)-phenyl | 321.5 | 0.7 | 0.22 | 0.06 |
| 14 | 2,4-(dimethoxy)-phenyl | 321.5 | 2.2 | | 0.57 |
| 15 | 3,5-(dimethoxy)-phenyl | 321.5 | 2.86 | | 0.75 |
| 16 | 2-(methoxy-carbonyl)-Phenyl | 319.4 | | | |
| 17 | 4-(oxazol-5-y)-phenyl | 328.5 | 3.64 | | 0.86 |
| 18 | 4-(pyrazol-1-yl)-phenyl | 327.4 | | | |
| 19 | 4-(isopropyl)-phenyl | 303.5 | 8.7 | | |
| 20 | 4-(piperidine-1-sulfonyl)-Phenyl | 408.6 | 8.5 | | 2.27 |
| 21 | 4-(morpholin-4-yl)-phenyl | 346.5 | 9.0 | | |
| 22 | 4-(cyano)-phenyl | 286.4 | 9.0 | | 2.89 |
| 23 | 2,3-dihydro-benzo[1,4]dioxin-6-yl | 319.4 | 4.17 | | 1.12 |
| 24 | benzo[1,3]dioxol-5-yl | 305.4 | 16.7 | | 5.66 |
| 25 | 3,4,5(trimethoxy)-phenyl | 351.5 | 1.7 | | 0.34 |
| 26 | 3-(methoxy)-phenyl | 291.4 | 6.8 | | 1.86 |
| 27 | 4-(ethoxy)-phenyl | 305.5 | 7.2 | | 0.89 |
| 28 | 4-(benzyloxy)-phenyl | 367.5 | | | 0.98 |
| 29 | 4-(methoxy)-benzyl | 305.5 | | | 3.93 |
| 30 | 3,4-(dimethoxy)-benzyl | 335.5 | | | 1.55 |
| 31 | 2-(methoxy-carbonyl)-thiophene-3-yl | 325.5 | | | |
| 32 | 3-(ethoxy-carbonyl)-4,5,6,7-tetrahydrobenzo[b]thiophene2-yl | 392.6 | | | |
| 33 | 2-(methoxy-carbonyl)-4-(methyl)-thiophene-3-yl | 339.5 | | | |
| 34 | Benzo[c][1,2,5]thiazol-4-yl | 319.5 | | | |
| 35 | Benzo[c][1,2,5]thiazol-5-yl | 319.5 | 4.4 | | 1.37 |
| 36 | 5-(methyl)-3-(phenyl)-isooxazol-4-yl | 342.5 | | | |
| 37 | 3,5-(dimethyl)-isooxazol-4-yl | 280.4 | | | |
| 38 | 4-(iodo)-phenyl | 387.3 | 23.5 | | 2.12 |
| 39 | 4-(bromo)-phenyl | 340.3 | | | 2.52 |
| 40 | 4-(methyl)-phenyl | 275.4 | 31.3 | | 2.14 |
| 41 | Naphthalen-1-yl | 311.5 | 26.7 | | 2.79 |
| 42 | 4-(nitro)-phenyl | 306.4 | 31.1 | | 2.68 |
| 43 | Butyl | 241.4 | 53.8 | 14.0 | |
| 44 | Cyclooctyl | 295.5 | 33.1 | 9.1 | |
| 45 | Furan-2-ylmethyl | 265.4 | 61.4 | 10.0 | |
| 46 | Tetrahydrofuran-2-ylmethyl | 269.4 | 46.0 | 12.8 | |
| 47 | Benzo[1,3]dioxol-5-ylmethyl | 319.4 | 42.7 | | 6.1 |
| 48 | 2-(morpholin-4-yl)-ethyl | 298.5 | 55.0 | 13.3 | |
| 49 | 4-(methylsulfanyl)-phenyl | 307.5 | 19.1 | | 1.66 |
| 50 | 4-(dimethylamino)-phenyl | 304.5 | | | 2.03 |
| 51 | 4-(trifluoromethoxy)-phenyl | 345.4 | 14.2 | | |
| 52 | Benzoyl | 288.3 | | | |
| 53 | Pyridin-4-yl | 261.1 | | | |

In a further embodiment, the present invention provides novel inhibitors of QC (EC) of the formula 1b,

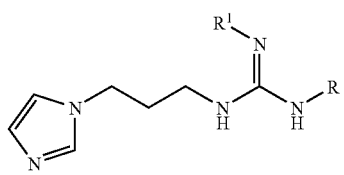

(1b)

wherein R$^1$ and R$^2$ are defined in examples 54 to 95.

| Example | R¹ | R² | ESI-MS (M + H) | Res. Act. (%) | $K_i$ (μM) |
|---|---|---|---|---|---|
| 54 | Cyano | Methyl | 207.3 | | 1.5 |
| 55 | Cyano | 3,4-(dimethoxy)-phenyl | 329.4 | | 1.36 |
| 56 | Cyano | 2,4-(dimethoxy)-phenyl | 329.4 | | |
| 57 | Cyano | 3,5-(dimethoxy)-phenyl | 329.4 | | 0.91 |
| 58 | Cyano | 2,3-dihydrobenzo[b][1,4]dioxin-7-yl | 327.4 | | 0.64 |
| 59 | Cyano | Benzo[d][1,3]dioxol-6-yl | 313.4 | | 0.73 |
| 60 | Cyano | 3,4,5-(trimethoxy)-phenyl | 359.4 | | 0.88 |
| 61 | Cyano | 3-(methoxy)-phenyl | 299.4 | | |
| 62 | Cyano | 4-(ethoxy)-phenyl | 313.4 | | |
| 63 | Cyano | 4-(benzyloxy)-phenyl | 375.5 | | |
| 64 | Cyano | Phenyl | 269.4 | | 1.02 |
| 65 | Cyano | 4-(methoxy)-phenyl | 299.4 | | 0.70 |
| 66 | Cyano | 4-(acetyl)-phenyl | 311.4 | | |
| 67 | Cyano | 4-(nitro)-phenyl | 314.4 | | |
| 68 | Cyano | Benzyl | 283.4 | 22.5 | 8.17 |
| 69 | Cyano | Naphthalen-1-yl | 319.4 | | |
| 70 | Cyano | 4-(fluoro)-phenyl | 387.3 | | |
| 71 | Cyano | 4-(iodo)-phenyl | 395.3 | | |
| 72 | Cyano | 4-(bromo)-phenyl | 348.3 | | |
| 73 | Cyano | Cyclooctyl | 289.4 | | |
| 74 | Cyano | tert-butyl | 249.3 | | |
| 75 | Cyano | 4-(methyl)-phenyl | 283.3 | | 1.34 |
| 76 | Cyano | 4-(methylthio)-phenyl | 315.5 | | |
| 77 | Cyano | 4-(ethyl)-phenyl | 297.4 | | |
| 78 | Cyano | 4-(dimethylamino)-phenyl | 312.4 | | |
| 79 | Cyano | Butyl | 249.4 | | |
| 80 | Cyano | Trityl | 435.6 | | |
| 81 | Cyano | (Benzo[d][1,3]dioxol-6yl)methyl | 327.4 | | 1.53 |
| 82 | Cyano | (tetrahydrofuran-2yl)methyl | 277.4 | | |
| 83 | Cyano | 4-(trifluoromethyl)-phenyl | 334.4 | | |
| 84 | Cyano | (furan-2-yl)methyl | 273.4 | | |
| 85 | Cyano | 2-(morpholin-4-yl)-ethyl | 306.4 | | |
| 86 | Cyano | 4-(oxazol-5yl)-phenyl | 336.4 | | |
| 87 | Cyano | Pyridin-3-yl | 270.4 | | |
| 88 | Cyano | 4-(cyano)-phenyl | 294.4 | | |
| 89 | Cyano | 4-(trifluoromethoxy)-phenyl | 353.4 | | |
| 90 | Cyano | 4-(piperidinosulfonyl)-phenyl | 416.6 | | |
| 91 | Cyano | 4-(1H-pyrazol-1-yl)phenyl | 335.4 | | |
| 92 | H | 3,4-(dimethoxy)-phenyl | 304.4 | | 204.5 |
| 93 | Methyl | 3,4-(dimethoxy)-phenyl | 318.4 | | 3.62 |
| 94 | Cyano | 2,3,4-(trimethoxy)-phenyl | 358.1 | | |
| 95 | Cyano | Cycloheptyl | 288.2 | | |

In a further embodiment, the present invention provides novel inhibitors of QC (EC) formula 1c,

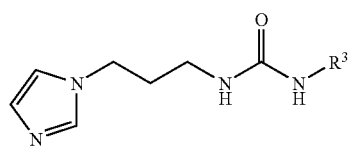

(1c)

wherein R³ is defined in examples 96 to 102.

| Example | R³ | ESI-MS (M + H) | Res. Act. (%) | IC₅₀ (μM) | $K_i$ (μM) |
|---|---|---|---|---|---|
| 96 | Ethyl | 197.3 | | | 19.2 |
| 97 | 6-fluoro-4H-benzo[d][1,3]dioxin-8-yl | 321.4 | 19.0 | 12.0 | |
| 98 | 3-(cylopentyloxy)-4-(methoxy)-phenyl | 359.4 | 2.87 | | 0.62 |
| 99 | 4-(heptyloxy)-phenyl | 359.5 | 5.6 | 9.9 | |
| 100 | 3,4-dihydro-2H-benzo[b][1,4]dioxepin-7-yl | 317.4 | | | |
| 101 | 4-(butoxy)-phenyl | 317.4 | | | |
| 102 | 3,4-(dimethoxy)-phenyl | 305.4 | | | 0.46 |

In a further embodiment, the present invention provides novel inhibitors of QC (EC) of the formula 1d,

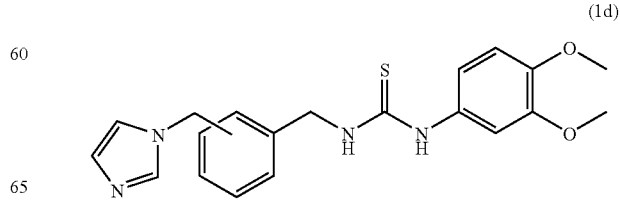

(1d)

wherein the position on the ring is defined in examples 103 to 105.

| Example | Position of the Benzyl-substitution | ESI-MS (M + H) | Res. Act. (%) | $K_i$ (μM) |
|---|---|---|---|---|
| 103 | 2 | 383.5 | 16.27 | 4.84 |
| 104 | 3 | 383.5 |  | 3.52 |
| 105 | 4 | 383.5 |  | 1.86 |

In a further embodiment, the present invention provides novel inhibitors of QC (EC) of the formula 1e,

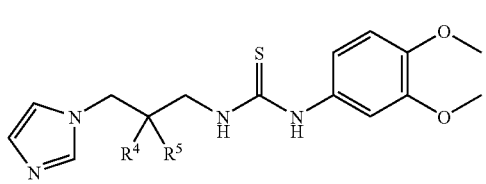
(1e)

wherein $R^4$ and $R^5$ are defined in examples 106 to 109.

| Example | $R^4$ | $R^5$ | ESI-MS (M + H) | Res.Act. (%) | $IC_{50}$ (μM) | $K_i$ (μM) |
|---|---|---|---|---|---|---|
| 106(S) | H | Methyl | 335.5 |  |  | 0.76 |
| 107(R) | Methyl | H | 335.5 |  |  | 0.35 |
| 108 | Methyl | Methyl | 349.5 |  |  |  |
| 109 | —CH$_2$—CH$_2$— |  | 347.5 |  |  | 7.85 |

In a further embodiment, the present invention provides novel inhibitors of QC (EC) of the formula 1f,

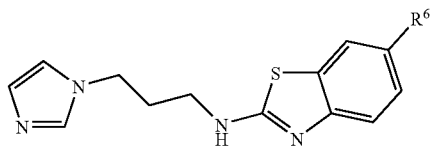
(1f)

wherein $R^6$ is defined in examples 110 to 112.

| Example | $R^6$ | ESI-MS (M + H) | Res. Act. (%) | $IC_{50}$ (μM) | $K_i$ (μM) |
|---|---|---|---|---|---|
| 110 | H | 259.4 |  |  | 3.00 |
| 111 | Chloro | 293.8 |  |  | 3.35 |
| 112 | Methoxy | 289.4 |  |  | 1.57 |

In a further embodiment, the present invention provides novel inhibitors of QC (EC) of the formula 1g,

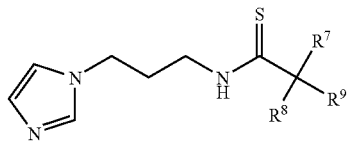
(1g)

wherein $R^7$, $R^8$ and $R^9$ are defined in examples 113 to 132.

| Example | $R^7$ | $R^8$ | $R^9$ | ESI-MS (M + H) | Res. Act. (%) | $K_i$ (μM) |
|---|---|---|---|---|---|---|
| 113 | Phenyl | H | H | 260.4 |  | 4.62 |
| 114 | Thiophen-2-yl | H | H | 266.5 |  | 3.29 |
| 115(R) | Phenyl | Methyl | H | 274.5 | 21.2 | 7.34 |
| 116(S) | Phenyl | H | Methyl | 274.5 | 8.1 | 3.51 |
| 117 | Phenyl | H | Ethyl | 288.5 |  | 3.57 |
| 118 | Phenyl | H | Phenyl | 336.5 | 13.5 | 4.48 |
| 119 | 3,4-(dimethoxy)-Phenyl | H | H | 320.5 |  | 0.39 |
| 120 | 3,4-(dimethoxy)-Phenyl | Methyl | Methyl | 347.2 |  |  |
| 121 | 4-(chloro)-phenyl | —CH$_2$—CH$_2$—CH$_2$— |  | 334.9 |  | 4.88 |
| 122 | 4-(chloro)-phenyl | —CH$_2$—C$_2$H$_4$—CH$_2$— |  | 349.0 |  | 7.3 |
| 123 | 4-(methoxy)-phenyl | —CH$_2$—C$_3$H$_6$—CH$_2$— |  | 358.6 |  | 2.78 |
| 124 | 4-(methoxy)-phenyl | —CH$_2$—CH$_2$— |  | 316.5 |  | 0.39 |
| 125 | 3,4-(dimethoxy)-Phenyl | —CH$_2$—CH$_2$— |  | 346.5 |  | 0.09 |
| 126 | 3,4,5-(trimethoxy)-Phenyl | —CH$_2$—CH$_2$— |  | 376.6 |  |  |
| 127 | 2,3,4-(trimethoxy)-Phenyl | —CH$_2$—CH$_2$— |  | 376.6 |  |  |
| 128 | 2-(methoxy)-phenyl | —CH$_2$—CH$_2$— |  | 316.5 |  |  |
| 129 | 3-(methoxy)-phenyl | —CH$_2$—CH$_2$— |  | 316.5 |  |  |

-continued

| Example | R⁷ | R⁸ | R⁹ | ESI-MS (M + H) | Res. Act. (%) | $K_i$ (μM) |
|---|---|---|---|---|---|---|
| 130 | 2,3-(dimethoxy)-Phenyl | | —CH₂—CH₂— | 346.5 | | |
| 131 | 3,5-(dimethoxy)-Phenyl | | —CH₂—CH₂— | 346.5 | | |
| 132 | 2,5-(dimethoxy)-Phenyl | | —CH₂—CH₂— | 346.5 | | |

In a further embodiment, the present invention provides novel inhibitors of QC (EC) of the formula 1h,

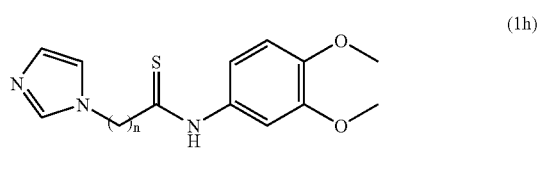

(1h)

wherein n is defined in examples 133 to 135.

| Example | N | ESI-MS (M + H) | $K_i$ (μM) |
|---|---|---|---|
| 133 | 3 | 306.4 | |
| 134 | 4 | 320.5 | 0.99 |
| 135 | 5 | 334.5 | |

In a further embodiment, the present invention provides novel inhibitors of QC (EC) of the formula 1i,

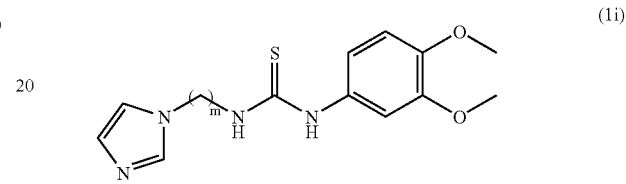

(1i)

wherein m is defined in examples 136 and 137.

| Example | m | ESI-MS (M + H) | Res. Act. (%) | $K_i$ (μM) |
|---|---|---|---|---|
| 136 | 2 | 307.4 | | 17.6 |
| 137 | 4 | 335.5 | 2.19 | 0.55 |

Further novel inhibitors of QC (EC) are examples 138 to 141.

| Example | Structure | ESI-MS (M + H) | Res.Act. (%) | IC₅₀ (μM) | $K_i$ (μM) |
|---|---|---|---|---|---|
| 138 | 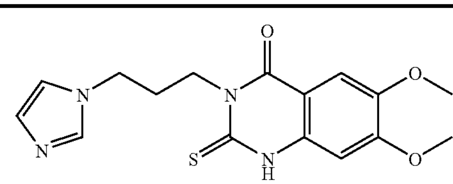 | 347.5 | | | |
| 139 | 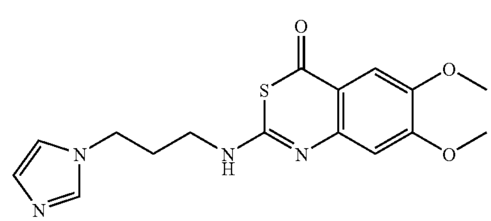 | 347.2 | | | |
| 140 | 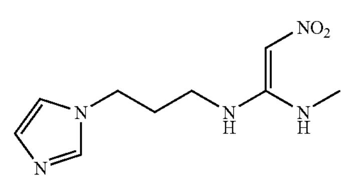 | 226.3 | 13.8 | | 20.5 |

-continued
| Example | Structure | ESI-MS (M + H) | Res.Act. (%) | IC$_{50}$ (μM) | K$_i$ (μM) |
|---|---|---|---|---|---|
| 141 | 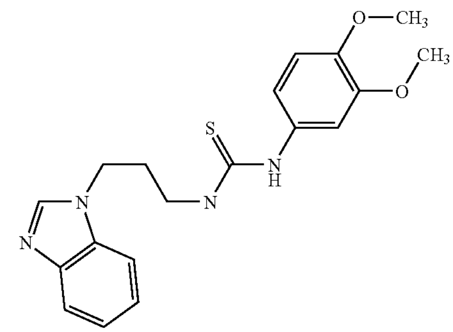 | 370.4 | | | |
SYNTHESIS OF THE EXAMPLES
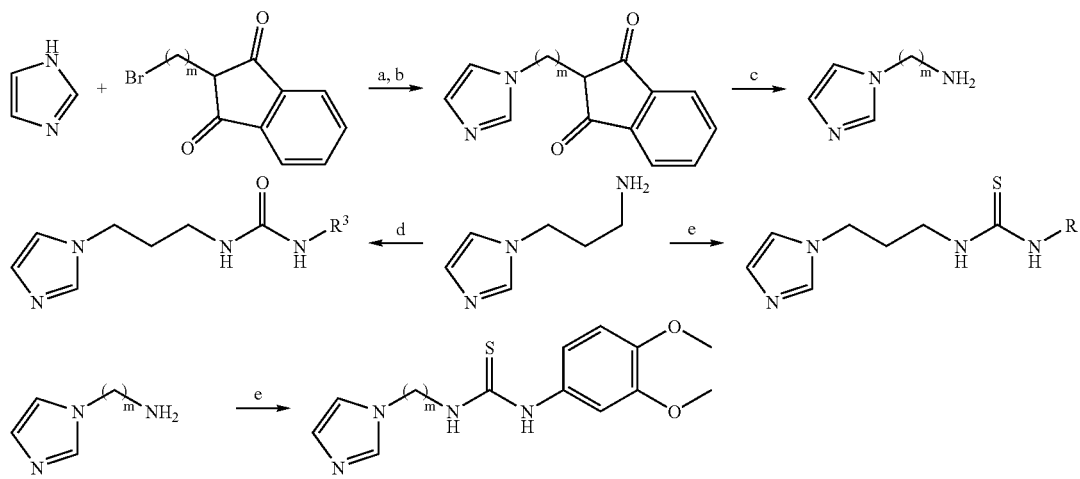
Reagents and conditions: (a) NaH, DMF, 4 h, rt.; (b), 8 h, 100° C.; (c) H$_2$N—NH$_2$,EtOH, 8 h, reflux then 4N HCl, 6 h, reflux, (d) R$^3$—NCO, EtOH, 6 h, reflux, (e) 3,4 dimethoxyphenyl-isothiocyanate,
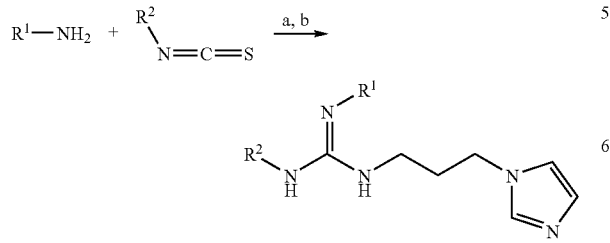
Reagents and conditions: (a) R—NCS, EtOH, 6 h, reflux; (b) WSCD, 1H-imidazole-1-propanamine, DMF, 2 h, r.t.
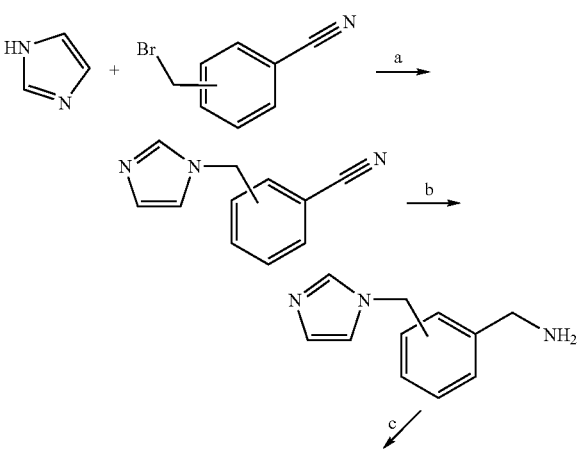

-continued

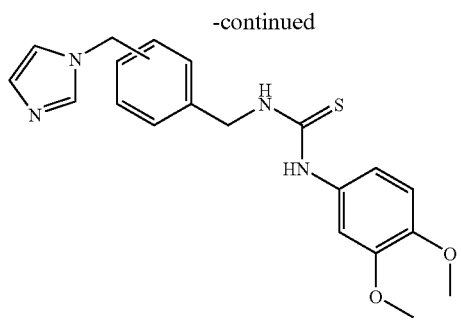

Reagents and conditions: (a) NaH, DMF, rt., 3 h; (b) LiAlH₄, dioxane, reflux, 1 h; (c) R—NCS, EtOH, reflux 6 h, Synthesis scheme 4: Synthesis of the examples 106-109

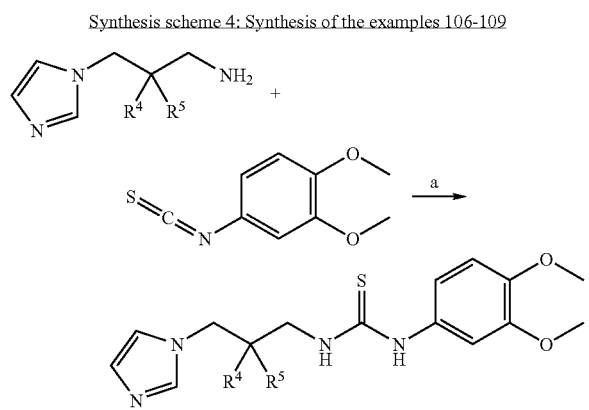

Reagents and conditions: (a) EtOH, 2 h, reflux

Synthesis scheme 5: Synthesis of the examples 110-112

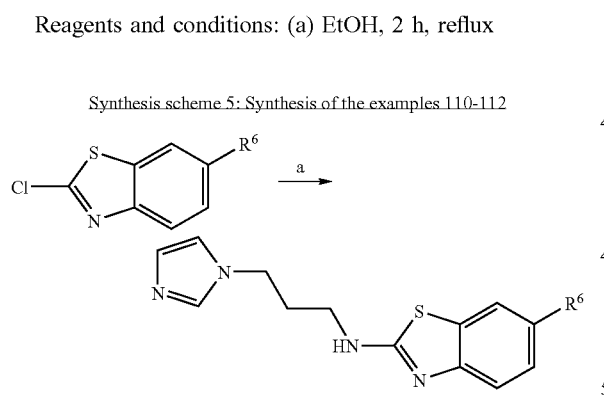

Reagents and conditions: (a) 1H-imidazole-1-propan-amine, Triethylamine, Toluene, 12 h, reflux Synthesis scheme 6: Synthesis of the examples 113-132

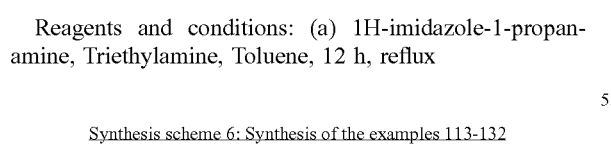

Reagents and conditions: (a) CAIBE, 1H-imidazole-1-propanamine, Dioxan, 0° C., 12 h; (b) Laweson's Reaent, EtOH, reflux, 8 h Synthesis scheme 7: Synthesis of the examples 133-135

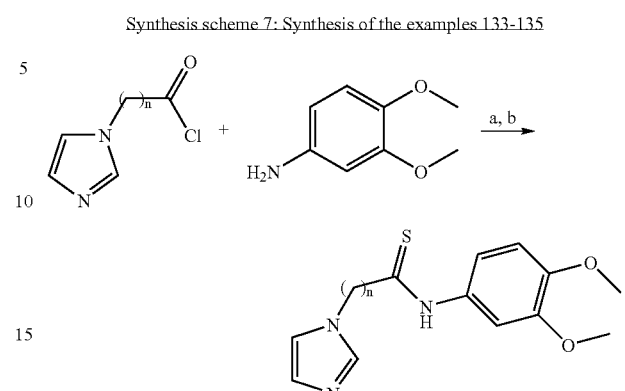

Reagents and conditions: (a) 1H-imidazole-1-propan acidic chloride, $CH_2Cl_2$, −10° C., 1 h; (b) Lawesson's Reagent, Dioxane, reflux, 8 h Synthesis scheme 8: Synthesis of the example 138

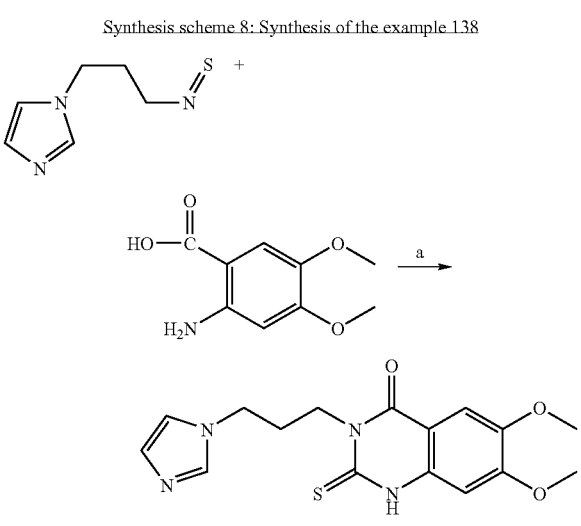

Reagents and conditions: (a) EtOH, reflux, 8 h

Synthesis scheme 9: Synthesis of the example 139

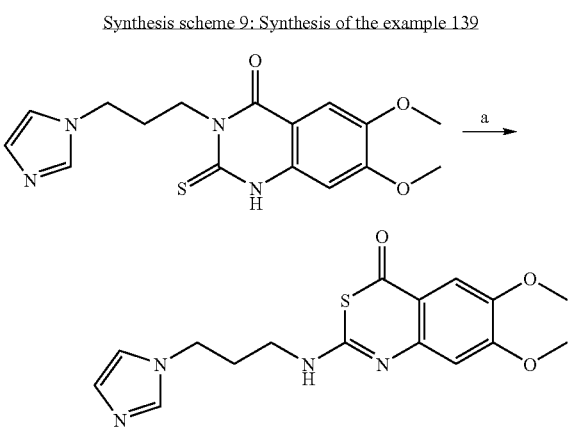

Reagents and conditions: (a) 75% conc. $H_2SO_4$, 4 h

Synthesis scheme 10: Synthesis of the example 140

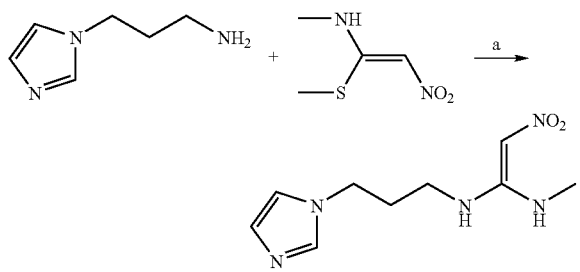

Reagents and conditions: (a) Acetonitrile, reflux 2 h

Synthesis scheme 11: Synthesis of the example 141

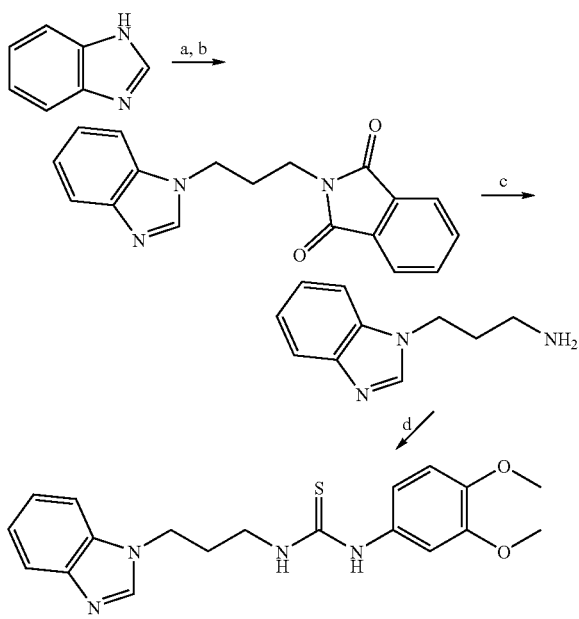

Reagents and conditions: (a) NaH, DMF, 4 h, rt.; (b), 8 h, 100° C.; (c) H$_2$N—NH$_2$, EtOH, 8 h, reflux then 4N HCl, 6 h, reflux, (d) 3,4 dimethoxy-phenyl-isothiocyanate, EtOH, 6 h, reflux Analytical Conditions ESI-Mass spectra were obtained with a SCIEX API 365 spectrometer (Perkin Elmer). The $^1$H-NMR (500 MHz) data was recorded on a BRUKER AC 500, using DMSO-D$_6$ as solvent. Chemical shifts are expressed as parts per million downfield from tetramethylsilane. Splitting patterns have been designated as follows: s (singulet), d (doublet), dd (doublet of doublet), t (triplet), m (multiplet), and br (broad signal).

DETAILED SYNTHESIS DESCRIPTION

Examples 1-12 and 14-53

1H-imidazole-1-propanamine was reacted with the corresponding isothiocyanate in ethanol under reflux for 8 h. After that the solvent was removed and the remaining oil was dissolved in methylene chloride. The organic layer was washed twice with a saturated solution of NaHCO$_3$ followed by NaHSO$_4$ and brine, dried then evaporated. The remaining solid was re-crystallized from ethyl acetate, yielding the example thiourea in yields of 80-98%.

Example 13

1-(3-(1H-imidazol-1-yl)propyl)-3-(3,4-dimethoxyphenyl)thiourea 4.0 mmol of 3,4-dimethoxyphenyl isothiocyanate and 4.0 mmol of 3-(1H-imidazol-1-yl)alkyl-1-amine were dissolved in 10 mL of absolute ethanol. After stirring for 2 h under reflux, the solvent was evaporated and the resulting solid was recrystallized from ethanol.

Yield: 0.66 g (51.3%); mp: 160.0-161.0° C. $^1$H NMR δ 1.8-2.0 (m, 2H), 3.4-3.5 (m, 2H), 3.75 (s, 6H), 3.9-4.0 (m, 2H), 6.7-6.8 (m, 1H), 6.9 (br m, 2H), 6.95 (s, 1H), 7.15 (s, 1H), 7.55 (br s, 1H), 7.6 (s, 1H), 9.3 (s, 1H); MS m/z 321.2 (M+H), 253.3 (M–C$_3$H$_3$N$_2$.)

Examples 96-102

1H-imidazole-1-propanamine was reacted with the corresponding isocyanate in ethanol under reflux for 8 h. After that the solvent was removed and the remaining oil was dissolved in methylene chloride. The organic layer was washed twice with a saturated solution of NaHCO$_3$ followed by NaHSO$_4$ and brine, dried then evaporated. The remaining solid was re-crystallized from ethyl acetate, yielding the example urea in yields of 85-90%.

Examples 136, 137

The 1H-imidazole-1-alkylamines were prepared according to the literature from ω-brom-alkyl-phtalimides and imidazolium salt and subsequent hydrazinolysis. The resulting products were transformed into the thioureas according to example 1-53 giving a 88% (example 136) and 95% (example 137) yield.

Examples 54-95

All examples were made from the corresponding thioureas by reacting with Water-soluble-carbodiimide (WSCD) and 1H-imidazole-1-propanamine in dry dimethyl formamide for 2 h at r.t. giving the trisubstituted guanidines with yields from 40-87%.

Examples 103-105

Imidazole was reacted with the corresponding brommethylphenylcyanide in DMF, utilizing 1 equivalent of NaH for 3 h under rt., giving the 1H-imidazole-1-methylphenylcyanides. The solvent was removed and the resulting oil was re-dissolved in dioxane. The cyanides were converted in the corresponding amines using 1 equivalent of LiAlH$_4$. After adding a saturated solution of KHSO$_4$, dioxane was evaporated and the aqueous layer was extracted by means of CHCl$_3$. The organic layer was concentrated in vacuo and the amine was converted in the corresponding thioureas according to example 1-53 giving a 78% (example 103) and 65% (example 104) and 81% (example 105) yield.

Examples 106-109

Starting from the corresponding methansulfonate-2-methylpropyl-phthalimides the amines were synthesized as described for the amines in example 136-137. The resulting products were transformed into the thioureas according to example 1-53 giving example 106-109 in total yields of 25-30%.

Examples 110-112

1H-imidazole-1-propanamine was reacted with the corresponding 2-chlorobenzo[d] thiazole in toluol for 24 h at a temperature of 130° C. After removing the solvent and recrystallization from methanol example 110-112 was yielded in an amount of 55-65%.

Examples 113-118, 120-124 and 126-132

1H-imidazole-1-propanamine was reacted with the corresponding 2-phenyl acetic acid in dry dioxane by adding one equivalent of CAIBE and N-methylmorpholine at a temperature of 0° C. After 2 h the mixture was allowed to warm to r.t. and the mixture was stirred for 12 h. After removing the solvent the resulting oil was redissolved in methylene chloride and the organic layer was washed by means of an aqueous solution of $NaHCO_3$ and water, dried and the solvent was evaporated. The remaining oil was dissolved in dioxane adding Laweson's Reagent. After stirring for 12 h a saturated solution of $NaHCO_3$ was added. Dioxane was evaporated and the aqueous layer was extracted by means of ethyl acetate. The organic layer was separated, dried and the solvent was evaporated. The remainig solid was crystallized from acetyl acetate/ether, giving 113-118, 120-124 and 126-132 with total yields of 62-85%.

Example 119

N-(3-(1H-imidazol-1-yl)propyl)-2-(3,4-dimethoxyphenyl)ethanethioamide

A mixture of 4.0 mmol triethylamine and 4.0 mmol of 3-(1H-imidazol-1-yl)alkyl-1-amine 20 mL of dioxane was added drop wise to an ice cooled, stirred solution of 4.0 mmol of 2-(3,4-dimethoxyphenyl)acetyl chloride in 30 mL of dioxane. The mixture was allowed to warm to r.t., and then stirred for 1 h. After removing the solvent by reduced pressure, the residue was redissolved in 50 mL of dichloromethane. The organic layer was washed by means of 30 mL of saturated aqueous solution of $NaHCO_3$, and water. The organic solution was dried, filtered, and the solvent was removed under reduced pressure. After redissolving in 50 mL of dry dioxane 2.2 mmol of Lawesson's reagent was added, and the mixture was heated to 90° C. and stirred for 8 h. The solvent was removed by reduced pressure, and the residue was redissolved in 50 mL of dichloromethane. The organic layer was washed three times by means of a saturated aqueous solution of $NaHCO_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a $CHCl_3$/MeOH gradient as eluting system.

Yield: 0.14 g (10.6%); melting point: 148.0-150.0° C. $^1$H NMR δ 2.0-2.15 (br m, 2H), 3.4-3.5 (m, 2H), 3.7 (s, 6H), 6.75-6.8 (m, 2H), 4.1-4.2 (m, 2H), 6.8-6.9 (m, 2H), 6.95-7.0 (m, 1H), 7.4 (s, 1H), 7.75-7.85 (br m, 1H), 8.6 (s, 1H), 10.2 (s, 1H); MS m/z 320.2 (M+H), 252.2 (M–$C_3H_3N_2$.)

Example 125

N-(3-(1H-imidazol-1-yl)propyl)-1-(3, 4-dimethoxyphenyl)cyclopropanecarbothioamide 11.06 mmol of 3,4-dimethoxyphenyl acetonitrile, 34.8 mmol of 2-Bromo-1-chloroethanole and 1.16 mmol of triethylbenzylammonium hydrochloride were dissolved in 10 mL of an aqueous solution of KOH (60%). The mixture was transferred into an ultrasonic bath and vigorously stirred for 3 h at room temperature. The resulting suspension was diluted with 40 mL of water and extracted three times by means of 20 mL of dichloromethane. The combined organic layers where washed by means of an aqueous solution of hydrochloric acid (1N), dried over $Na_2SO_4$ and the solvent was removed under reduced pressure. The remaining oil was purified by flash-chromatography using silica gel and ethyl acetate/heptane as eluting system, resulting in 0.81 g (34.4%) of 1-(3,4-dimethoxyphenyl)cyclopropanecarbonitrile 3.9 mmol of 1-(3,4-dimethoxyphenyl)cyclopropanecarbonitrile and 11.2 mmol of KOH were suspended in 80 mL of ethylene glycol. The mixture was stirred for 12 h under reflux. Then 80 mL of water were added and the aqueous layer was extracted two times with ether. After pH adjustment to a value of pH=4-5 using HCl (1N) the aqueous layer was extracted three times by means of ether, then the combined organic layers were dried over $Na_2SO_4$ and the solvent was removed, resulting in 0.81 g (93.5%) of 1-(3, 4-dimethoxyphenyl)cyclopropanecarboxylic acid.

3.44 mmol of 1-(3,4-dimethoxyphenyl)cyclopropanecarboxylic acid, 3.5 mmol of N-Methyl morpholine, and 3.5 mmol of isobutyl chloroformiat were dissolved in dry tetrahydrofurane and stirred for 15 min at –15° C. Then 3.5 mmol of 3-(1H-imidazol-1-yl)alkyl-1-amine was added and the mixture was allowed to warm to 0° C. and was stirred for 12 h. The solvent was removed under reduced pressure and the remaining oil was redissolved in chloroform. Then the organic layer was washed two times by means of a saturated aqueous solution of $NaHCO_3$, then dried over $Na_2SO_4$ and the solvent was removed. Purification was performed by means of centrifugal forced chromatography using a chromatotron® device (Harrison Research Ltd.) utilizing silica plates of a layer thickness of 2 mm, and a $CHCl_3$/MeOH gradient as eluting system resulting in 0.671 g (59.3%) of N-(3-(1H-imidazol-1-yl)propyl)-1-(3,4-dimethoxyphenyl) cyclopropane-carboxamide.

After redissolving in 30 mL of dry dioxane 1.43 mmol of Lawesson's reagent were added, and the mixture was heated to 90° C. and stirred for 8 h. The solvent was removed by reduced pressure, and the residue was remains were dissolved in 50 mL of dichloromethane. The organic layer was washed three times by means of a saturated aqueous solution of $NaHCO_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a $CHCl_3$/MeOH gradient as eluting system.

Yield: 0.33 g (46.2%); melting point: 127.0-127.5° C. $^1$H NMR δ 1.1-1.2 (t, 2H), 1.55-1.6 (t, 2H), 2.0-2.1 (m, 2H), 3.5-3.6 (m, 2H), 3.7-3.8 (s, 6H), 4.1-4.2 (t, 2H), 6.8-6.9 (m, 3H), 7.65 (s, 1H), 7.75 (s, 1H), 8.8 (m, 1H), 9.05 (s, 1H; MS m/z 346.0 (M+H), 278.2 (M–$C_3H_3N_2$.), 177.1 (M–$C_6H_8N_3S$.)

Examples 133-135

A mixture of 1 equivalent triethylamine and 3,4-dimethoxyaniline in dioxane was added to an stirred solution of the corresponding ω-bromoalkyl acidic chloride at a temperature of 0° C. The solution was allowed to warm to r.t. and stirred for 2 h. The solvent was evaporated, and the remaining oil was redissolved in dichloromethane. The organic layer was washed by means of water, dried, filtered, and the solvent was removed under reduced pressure.

Imidazole and sodium hydride were suspended in and the mixture was stirred under inert conditions at r.t. for 3 h. ω-Bromo-N-(3,4-dimethoxy-phenyl)alkylamide was added and the mixture was heated to 100° C. and stirred for 8 h. After that, the solvent was evaporated, hot toluene were added and the solution was filtered. Then the solvent was removed under reduced pressure. The transformation into the thioamides was performed as described for example 113-132 by means of Laweson's reagent, giving 133-135 in total yields of 13-20%.

The analytical data for further examples, which were syntesized according to the general synthesis schemes described above, are as follows:

Example 1

1-(3-(1H-imidazol-1-yl)propyl)-3-methylthiourea melting point: 122-122.5° C. $^1$H NMR δ 1.85-1.95 (m, 2H), 2.8 (s, 3H), 3.2-3.5 (br d, 2H), 3.8-3.9 (m, 2H), 6.85 (d, 1H), 7.15 (d, 1H), 7.3-7.5 (br d, 2H), 7.65 (s, 1H); MS m/z 199.1 (M+H), 221.3 (M+Na), 131.0 (M–$C_3H_3N_2$.)

Example 2

1-(3-(1H-imidazol-1-yl)propyl)-3-tert-butylthiourea melting point: 147.0-147.5° C. $^1$H NMR δ 1.3-1.4 (s, 9H), 1.85-1.95 (m, 2H), 3.5 (t, 2H), 3.8 (t, 2H), 6.85 (d, 1H), 7.15 (d, 1H), 7.3-7.5 (br d, 2H), 7.65 (s, 1H); MS m/z 241.1 (M+H), 173.1 (M–$C_3H_3N_2$.)

Example 3

1-(3-(1H-imidazol-1-yl)propyl)-3-benzylthiourea melting point: 127.0-128.0° C. $^1$H NMR δ 1.85-1.95 (m, 2H), 3.2-3.5 (br d, 2H), 3.8-3.9 (m, 2H), 4.6 (s, 2H), 6.8 (d, 1H), 7.15 (d, 1H), 7.19-7.35 (m, 5H), 7.5-7.6 (br d, 2H), 7.85 (s, 1H); MS m/z 275.3 (M+H), 207.1 (M–$C_3H_3N_2$.)

Example 5

1-(3-(1H-imidazol-1-yl)propyl)-3-phenylthiourea melting point: 166.5-167.0° C. $^1$H NMR δ 1.95-2.05 (m, 2H), 3.3-3.5 (br d, 2H), 3.9-4.0 (m, 2H), 6.85 (d, 1H), 7.05 (m, 1H) 7.15 (d, 1H), 7.25 (m, 2H), 7.35 (m, 2H), 7.6 (s, 1H), 7.8 (br s, 1H), 9.5 (br s, 1H); MS m/z 261.1 (M+H), 193.2 (M–$C_3H_3N_2$.)

Example 6

1-(3-(1H-imidazol-1-yl)propyl)-3-(4-fluorophenyl)thiourea melting point: 147.0-148.0° C. $^1$H NMR δ 1.95-2.05 (m, 2H), 3.3-3.5 (br d, 2H), 3.9-4.05 (m, 2H), 6.85 (d, 1H), 7.05-7.15 (m, 3H), 7.3-7.4 (m, 2H), 7.6 (s, 1H), 7.7-7.8 (br s, 1H), 9.4 (br s, 1H); MS m/z 279.3 (M+H), 211.2 (M–$C_3H_3N_2$.)

Example 7

1-(3-(1H-imidazol-1-yl)propyl)-3-(4-ethylphenyl)thiourea melting point: 100.0-100.5° C. $^1$H NMR δ 1.15-1.2 (t, 3H), 1.9-2.0 (m, 2H), 2.5-2.6 (m, 2H), 3.3-3.5 (br d, 2H), 3.9-4.05 (m, 2H), 6.85 (d, 1H), 7.1-7.2 (m, 3H), 7.25-7.3 (m, 2H), 7.6 (s, 1H), 7.7-7.8 (br s, 1H), 9.4 (br s, 1H); MS m/z 289.3 (M+H), 221.1 (M–$C_3H_3N_2$.)

Example 8

1-(3-(1H-imidazol-1-yl)propyl)-3-(4-(trifluoromethyl)phenyl)thiourea melting point: 154.5-155.0° C. $^1$H NMR δ 1.9-2.1 (br m, 2H), 3.4-3.6 (br d, 2H), 3.95-4.1 (br m, 2H), 6.85 (d, 1H), 7.2 (d, 1H), 7.6-7.8 (m, 5H), 8.2 (br s, 1H), 9.9 (br s, 1H); MS m/z 329.3 (M+H), 261.2 (M–$C_3H_3N_2$.)

Example 10

1-(3-(1H-imidazol-1-yl)propyl)-3-(4-acetylphenyl)thiourea melting point: 170.0-171.0° C. $^1$H NMR δ 1.9-2.1 (br m, 2H), 2.4-2.5 (s, 3H), 3.2-3.5 (br m, 2H), 3.9-4.1 (m, 2H), 6.85 (d, 1H), 7.15 (d, 1H), 7.5-7.65 (br m, 3H), 7.8-7.9 (m, 2H), 8.1 (m, 2H), 9.8 (br s, 1H); MS m/z 303.2 (M+H), 235.1 (M–$C_3H_3N_2$.)

Example 11

1-(3-(1H-imidazol-1-yl)propyl)-3-(4-methoxyphenyl)thiourea melting point: 125.0-125.5° C. $^1$H NMR δ 1.8-2.0 (br m, 2H), 3.2-3.5 (br m, 2H), 3.7 (s, 3H), 3.9-4.0 (m, 2H), 6.7-6.9 (m, 3H), 7.1-7.2 (m, 3H), 7.5 (s, 1H), 7.6 (s, 1H), 9.2 (s, 1H); MS m/z 291.1 (M+H), 223.2 (M–$C_3H_3N_2$.)

Example 14

1-(3-(1H-imidazol-1-yl)propyl)-3-(2,4-dimethoxyphenyl)thiourea melting point: 120.0-120.5° C. $^1$H NMR δ 1.8-2.0 (br m, 2H), 3.4-3.5 (br m, 2H), 3.75 (s, 6H), 3.9-4.0 (m, 2H), 6.5 (d, 1H), 6.6 (s, 1H), 6.9 (s, 1H), 7.15 (s, 1H), 7.3 (d, 1H), 7.5 (br s, 1H), 7.6 (s, 1H), 9.75 (s, 1H); MS m/z 321.2 (M+H), 253.3 (M–$C_3H_3N_2$.)

Example 15

1-(3-(1H-imidazol-1-yl)propyl)-3-(3,5-dimethoxyphenyl)thiourea melting point: 142.0-143.0° C. $^1$H NMR δ 1.8-2.0 (br m, 2H), 3.4-3.5 (br m, 2H), 3.6 (s, 6H), 3.95-4.0 (m, 2H), 6.25 (m, 1H), 6.6 (m, 2H), 6.9 (s, 1H), 7.2 (s, 1H), 7.6 (s, 1H), 7.8 (s, 1H), 9.5 (s, 1H); MS m/z 321.2 (M+H), 253.3 (M–$C_3H_3N_2$.)

Example 23

1-(3-(1H-imidazol-1-yl)propyl)-3-(2,3-dihydrobenzo[b][1,4]dioxin-7-yl)thiourea melting point: 103.0-103.5° C. $^1$H NMR δ 1.9-2.0 (br m, 2H), 3.3-3.5 (br d, 2H), 3.9-4.0 (m, 2H), 4.2-4.3 (m, 4H), 6.7 (m, 1H), 6.8-6.8 (m, 1H), 6.9 (m, 2H), 7.2 (s, 1H), 7.6 (m, 2H), 9.3 (s, 1H); MS m/z 319.3 (M+H), 251.3 (M–$C_3H_3N_2$.)

Example 24

1-(3-(1H-imidazol-1-yl)propyl)-3-(benzo[d][1,3]dioxol-6-yl)thiourea melting point: 115.0-115.6° C. $^1$H NMR δ 1.9-2.1 (br m, 2H), 3.4-3.5 (br d, 2H), 4.05-4.15 (m, 2H), 6.0 (s, 2H), 6.7 (m, 1H), 6.8-6.85 (m, 1H), 6.95 (d, 1H), 7.25 (s, 1H), 7.45 (s, 1H), 7.7 (br s, 1H), 8.5 (br s, 1H), 9.4 (br s, 1H); MS m/z 305.2 (M+H), 237.2 (M–$C_3H_3N_2$.)

Example 25

1-(3-(1H-imidazol-1-yl)propyl)-3-(3,4,5-trimethoxyphenyl)thiourea melting point: 124.5-125.5° C. $^1$H NMR δ 1.8-2.0 (m, 2H), 3.4-3.5 (br m, 2H), 3.6 (s, 3H), 3.7 (s, 6H), 3.9-4.0 (m, 2H), 6.65 (m, 2H), 6.85 (s, 1H), 7.2 (s, 1H), 7.6 (s, 1H), 7.7 (br s, 1H), 9.4 (s, 1H); MS m/z 351.3 (M+H), 283.2 (M–$C_3H_3N_2$.)

Example 26

1-(3-(1H-imidazol-1-yl)propyl)-3-(3-methoxyphenyl)thiourea melting point: 89.5-90.0° C. $^1$H NMR δ 1.9-2.1 (br m, 2H), 3.4-3.5 (br m, 2H), 3.7 (s, 3H), 3.9-4.0 (m, 2H), 6.6-6.7 (m, 1H), 6.8-6.9 (m, 2H), 7.1 (m, 2H), 7.15-7.25 (br m, 1H), 7.6 (s, 1H), 7.8 (br s, 1H), 9.5 (s, 1H); MS m/z 291.1 (M+H), 223.2 (M–$C_3H_3N_2$.)

Example 27

1-(3-(1H-imidazol-1-yl)propyl)-3-(4-ethoxyphenyl)thiourea melting point: 126.0-126.5° C. $^1$H NMR δ 1.5 (br m, 3H), 1.9-2.0 (br m, 2H), 3.4-3.5 (br m, 2H), 3.9-4.0 (br m, 4H), 6.8-6.9 (m, 2H), 6.95 (s, 1H), 7.15-7.2 (m, 2H), 7.25 (s, 1H), 7.55-7.6 (br s, 1H), 7.8 (s, 1H), 9.3 (s, 1H); MS m/z 305.2 (M+H), 237.2 (M–$C_3H_3N_2$.)

Example 33

1-(3-(1H-imidazol-1-yl)propyl)-3-(4-(methylthio)phenyl)thiourea melting point: 140.0-140.5° C. $^1$H NMR δ 1.8-2.05 (br m, 2H), 2.5 (s, 3H), 3.3-3.5 (br m, 2H), 3.9-4.1 (m, 2H), 6.9 (m, 1H), 7.1-7.3 (br m, 5H), 7.6 (s, 1H), 7.75 (br s, 1H), 9.4 (s, 1H); MS m/z 307.2 (M+H), 239.2 (M–$C_3H_3N_2$.)

Example 42

1-(3-(1H-imidazol-1-yl)propyl)-3-(4-nitrophenyl)thiourea melting point: 165.0. 166.0° C. $^1$H NMR δ 1.9-2.05 (m, 2H), 3.3-3.5 (br d, 2H), 3.95-4.05 (m, 2H), 6.85 (d, 1H), 7.15 (d, 1H), 7.6 (d, 1H), 7.7 (m, 2H), 8.1 (m, 2H), 8.3 (br s, 1H), 10.1 (br s, 1H); MS m/z 306.2 (M+H), 237.9 (M–$C_3H_3N_2$.)

Example 50

1-(3-(1H-imidazol-1-yl)propyl)-3-(4-(dimethylamino)phenyl)thiourea melting point: 146.5-147.0° C. $^1$H NMR δ 1.9-2.0 (m, 2H), 2.9 (s, 6H), 3.4 (m, 2H), 3.9-4.0 (m, 2H), 6.7 (m, 2H), 6.9 (s, 1H), 7.05-7.1 (m, 2H), 7.15 (s, 1H), 7.4 (br s, 1H), 7.6 (s, 1H), 9.2 (s, 1H); MS m/z 304.2 (M+H), 236.0 (M–$C_3H_3N_2$.)

Example 102

1-(3-(1H-imidazol-1-yl)propyl)-3-(3,4-dimethoxyphenyl)urea melting point: 114.5-115.0° C. $^1$H NMR δ 1.7-1.9 (m, 2H), 2.9-3.1 (m, 2H), 3.7 (2s, 6H), 3.9-4.0 (m, 2H), 6.1 (t, 1H), 6.7 (s, 2H), 6.8 (s, 1H), 7.15 (d, 2H), 7.6 (s, 1H), 8.2 (s, 1H); MS m/z 321.2 (M+H), 253.3 (M–$C_3H_3N_2$.)

Example 106

1-((S)-3-(1H-imidazol-1-yl)-2-methylpropyl)-3-(3,4-dimethoxyphenyl)thiourea melting point: 150.5-151.5° C. $^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.6 (M+H), 267.1 (M–$C_3H_3N_2$.)

Example 107

1-((R)-3-(1H-imidazol-1-yl)-2-methylpropyl)-3-(3,4-dimethoxyphenyl)thiourea melting point: 155.0-157.5° C. $^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.4 (M+H), 267.2 (M–$C_3H_3N_2$.)

Example 109

1-((1-((1H-imidazol-1-yl)methyl)cyclopropyl)methyl)-3-(3,4-dimethoxyphenyl)thiourea melting point: 166.5-168.5° C. $^1$H NMR δ 0.7-0.8 (br m, 2H), 1.85-1.9 (m, 1H), 2.15-2.2 (m, 1H), 2.2-2.3 (m, 1H), 3.4-3.5 (m, 1H), 3.7 (d, 6H), 4.2 (s, 1H), 4.95 (s, 1H), 6.75-6.8 (br m, 1H), 6.85-6.9 (br m, 1H), 7.0 (m, 1H), 7.5 (m, 1H), 7.6 (m, 1H), 7.7 (s, 0.5H), 7.8 (s, 0.5H), 8.85 (s, 0.5H), 9.1 (s, 0.5H), 9.35 (s, 0.5H), 9.45 (s, 0.5H); MS m/z 347.2 (M+H), 279.2 (M–$C_3H_3N_2$.), 137.5 (M–$C_9H_{13}N_4S$.)

Example 110

N-(3-(1H-imidazol-1-yl)propyl)benzo[d]thiazol-2-amine $^1$H NMR δ 1.95-2.15 (m, 2H), 3.25-3.35 (m, 2H), 4.0-4.1 (t, 2H), 6.9 (s, 1H), 6.95-7.05 (t, 1H), 7.15-7.2 (m, 2H), 7.35-7.4 (d, 1H), 7.60-7.70 (m, 2H), 8.0-8.1 (br s, 1H); MS m/z 259.4 (M+H), 191.3 (M–$C_3H_3N_2$.)

Example 111

N-(3-(1H-imidazol-1-yl)propyl)-6-chlorobenzo[d]thiazol-2-amine $^1$H NMR δ 1.95-2.15 (m, 2H), 3.25-3.35 (m, 2H), 4.0-4.1 (t, 2H), 6.9 (s, 1H), 7.1-7.2 (d, 2H), 7.3-7.4 (d, 1H), 7.65 (s, 1H), 7.8 (s, 1H), 8.2 (s, 1H); MS m/z 293.3 (M+H), 225.3 (M–$C_3H_3N_2$.)

Example 112

N-(3-(1H-imidazol-1-yl)propyl)-6-methoxybenzo[d]thiazol-2-amine $^1$H NMR δ 1.9-2.05 (m, 2H), 3.2-3.3 (m, 2H), 3.7 (s, 3H), 4.0-4.1 (t, 2H), 6.7-6.8 (d, 1H), 6.9 (s, 1H), 7.15-7.2 (s, 1H), 7.2-7.3 (m, 2H), 7.65 (s, 1H), 7.8 (s, 1H); MS m/z 289.1 (M+H), 221.4 (M–$C_3H_3N_2$.)

Example 115

(R)—N-(3-(1H-imidazol-1-yl)propyl)-2-phenylpropanethioamide melting point: 82.0-82.5° C. $^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M–$C_3H_3N_2$.)

Example 116

(S)—N-(3-(1H-imidazol-1-yl)propyl)-2-phenylpropanethioamide melting point: 82.5-83.5° C. $^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M–$C_3H_3N_2$.)

Example 121

N-(3-(1H-imidazol-1-yl)propyl)-1-(4-chlorophenyl)cyclobutanecarbothioamide melting point: 137.5-139.0° C. $^1$H NMR δ 1.55-1.75 (br m, 2H), 1.85-1.95 (br m, 2H), 2.4-2.5 (br m, 2H), 2.7-2.85 (br m, 2H), 3.3-3.5 (br m, 2H), 3.8 (m, 2H), 6.9 (s, 1H), 7.0 (s, 1H), 7.3 (m, 2H), 7.45 (s, 1H), 7.5 (m, 2H), 9.6 (t, 1H); MS m/z 334.3 (M+H), 266.1 (M–$C_3H_3N_2$.)

Example 122

N-(3-(1H-imidazol-1-yl)propyl)-1-(4-chlorophenyl)cyclopentanecarbothioamide melting point: 140.0-141.0° C. $^1$H NMR δ 1.5-1.65 (br m, 4H), 1.8-1.9 (m, 2H), 2.0-2.1 (m, 2H), 2.6 (m, 2H), 3.4-3.5 (m, 2H), 3.7-3.8 (m, 2H), 6.85 (s, 1H), 7.0 (s, 1H), 7.35 (m, 2H), 7.4 (m, 2H), 7.5 (s, 1H), 9.4 (t, 1H); MS m/z 348.2 (M+H), 280.2 (M–$C_3H_3N_2$.)

Example 123

N-(3-(1H-imidazol-1-yl)propyl)-1-(4-methoxyphenyl)cyclohexanecarbothioamide melting point: 162.5-164.0° C. $^1$H NMR δ 1.2-1.3 (m, 1H), 1.35-1.5 (br m, 5H), 1.85-2.0 (br m, 4H), 2.4-2.6 (br m, 2H), 3.4-3.5 (m, 2H), 3.7 (s, 3H), 3.8 (m, 2H), 6.8 (m, 3H), 7.0 (s, 1H), 7.3 (m, 2H), 7.5 (s, 1H), 9.2 (t, 1H); MS m/z 358.3 (M+H), 290.3 (M–$C_3H_3N_2$.)

Example 124

N-(3-(1H-imidazol-1-yl)propyl)-1-(4-methoxyphenyl)cyclopropanecarbothioamide melting point: 129.0-129.5° C. $^1$H NMR δ 1.0-1.1 (m, 2H), 1.5-1.6 (m, 2H), 1.9-2.0 (br m, 2H), 3.4-3.5 (m, 2H), 3.7 (s, 3H), 3.9 (m, 2H), 6.9 (m, 3H), 7.1 (s, 1H), 7.2-7.3 (m, 2H), 7.6 (s, 1H), 8.9 (br s, 1H); MS m/z 316.0 (M+H), 248.4 (M–$C_3H_3N_2$.)

Example 134

5-(1H-imidazol-1-yl)-N-(3,4-dimethoxyphenyl)pentanethioamide melting point: 128.0-128.5° C. $^1$H NMR δ 1.65-1.70 (m, 2H), 1.75-1.80 (m, 2H), 2.7-2.75 (m, 2H), 3.7 (s, 3H), 3.75 (s, 3H), 4.0-4.05 (t, 2H), 6.9-7.0 (m, 2H), 7.2 (s, 1H), 7.3 (d, 1H), 7.5 (s, 1H), 7.75 (s, 1H), 11.0 (s, 1H); MS m/z 320.2 (M+H), 252.2 (M–$C_3H_3N_2$.)

Example 136

1-(2-(1H-imidazol-1-yl)ethyl)-3-(3,4-dimethoxyphenyl)thiourea melting point: 157.5-159.0° C. $^1$H NMR δ 3.7 (2 s, 6H), 3.8 (m, 2H), 4.2 (m, 2H), 6.7 (m, 1H), 6.85 (m, 1H), 6.9 (m, 2H), 7.15 (s, 1H), 7.5 (br s, 1H), 7.6 (s, 1H), 9.5 (s, 1H); MS m/z 307.2 (M+H), 239.1 (M–$C_3H_3N_2$.)

Example 137

1-(4-(1H-imidazol-1-yl)butyl)-3-(3,4-dimethoxyphenyl)thiourea melting point: 114.5-116.0° C. $^1$H NMR δ 1.4-1.5 (m, 2H), 1.6-1.7 (m, 2H), 3.4-3.5 (m, 2H), 3.6-3.8 (br s, 6H), 3.9-4.0 (m, 2H), 6.7 (m, 1H), 6.9 (m, 2H), 6.95 (s, 1H), 7.2 (s, 1H), 7.6 (br s, 1H), 7.7 (s, 1H), 9.3 (s, 1H); MS m/z 335.3 (M+H), 267.1 (M–$C_3H_3N_2$.)

Physiological substrates of QC (EC) in mammals are, e.g. [Glu$^3$] amyloid β-protein (3-40/42), [Gln$^3$] amyloid β-protein (3-40/42), Gastrin, Neurotensin, FPP, CCL 2, CCL 7, CCL 8, CCL 16, CCL 18, Fractalkine, Orexin A, [Gln$^3$]-glucagon(3-29) and [Gln$^5$]-substance P(5-11). For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which is known to be cyclized to final pGlu

| Peptide | Amino acid sequence | Function |
| --- | --- | --- |
| Gastrin 17<br>Swiss-Prot: P01350 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin<br>Swiss-Prot: P30990 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH<br>Swiss-Prot: P20396 | QHP amide | TRH functions as a regulator of the biosynthesis of TSH in the anterior pituitary gland and as a neurotransmitter/neuromodulator in the central and peripheral nervous systems. |
| GnRH<br>Swiss-Prot: P01148 | QHWSYGL RP(G) amide | Stimulates the secretion of gonadotropins; it stimulates the secretion of both luteinizing and follicle-stimulating hormones. |
| CCL16 (small inducible cytokine A16)<br>Swiss-Prot: O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8)<br>Swiss-Prot: P80075 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host |

TABLE 1-continued

Amino acid sequences of physiological active peptides with an N-terminal glutamine residue, which is known to be cyclized to final pGlu

| Peptide | Amino acid sequence | Function |
|---|---|---|
| | | responses. This protein can bind heparin. |
| CCL2 (small inducible cytokine A2) Swiss-Prot: P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18) Swiss-Prot: P55774 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium. binds to CX3CR1. |
| CCL7 (small inducible cytokine A7) Swiss-Prot: P80098 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot O43612 | QPLPDCCRQK TCSCRLYELL HGAGNHAAGI LTL | Neuropeptide that plays a significant role in the regulation of food intake and sleep-wakefulness, possibly by coordinating the complex behavioral and physiologic responses of these |

TABLE 1-continued

Amino acid sequences of physiological active peptides with an
N-terminal glutamine residue, which is known to be cyclized to
final pGlu

| Peptide | Amino acid sequence | Function |
| --- | --- | --- |
| | | complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P | RPK PQQFFGLM | Belongs to the tachykinins. Tachykinins are active peptides which excite neurons, evoke behavioral responses, are potent vasodilators and secretagogues, and contract (directly or indirectly) many smooth muscles. |

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2, CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertention, liver fibrosis, liver cirrhosis, nephrosclerosis, ventricular remodeling, heart failure, arteriopathy after organ transplantations and failure of vein grafts.

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, J Pept Res 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

By administering a QC (EC)-inhibitor and/or a combination according to the present invention to a mammal it can be possible to prevent or alleviate or treat conditions selected from Alzheimer's disease, Down Syndrome, ulcer disease and gastric cancer with or w/o *Helicobacter pylori* infections, neoplasia, inflammatory host responses, cancer, melanoma, malign metastasis, psoriasis, rheumatoid arthritis, atherosclerosis, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Furthermore, by administration of a QC (EC)-inhibitor and/or a combination according to the present invention to a mammal it can be possible to stimulate the proliferation of myeloid progenitor cells.

In addition, the administration of a QC (EC)-inhibitor and/or a combination according to the present invention can lead to suppression of male fertility.

In a preferred embodiment, the present invention provides a composition, preferably a pharmaceutical composition comprising at least one QC (EC) inhibitor of formula 1 optionally in combination with at least one compound selected from the group consisting of PEP-inhibitors, LiCl, inhibitors of dipeptidyl aminopeptidases, preferably inhibitors of DP IV or DP IV-like enzymes, NPY-receptor ligands, NPY agonists, acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), monoamine oxidase (MAO) inhibitors, TNFalpha inhibitors, amyloid protein or amyloid peptide deposition inhibitors, sigma-1 receptor inhibitors and histamine H3 antagonists.

Further, the present invention provides pharmaceutical compositions e.g. for parenteral, enteral or oral administration, comprising at least one QC inhibitor of formula 1 optionally in combination with at least one compound selected from the group consisting of PEP-inhibitors, LiCl, inhibitors of dipeptidyl aminopeptidases, preferably inhibitors of DP IV or DP IV-like enzymes, NPY-receptor ligands, NPY agonists, acetylcholinesterase (ACE) inhibitors, protein isoaspartate carboxymethyl transferase (PIMT) enhancers, inhibitors of beta secretases, inhibitors of gamma secretases, inhibitors of neutral endopeptidase, inhibitors of Phosphodiesterase-4 (PDE-4), MAO inhibitors, TNFalpha inhibitors, amyloid protein or amyloid peptide deposition inhibitors, sigma-1 receptor inhibitors and histamine H3 antagonists, optionally in combination with customary carriers and/or excipients.

These combinations provide a particularly beneficial effect on behavioral conditions and such combinations are therefore shown to be effective and useful for the treatment of neuronal disorders, e.g. neuronal diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

Accordingly, the invention provides a method for the treatment of neuronal disorders, e.g. neuronal diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia, which comprises administering of a thereutically effective amount said compositions or combinations to a mammal, preferably a human.

Accordingly, the invention provides the use of these compositions or combinations for the preparation of a medicament for the treatment of neuronal disorders, e.g. neuronal diseases selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction and dementia.

The method comprises either co-administration of at least one QC inhibitor of formula 1 and at least one compound selected from the group consisting of PEP-inhibitors, LiCl, inhibitors of dipeptidyl aminopeptidases, preferably inhibitors of DP IV or DP IV-like enzymes, NPY-receptor ligands, NPY agonists, ACE inhibitors, PIMT enhancers, inhibitors of beta secretases, inhibitors of gamma secretases, inhibitors of neutral endopeptidase, inhibitors of PDE-4, MAO inhibitors, TNFalpha inhibitors, amyloid protein or amyloid peptide deposition inhibitors, sigma-1 receptor inhibitors and histamine H3 antagonists or the sequential administration thereof.

Co-administration includes administration of a formulation which includes at least one QC inhibitor of formula 1 and at least one compound selected from the group consisting of PEP-inhibitors, LiCl, inhibitors of dipeptidyl aminopeptidases, preferably inhibitors of DP IV or DP IV-like enzymes, NPY-receptor ligands, NPY agonists, ACE inhibitors, PIMT enhancers, inhibitors of beta secretases, inhibitors of gamma secretases, inhibitors of neutral endopeptidase, inhibitors of PDE-4, MAO inhibitors, TNFalpha inhibitors, amyloid protein or amyloid peptide deposition inhibitors, sigma-1 receptor inhibitors and histamine H3 antagonists or the essentially simultaneous administration of separate formulations of each agent.

Examples of Suitable PIMT Enhancers are 10-aminoaliphatyl-dibenz[b, f] oxepines of the general formula

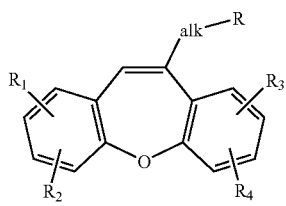

described in WO 98/15647 and WO 03/057204, respectively, wherein alk is a divalent aliphatic radical, R is an amino group that is unsubstituted or mono- or di-substituted by monovalent aliphatic and/or araliphatic radicals or disubstituted by divalent aliphatic radicals, and $R_1$, $R_2$, $R_3$ and $R_4$ are each, independently of the others, hydrogen, lower alkyl, lower alkoxy, halogen or trifluoromethyl.

Further useful according to the present invention are modulators of PIMT activity of the general formulae I-IV:

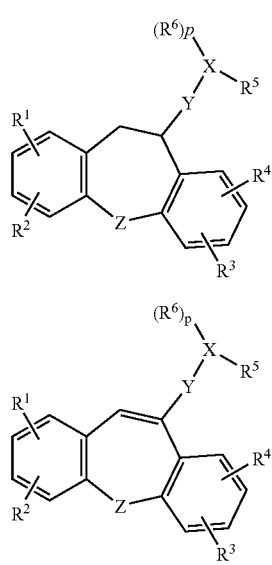

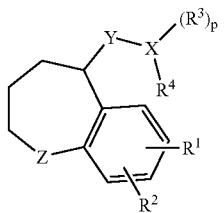

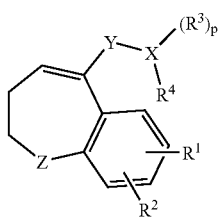

wherein the definition of the substituents $R^1$-$R^5$, $(R^3)p$, $(R^6)p$, X, Y and Z is described in WO 2004/039773.

WO 98/15647, WO 03/057204 and WO 2004/039773 are incorporated herein in their entirety and are part of this invention with regard to the synthesis and use of the compounds described therein.

Suitable inhibitors of beta and/or gamma secretases and compositions containing such inhibitors are described, e.g. in GB 2 385 124, GB 2 389 113, US 2002-115616, WO 01/87293, WO 03/057165, WO 2004/052348 and WO 2004/062652. These references are incorporated herein in their entirety and are part of this invention with regard to the synthesis, manufacture and use of the compounds and compositions described therein for the inhibition of beta and/or gamma secretases.

A potent selective and cell permeable gamma secretase inhibitor is (5S)-(t-Butoxycarbonylamino)-6-phenyl-(4R)hydroxy-(2R)benzylhexanoyl)-L-leu-L-phe-amide with the formula:

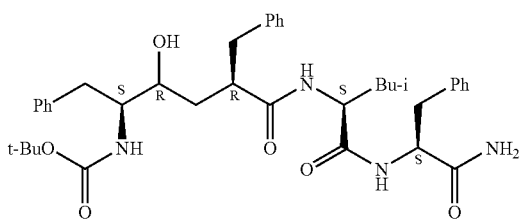

A potent beta secretase inhibitor is PNU-33312 of the formula

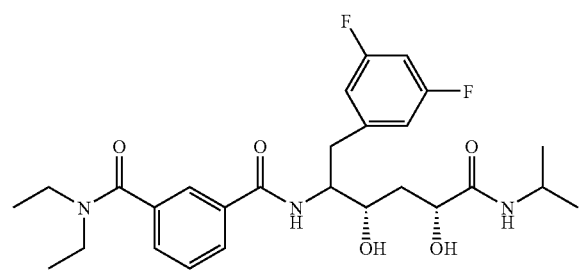

Suitable PDE-4 inhibitors are, e.g. shown in the table below:

| Company | Drug Code | Structure |
|---|---|---|
| Celgene Corp | CC-002 | |
| Celitech Group plc/ Merck Frosst | L-826141 | 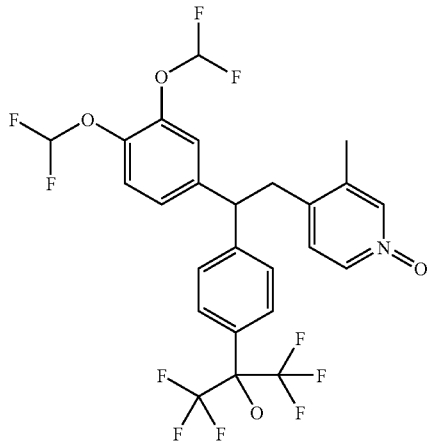 |
| Celitech Group plc | Sch-351591 (D-4396) | 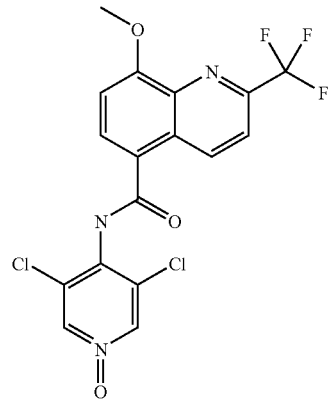 |
| Dainippon Pharmaceutical Co Ltd | OS-0217 | 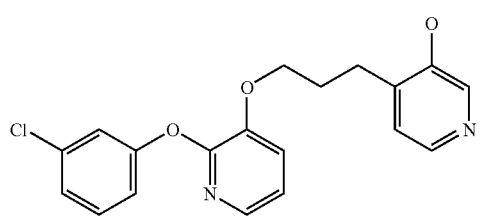 |
| IBFB Pharma GmbH | IBFB-130011<br>IBFB-150007<br>IBFB-130020<br>IBFB-140301 | |
| ICOS Corp | IC-485 | 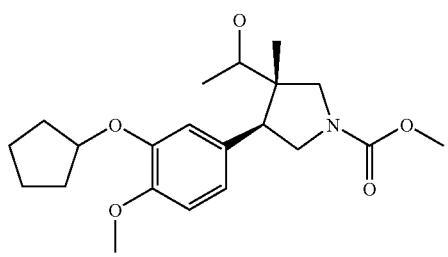 |

-continued
| Company | Drug Code | Structure |
|---|---|---|
| Kings College London | MX-554, MX-565 | |
| Memory Pharmaceuticals Corp | MEM-1414 MEM-1018 MEM-1091 MEM-1145 | |
| Pfizer Inc | CI-1044 | 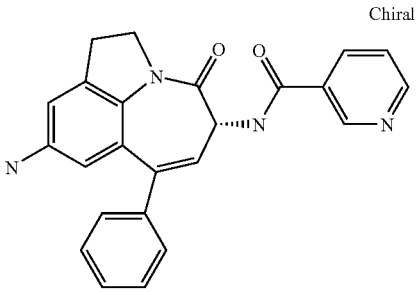 Chiral |
| Pfizer Inc | BHN | 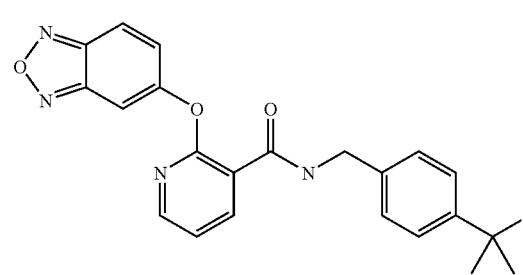 |
| Schering AG | ZK-117137 | 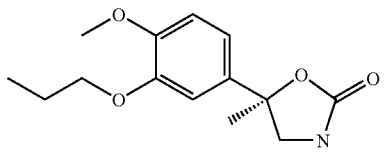 |
| SmithKline Beecham Pharmaceuticals | SB-207499 analogs, GSK | 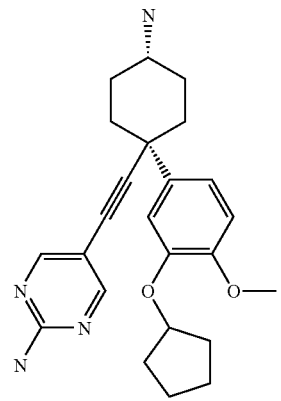 |
A preferred PDE-4-inhibitor is Rolipram.
A suitable MAO-inhibitor is the compound ladostigil of the formula
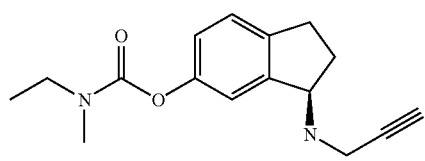

Suitable histamine H3 antagonists are, e.g. shown in the table below:

| Company | Drug | Structure |
| --- | --- | --- |
| Abbott Laboratories | A-331440 | |
| Abbott Laboratories | A-349821 | |
| Aventis Pharma AG | 3874-H1 | 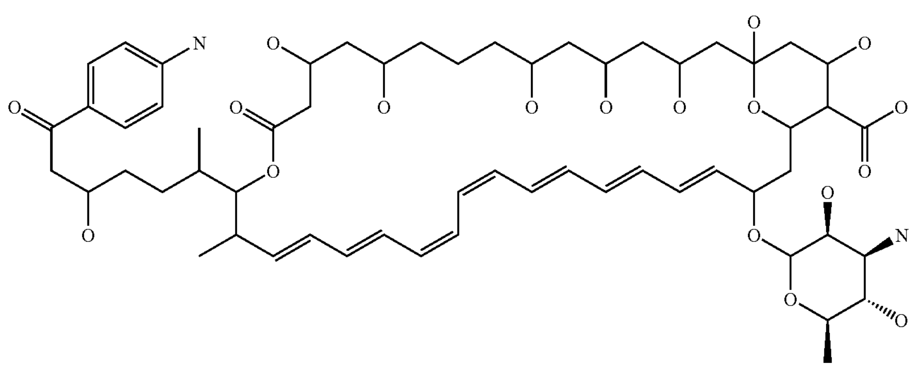 |
| Berlin Free University | UCL-2173 | 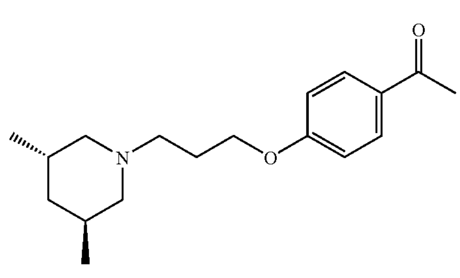 |

-continued

| Company | Drug | Structure |
|---|---|---|
| BioProjet, Societe Civile de Recherche | | |
| BioProjet, Societe Civile de Recherche | UCL-1470 | |
| Daewoong Pharmaceutical Co Ltd | DWP-302 | |
| GlaxoSmithKline Inc | GSK-189254A GSK-207040A | |
| Gliatech Inc | cipralisant | |
| Gliatech Inc | GT-2203 | |
| Hokkaido University | 1S,2S)-2-(2-Aminoethyl)-1-(1H-imidazol-4-yl)cyclopropane | 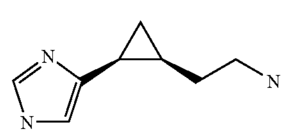 |
| Johnson & Johnson | JNJ-5207852 | |
| Novo Nordisk A/S | NNC-0038-0000-1049 | 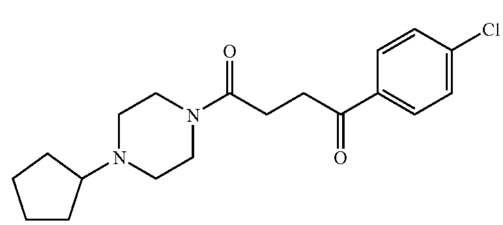 |

| Company | Drug | Structure |
|---|---|---|
| Schering-Plough Research Institute | dual H1/H3 antagonists | |
| Schering-Plough Research Institute | Sch-79687 | |

Suitable inhibitors of prolyl endopeptidase (PEP) are, e.g. chemical derivatives of proline or small peptides containing terminal prolines. Benzyloxycarbonyl-prolyl-prolinal has been shown to be a specific transition state inhibitor of the enzyme (Wilk, S. and Orloeski, M., J. Neurochem., 41, 69 (1983), Friedman, et al., Neurochem., 42, 237 (1984)). N-terminal substitutions of L-proline or L-prolylpyrrolidine (Atack, et al., Eur. J. of Pharm., 205, 157-163 (1991), JP 03 56,460, EP 384,341), as well as variations of N-benzyloxycarbonyl (Z) dipeptides containing prolinal at the carboxy terminus have been synthesized as prolyl endopeptidase inhibitors (Nishikata, et al., Chem. Pharm. Bull. 34(7), 2931-2936 (1986), Baker, A. et al., Bioorganic & Medicinal Chem. Letts., 1(11), 585-590 (1991)). Thioproline, thiazolidine, and oxopyrrolidine substitutions of the core structure have been reported to inhibit prolyl endopeptidase (Tsuru, et al., J. Biochem., 94, 1179 (1988), Tsuru, et al., J. Biochem., 104, 580-586 (1988), Saito et al., J. Enz. Inhib. 5, 51-75 (1991), Uchida, I., et al. PCT Int. Appl. WO 90 12,005, JP 03 56,461, JP 03 56,462). Similarly, various modifications of the carboxy terminal proline have been made, including various fluorinated ketone derivatives (Henning, EP 4,912, 127). General syntheses of fluorinated ketone derivatives has been described (Angelastro, M. R., et al., Tetrahedron Letters 33(23), 3265-3268 (1992)). Other compounds such as chloromethyl ketone derivatives of acyl-proline or acylpeptide-proline (Z-Gly-Pro-$CH_2$Cl) have been demonstrated to inhibit the enzyme by alkylating the enzyme's active site (Yoshimoto, T., et al., Biochemistry 16, 2942 (1977)).

EP-A-0 286 928 discloses 2-acylpyrrolidine derivatives useful as propyl endopeptidase inhibitors.

Further suitable prolyl endopeptidase inhibitors according to the present invention are, e.g. Fmoc-Ala-Pyrr-CN and those listed below:

| Z-321 | ONO-1603 |
|---|---|
| Zeria Pharmaceutical Co Ltd | Ono Pharmaceutical Co Ltd |
| (4R)-3-(indan-2-ylacetyl)-4-(1-pyrrolidinyl-carbonyl)-1,3-thiazolidin | (S)-1-[N-(4-chlorobenzyl)-succinamoyl]pyrrolidin-2-carbaldehyd |

-continued

| JTP-4819 | S-17092 |
|---|---|
| Japan Tobacco Inc | Servier |
| 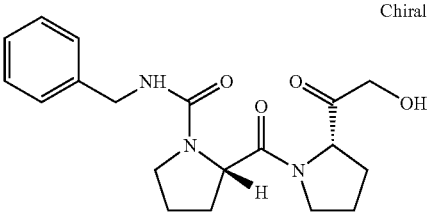 | 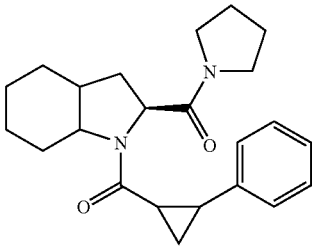 |
| (S)-2-{[(S).(hydroxyacatyl)-1-pyrrolidinyl] carbonyl}-N-(phenylmethyl)-1-pyrrolidin-carboxamid | (2S, 3aS, 7aS)-1{[(R,R)-2-phenylcyclopropyl] carbonyl}-2-[(thiazolidin-3-yl)carbonyl] octahydro-1H-indol |

Further suitable prolyl endopeptidase inhibitors according to the present invention are disclosed in JP 01042465, JP 03031298, JP 04208299, WO 0071144, U.S. Pat. No. 5,847, 155; JP 09040693, JP 10077300, JP 05331072, JP 05015314, WO 9515310, WO 9300361, EP 0556482, JP 06234693, JP 01068396, EP 0709373, U.S. Pat. No. 5,965, 556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506, 256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757, 083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 9118877, JP 04009367, JP 04235162, U.S. Pat. No. 5,407,950, WO 9501352, JP 01250370, JP 02207070, U.S. Pat. No. 5,221,752, EP 0468339, JP 04211648 and WO 9946272, the teachings of which are herein incorporated by reference in their entirety, especially concerning these inhibitors, their definition, uses and their production.

Most preferred is the PEP-inhibitor of the formula:

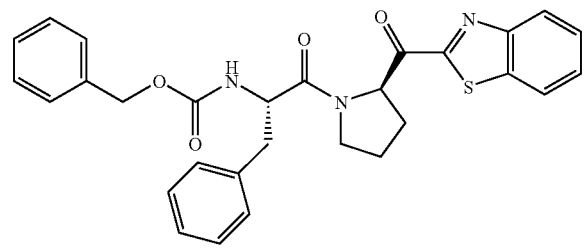

Other suitable compounds that can be used according to the present invention in combination with QC-inhibitors are NPY, a NPY mimetic or a NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 9417035, WO 9719911, WO 9719913, WO 9612489, WO 9719914, WO 9622305, WO 9640660, WO 9612490, WO 9709308, WO 9720820, WO 9720821, WO 9720822, WO 9720823, WO 9719682, WO 9725041, WO 9734843, WO 9746250, WO 9803492, WO 9803493, WO 9803494 and WO 9807420; WO 0030674, U.S. Pat. Nos. 5,552,411, 5,663,192 and 5,567,714; 6,114,336, Japanese patent application JP 09157253; international patent applications WO 9400486, WO 9312139, WO 9500161 and WO 9915498; U.S. Pat. No. 5,328,899; German patent application DE 393 97 97; European patent applications EP 355 794 and EP 355 793; and Japanese patent applications JP 06116284 and JP 07267988, the disclosures in all of which documents are hereby incorporated by reference. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 9417035, WO 9719911, WO 9719913, WO 9612489, WO 9719914, WO 9622305, WO 9640660, WO 9612490, WO 9709308, WO 9720820, WO 9720821, WO 9720822, WO 9720823, WO 9719682, WO 9725041, WO 9734843, WO 9746250, WO 9803492, WO 9803493, WO 9803494, WO 9807420 and WO 9915498; U.S. Pat. Nos. 5,552,411, 5,663, 192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds which may be mentioned include those disclosed in international patent applications WO 9417035, WO 9719911, WO 9719913, WO 9719914 or, preferably, WO 9915498. Preferred amino acid-based NPY antagonists include those that are specifically disclosed in these patent documents, for example BIBP3226 and, especially, (R)-N2-(diphenylacetyl)-(R)-N-[1-(4-hydroxy-phenyl) ethyl] arginine amide (Example 4 of international patent application WO 9915498).

For the avoidance of doubt, the examples disclosed in each of the above mentioned publications are specifically incorporated herein by reference in their entirety, as individually disclosed compounds, especially concerning their structure, their definition, uses and their production.

Suitable DP IV-inhibitors are those, disclosed e.g. in U.S. Pat. No. 6,380,398, U.S. Pat. No. 6,011,155; U.S. Pat. No. 6,107,317; U.S. Pat. No. 6,110,949; U.S. Pat. No. 6,124,305; U.S. Pat. No. 6,172,081; WO 9515309, WO 9961431, WO 9967278, WO 9967279, DE 198 34 591, WO 9740832, DE 196 16 486 C 2, WO 9819998, WO 0007617, WO 9938501, WO 9946272, WO 9938501, WO 0168603, WO 0140180, WO 0181337, WO 0181304, WO 0155105, WO 0202560 and WO 0214271, WO 0204610, WO 02051836, WO 02068420, WO 02076450; WO 02083128, WO 0238541, WO 03000180, WO 03000181, WO 03000250, WO 03002530, WO 03002531, WO 03002553, WO 03002593, WO 03004496, WO 03004498, WO 03024965, WO 03024942, WO 03035067, WO 03037327, WO 03035057, WO 03045977, WO 03055881, WO 0368748, WO 0368757, WO 03057666, WO 03057144, WO 03040174, WO 03033524 and WO 03074500, the teachings of which are herein incorporated by reference in their entirety, especially concerning these inhibitors, their definition, uses and their production.

Further suitable DP IV-inhibitors are, e.g. shown in the table below:

| Company | Drug Code | Structure |
| --- | --- | --- |
| Bristol-Myers Squibb Co | BMS-477118 | 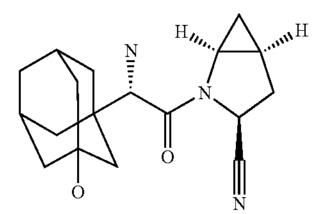 |
| Eisai Co Ltd | | 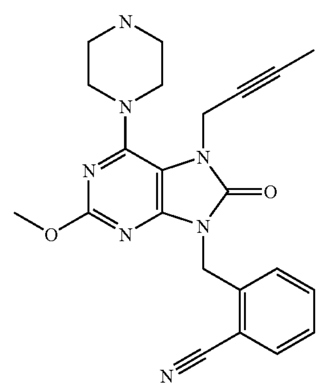 |
| Ferring Research Ltd | FE-999011 | 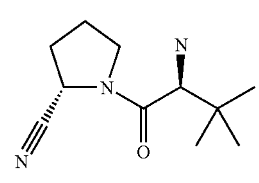 |
| GlaxoSmithKline plc | GW-229A | 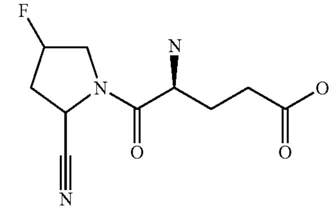 |

-continued
| Company | Drug Code | Structure |
|---|---|---|
| Kyowa Hakko Kogyo | K-579 | 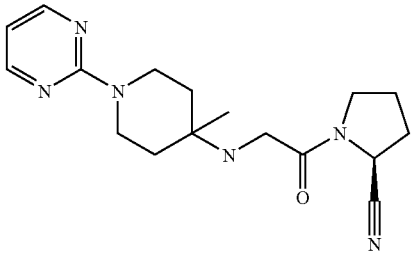 |
| Merck & Co Inc | MK-431 | 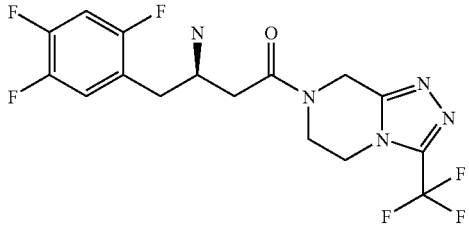 |
| Novartis AG | LAF-237 | 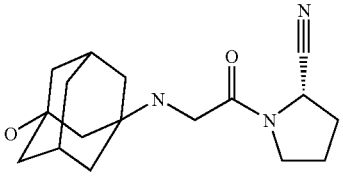 |
| Novo Nordisk A/S | | 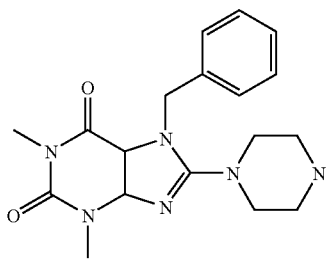 |
| Novo Nordisk A/S | Valine pyrrolidine | |
| Pfizer Inc | CP-867534-01 | 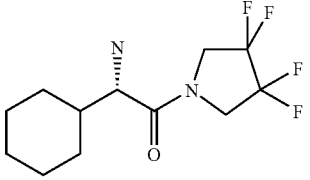 |
| Phenomix Corp. | PHX-1004 | |
| Point Therapeutics Inc. | PT-100 (Talabostat) | 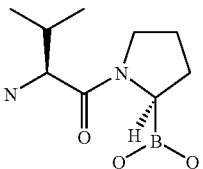 |
| Sanofi-Synthelabo | SSR-162369 | |
| Syrrx Inc | SYR-322 | |

| Company | Drug Code | Structure |
|---|---|---|
| Taisho Pharmaceutical Co Ltd | | 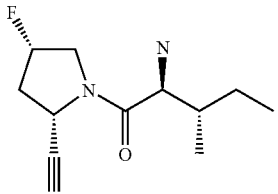 |
| Tanabe Seiyaku Co Ltd | TSL-225 | 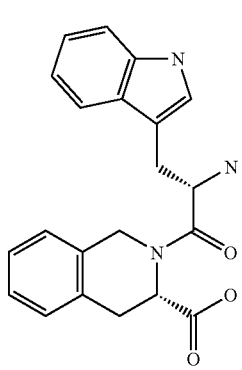 |
| Tanabe Seiyaku Co Ltd., licensed to GlaxoSmithKline plc | 815541 (T-6666) | |

For the avoidance of doubt, the references and examples disclosed herein are specifically incorporated herein by reference in their entirety, or as individually disclosed compounds, especially concerning their structure, their definition, uses and their production.

Preferred DP IV-inhibitors are dipeptide-like compounds and compounds analogous to dipeptide compounds that are formed from an amino acid and a thiazolidine or pyrrolidine group, and salts thereof, referred to hereinafter as dipeptide-like compounds. Preferably the amino acid and the thiazolidine or pyrrolidine group are bonded with an amide bond.

Especially suitable for that purpose according to the invention are dipeptide-like compounds in which the amino acid is preferably selected from a natural amino acid, such as, for example, leucine, valine, glutamine, glutamic acid, proline, isoleucine, asparagines and aspartic acid.

The dipeptide-like compounds used according to the invention exhibit at a concentration (of dipeptide compounds) of 10 µM, a reduction in the activity of plasma dipeptidyl peptidase IV or DP IV-analogous enzyme activities of at least 10%, especially of at least 40%. Frequently a reduction in activity of at least 60% or at least 70% is also required. Preferred agents may also exhibit a reduction in activity of a maximum of 20% or 30%.

Preferred dipeptide-like compounds are N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof.

Further preferred compounds are given in Table 2.

The salts of the dipeptide-like compounds can be present in a molar ratio of dipeptide (-analogous) component to salt component of 1:1 or 2:1. Such a salt is, for example, (Ile-Thia)$_2$ fumaric acid.

TABLE 2

Structures of further preferred dipeptide compounds DP IV-inhibitor

H-Asn-pyrrolidine
H-Asn-thiazolidine
H-Asp-pyrrolidine
H-Asp-thiazolidine
H-Asp(NHOH)-pyrrolidine
H-Asp(NHOH)-thiazolidine
H-Glu-pyrrolidine
H-Glu-thiazolidine
H-Glu(NHOH)-pyrrolidine
H-Glu(NHOH)-thiazolidine
H-His-pyrrolidine
H-His-thiazolidine
H-Pro-pyrrolidine
H-Pro-thiazolidine
H-Ile-azididine
H-Ile-pyrrolidine
H-L-allo-Ile-thiazolidine
H-Val-pyrrolidine
H-Val-thiazolidine In another preferred embodiment, the present invention provides the use of compounds of formula 3 for competitive modulation of dipeptidyl peptidase IV catalysis:

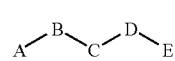 (3)

wherein

A, B, C, D and E are independently any amino acid moieties including proteinogenic amino acids, non-proteinogenic amino acids, L-amino acids and D-amino acids and wherein E and/or D may be absent.

According to preferred embodiments, the residues A, B, C, D and E of formula (3) are independently defined as follows:

A is an amino acid except a D-amino acid,

B is an amino acid selected from Pro, Ala, Ser, Gly, Hyp, acetidine-(2)-carboxylic acid and pipecolic acid, C is any amino acid except Pro, Hyp, acetidine-(2)-carboxylic acid, pipecolic acid and except N-alkylated amino acids, e.g. N-methyl valine and sarcosine, D is any amino acid or missing, and E is any amino acid or missing, or:

C is any amino acid except Pro, Hyp, acetidine-(2)-carboxylic acid, pipecolic acid, except N-alkylated amino acids, e.g. N-methyl valine and sarcosine, and except a D-amino-acid;

D is any amino acid selected from Pro, Ala, Ser, Gly, Hyp, acetidine-(2)-carboxylic acid and pipecolic acid, and E is any amino acid except Pro, Hyp, acetidine-(2)-carboxylic acid, pipecolic acid and except N-alkylated amino acids, e.g. N-methyl valine and sarcosine.

Other amino acids than those encoded in the genetic code can also be included in peptide compounds within the scope of the invention and can be classified within this general scheme.

Proteinogenic amino acids are defined herein as natural protein-derived α-amino acids. Non-proteinogenic amino acids are defined herein as all other amino acids, which are not building blocks of common natural proteins.

The resulting peptides may be synthesized as the free C-terminal acid or as the C-terminal amide form. The free acid peptides or the amides may be varied by side chain modifications. Such side chain modifications include for instance, but are not restricted to, homoserine formation, pyroglutamic acid formation, disulphide bond formation, deamidation of asparagine or glutamine residues, methylation, t-butylation, t-butyloxycarbonylation, 4-methylbenzylation, thioanysilation, thiocresylation, benzyloxymethylation, 4-nitrophenylation, benzyloxycarbonylation, 2-nitrobencoylation, 2-nitrosulphenylation, 4-toluenesulphonylation, pentafluorophenylation, diphenylmethylation, 2-chlorobenzyloxycarbonylation, 2,4,5-trichlorophenylation, 2-bromobenzyloxycarbonylation, 9-fluorenylmethyloxycarbonylation, triphenylmethylation, 2,2,5,7,8,-pentamethylchroman-6-sulphonylation, hydroxylation, oxidation of methionine, formylation, acetylation, anisylation, benzylation, bencoylation, trifluoroacetylation, carboxylation of aspartic acid or glutamic acid, phosphorylation, sulphation, cysteinylation, glycolysation with pentoses, deoxyhexoses, hexosamines, hexoses or N-acetylhexosamines, farnesylation, myristolysation, biotinylation, palmitoylation, stearoylation, geranylgeranylation, glutathionylation, 5'-adenosylation, ADP-ribosylation, modification with N-glycolylneuraminic acid, N-acetylneuraminic acid, pyridoxal phosphate, lipoic acid, 4'-phosphopantetheine, or N-hydroxysuccinimide.

In the compounds of formula (3), the amino acid moieties A, B, C, D, and E are respectively attached to the adjacent moiety by amide bonds in a usual manner according to standard nomenclature so that the amino-terminus (N-terminus) of the amino acids (peptide) is drawn on the left and the carboxyl-terminus of the amino acids (peptide) is drawn on the right. (C-terminus).

Preferred peptide compounds are listed in table 3.

TABLE 3

Examples of peptide substrates

| Peptide | Mass (calc.) | Mass (exp.)[1] [M + H+] |
|---|---|---|
| 2-Amino octanoic acid-Pro-Ile | 369.5 | 370.2 |
| Abu-Pro-Ile | 313.4 | 314.0 |
| Aib-Pro-Ile | 313.4 | 314.0 |
| Aze-Pro-Ile | 311.4 | 312.4 |
| Cha-Pro-Ile | 381.52 | 382.0 |
| Ile-Hyp-Ile | 356.45 | 358.2 |
| Ile-Pro-allo-Ile | 341.4 | 342.0 |
| Ile-Pro-t-butyl-Gly | 341.47 | 342.36 |
| Ile-Pro-Val | 327.43 | 328.5 |
| Nle-Pro-Ile | 341.45 | 342.2 |
| Nva-Pro-Ile | 327.43 | 328.2 |
| Orn-Pro-Ile | 342.42 | 343.1 |
| Phe-Pro-Ile | 375.47 | 376.2 |
| Phg-Pro-Ile | 361.44 | 362.2 |
| Pip-Pro-Ile | 338.56 | 340.0 |
| Ser(Bzl)-Pro-Ile | 405.49 | 406.0 |
| Ser(P)-Pro-Ile | 395.37 | 396.0 |
| Ser-Pro-Ile | 315.37 | 316.3 |
| t-butyl-Gly-Pro-D-Val | 327.4 | 328.6 |
| t-butyl-Gly-Pro-Gly | 285.4 | 286.3 |
| t-butyl-Gly-Pro-Ile | 341.47 | 342.1 |
| t-butyl-Gly-Pro-Ile-amide | 340.47 | 341.3 |
| t-butyl-Gly-Pro-t-butyl-Gly | 341.24 | 342.5 |
| t-butyl-Gly-Pro-Val | 327.4 | 328.4 |
| Thr-Pro-Ile | 329.4 | 330.0 |
| Tic-Pro-Ile | 387.46 | 388.0 |
| Trp-Pro-Ile | 414.51 | 415.2 |
| Tyr(P)-Pro-Ile | 471.47 | 472.3 |
| Tyr-Pro-allo-Ile | 391.5 | 392.0 |
| Val-Pro-allo-Ile | 327.4 | 328.5 |
| Val-Pro-t-butyl-Gly | 327.4 | 328.15 |
| Val-Pro-Val | 313.4 | 314.0 |

[1][M + H+] were determined by Electrospray mass spectrometry in positive ionization mode.

t-butyl-Gly is defined as:

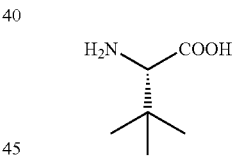

Ser(Bzl) and Ser(P) are defined as benzyl-serine and phosphoryl-serine, respectively. Tyr(P) is defined as phosphoryl-tyrosine.

Further preferred DP IV-inhibitors, which can be used according to the present invention, are peptidylketones of formula 4:

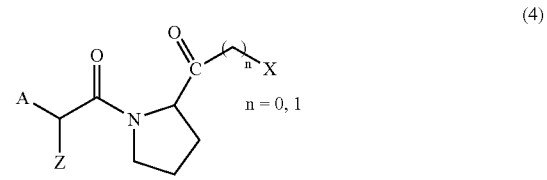

(4)

and pharmaceutically acceptables salts thereof, wherein:

A is selected from the following structures:

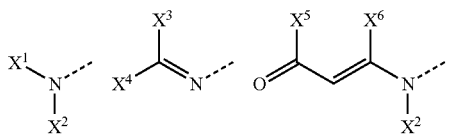

wherein
$X^1$ is H or an acyl or oxycarbonyl group including an amino acid residue, N-protected amino acid residue, a peptide residue or a N-protected peptide residue, $X^2$ is H, —$(CH)_m$—NH—$C_5H_3N$—Y with m=2-4 or —$C_5H_3N$—Y (a divalent pyridyl residue) and Y is selected from H, Br, Cl, I, $NO_2$ or CN, $X^3$ is H or selected from an alkyl-, alkoxy-, halogen-, nitro-, cyano- or carboxy-substituted phenyl or from an alky-, alkoxy-, halogen-, nitro-, cyano- or carboxy-substituted pyridyl residue, $X^4$ is H or selected from an alkyl-, alkoxy-, halogen-, nitro-, cyano- or carboxy-substituted phenyl or from an alkyl-, alkoxy-, halogen-, nitro-, cyano- or carboxy-substituted pyridyl residue, $X^5$ is H or an alkyl, alkoxy or phenyl residue,
$X^6$ is H or an alkyl residue,
for n=1
X is selected from: H, $OR^2$, $SR^2$, $NR^2R^3$, $N^+R^2R^3R^4$, wherein:
$R^2$ stands for acyl residues, which are optionally substituted with alkyl, cycloalkyl, aryl or heteroaryl residues, or for amino acid residues or peptidic residues, or alkyl or hetetoaryl residues,
$R^3$ stands for alkyl or acyl residues, wherein $R^2$ and $R^3$ may be part of a saturated or unsaturated carbocyclic or heterocyclic ring,
$R^4$ stands for alkyl residues, wherein $R^2$ and $R^4$ and or $R^3$ and $R^4$ may be part of a saturated or unsaturated carbocyclic or heterocyclic ring,
for n=0
X is selected from:

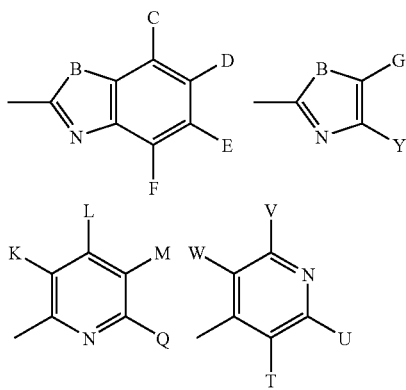

wherein
B stands for: O, S or $NR^5$, wherein $R^5$ is H, alkyl or acyl,
C, D, E, F, G, Y, K, L, M, Q, T, U, V and W are independently selected from alkyl and substituted alkyl residues, oxyalkyl, thioalkyl, aminoalkyl, carbonylalkyl, acyl, carbamoyl, aryl and heteroalkyl residues, and Z is selected from H, or a branched or straight chain alkyl residues from $C_1$-$C_9$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

In preferred compounds of formula 4, A is

wherein
$X^1$ is H or an acyl or oxycarbonyl group including an amino acid residue, N-acylated amino acid residue, a peptide residue from di- to pentapeptides, preferably a dipeptide residue, or a N-protected peptide residue from di- to pentapeptides, preferably a N-protected dipeptide residue $X^2$ is H, —$(CH)_m$—NH—$C_5H_3N$—Y with m=2-4 or —$C_5H_3N$—Y (a divalent pyridyl residue) and Y is selected from H, Br, Cl, I, $NO_2$ or CN, for n=1
X is preferably selected from: H, $OR^2$, $SR^2$, $NR^2R^3$, wherein:
$R^2$ stands for acyl residues, which are optionally substituted with alkyl, cycloalkyl, aryl or heteroaryl residues, or for amino acid residues or peptidic residues, or alkyl residues, which are optionally substituted with alkyl, cycloalkyl, aryl or heteroaryl residues,
$R^3$ stands for alkyl or acyl residues, wherein $R^2$ and $R^3$ may be part of a saturated or unsaturated carbocyclic or heterocyclic ring,
for n=0
X is preferably selected from:

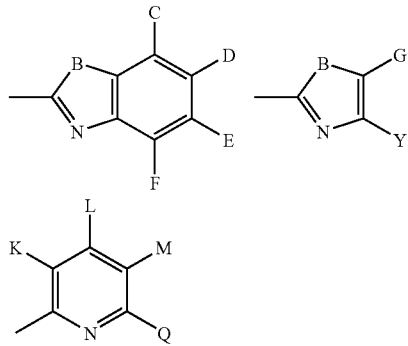

wherein
B stands for: O, S or $NR^5$, wherein $R^5$ is H, alkyl or acyl,
C, D, E, F, G, Y, K, L, M and Q are independently selected from alkyl and substituted alkyl residues, oxyalkyl, thioalkyl, aminoalkyl, carbonylalkyl, acyl, carbamoyl, aryl and heteroaryl residues, and Z is selected from H, or a branched or straight chain alkyl residue from $C_1$-$C_9$, preferably $C_2$-$C_6$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

In more preferred compounds of formula 4, A is

wherein
- $X^1$ is H or an acyl or oxycarbonyl group including an amino acid residue, N-acylated amino acid residue or a peptide residue from di- to pentapeptides, preferably a dipeptide residue, or a N-protected peptide residue from di- to pentapeptides, preferably a N-protected dipeptide residue
for n=1,
X is preferably selected from: H, $OR^2$, $SR^2$, wherein:
- $R^2$ stands for acyl residues, which are optionally substituted with alkyl or aryl residues,
for n=0
X is preferably selected from:

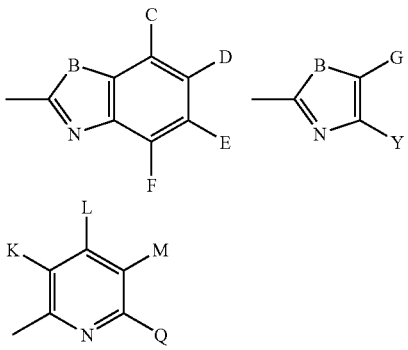

wherein
B stands for: O, S or $NR^5$, wherein $R^5$ is H, alkyl or acyl,
C, D, E, F, G, Y, K, L, M and Q are independently selected from alkyl and substituted alkyl residues, oxyalkyl, thioalkyl, aminoalkyl, carbonylalkyl, acyl, carbamoyl, aryl and heteroaryl residues, and
Z is selected from H, or a branched or straight chain alkyl residue from $C_1$-$C_9$, preferably $C_2$-$C_6$, a branched or straight chain alkenyl residue from $C_2$-$C_9$, a cycloalkyl residue from $C_3$-$C_8$, a cycloalkenyl residue from $C_5$-$C_7$, an aryl or heteroaryl residue, or a side chain selected from all side chains of all natural amino acids or derivatives thereof.

In most preferred compounds of formula 4, A is

wherein
- $X^1$ is H or an acyl or oxycarbonyl group including an amino acid residue, N-acylated amino acid residue or a dipeptide residue, containing a Pro or Ala in the penultimate position, or a N-protected dipeptide residue containing a Pro or Ala in the penultimate position,
for n=1,
X is H,
for n=0
X is preferably selected from:

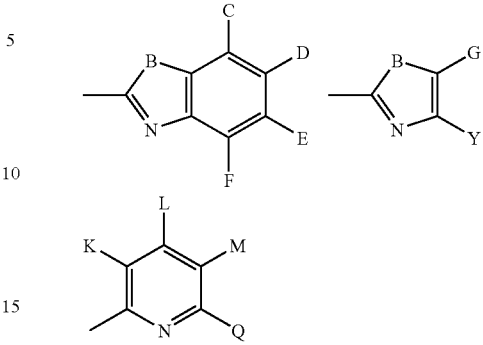

wherein
B stands for: O or S, most preferably for S
C, D, E, F, G, Y, K, L, M, Q, are H and
Z is selected from H, or a branched or straight chain alkyl residue from $C_3$-$C_5$, a branched or straight chain alkenyl residue from $C_2$-$C_9$, a cycloalkyl residue from $C_5$-$C_7$, a cycloalkenyl residue from $C_5$-$C_7$, an aryl or heteroaryl residue, or a side chain selected from all side chains of all natural amino acids or derivatives thereof. Most preferred for Z is H.

According to a preferred embodiment the acyl groups are $C_1$-$C_6$-acyl groups.

According to a further preferred embodiment the alk(yl) groups are $C_1$-$C_6$-alk(yl) groups, which may be branched or unbranched.

According to a still further preferred embodiment the alkoxy groups are $C_1$-$C_6$-alkoxy groups.

According to yet another preferred embodiment the aryl residues are $C_5$-$C_{12}$ aryl residues that have optionally fused rings.

According to a still further preferred embodiment the cycloalkyl residues (carbocycles) are $C_3$-$C_8$-cycloalkyl residues.

According to another preferred embodiment the heteroaryl residues are $C_4$-$C_{11}$ aryl residues that have optionally fused rings and, in at least one ring, additionally from 1 to 4 preferably 1 or 2 hetero atoms, such as O, N and/or S.

According to a further preferred embodiment peptide residues contain from 2 to 50 amino acids.

According to another preferred embodiment the heterocyclic residues are $C_2$-$C_7$-cycloalkyl radicals that additionally have from 1 to 4, preferably 1 or 2 hetero atoms, such as O, N and/or S.

According to a still further preferred embodiment the carboxy groups are $C_1$-$C_6$ carboxy groups, which may be branched or unbranched.

According to yet another preferred embodiment the oxycarbonyl groups are groups of the formula —O—$(CH_2)_{1-6}$COOH.

The amino acids can be any natural or synthetic amino acid, preferably natural alpha amino acids.

Preferred compounds of formula (4) are 2-Methylcarbonyl-1-N-[(L)-Alanyl-(L)-Valinyl]-(2S)-pyrrolidine hydrobromide; 2-Methyl)carbonyl-1-N-[(L)-Valinyl-(L)-Prolyl-(L)-Valinyl]-(2S)-pyrrolidine hydrobromide; 2-[(Acetyl-oxy-methyl)carbonyl]-1-N-[(L)-Alanyl-(L)-Valinyl]-(2S)-pyrrolidine hydrobromide; 2-[Benzoyl-oxy-methyl)

carbonyl]-1-N-[{(L)-Alanyl}-(L)-Valinyl]-(2S)-pyrrolidine hydrobromide; 2-{[(2,6-Dichlorbenzyl)thiomethyl]carbonyl}-1-N-[{(L)-Alanyl}-(L)-Valinyl]-(2S)-pyrrolidine; 2-[Benzoy-loxy-methyl)carbonyl]-1-N-[Glycyl-(L)-Valinyl]-(2S)-pyrrolidine hydrobromide; 2-[([1,3]-thiazole-2-yl) carbonyl]-1-N-[{(L)-Alanyl}-(L)-Valinyl]-(2S)-pyrrolidine trifluoracetat; 2-[(benzothiazole-2-yl)carbonyl]-1-N-[N-{(L)-Alanyl}-(L)-Valinyl]-(2S)-pyrrolidin trifluoracetat; 2-[(-benzothiazole-2-yl)carbonyl]-1-N-[{(L)-Alanyl}-Glycyl]-(2S)-pyrrolidine trifluoracetat; 2-[(pyridin-2-yl)carbonyl]-1-N-[N-{(L)-Alanyl}-(L)-Valinyl]-(2S)-pyrrolidine trifluoracetat.

Further, according to the present invention preferred DP IV-inhibitors are compounds of formula (5) including all stereoisomers and pharmaceutical acceptable salts:

$$B-(CH-R^1)_n-C(=X^2)-D \quad (5)$$

wherein n is 0 or 1, $R^1$ stands for H, $C_1$-$C_9$ branched or straight chain alkyl, preferably H, n-butan-2-yl, n-prop-2-yl or isobutyl, $C_2$-$C_9$ branched or straight chain alkenyl, $C_3$-$C_8$ cycloalkyl, preferably cyclohexyl, $C_5$-$C_7$ cycloalkenyl, aryl, heteroaryl or a side chain of a natural amino acid or mimetics thereof, $X^2$ stands for O, $NR^6$, $N^+(R^7)_2$, or S, B is selected from the following groups:

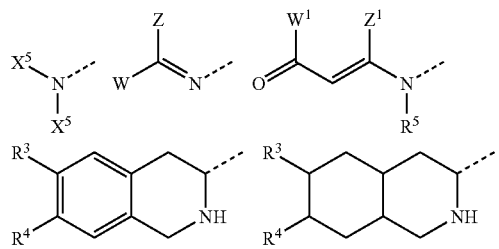

where $X^5$ is H or an acyl or oxycarbonyl group including amino acids, $R^5$ is H, $C_1$-$C_9$ branched or straight chain alkyl, preferably H, n-butan-2-yl, n-prop-2-yl or isobutyl, $C_2$-$C_9$ branched or straight chain alkenyl, $C_3$-$C_8$ cycloalkyl, preferably cyclohexyl, 3-hydroxyadamant-1-yl, $C_5$-$C_7$ cycloalkenyl, aryl, heteroaryl or a side chain of a natural amino acid or derivatives thereof, or a group of the formula —$(CH)_m$—NH—$C_5H_3N$—Y where m is an integer of 2-4, —$C_5H_3N$—Y is a divalent pyridyl moiety and Y is a hydrogen atom, a halogen atom, a nitro group or a cyano group, $R^6$, $R^7$ and $R^8$ are independently selected from H, optionally substituted $C_1$-$C_9$ branched or straight chain alkyl, preferably an optionally substituted $C_2$-$C_5$ branched or straight chain alkyl; or optionally substituted $C_2$-$C_9$ branched or straight chain alkenyl, preferably an $C_2$-$C_5$ branched or straight chain alkenyl; or optionally substituted $C_3$-$C_8$ cycloalkyl, preferably an optionally substituted $C_4$-$C_7$ cycloalkyl; or an optionally substituted $C_5$-$C_7$ cycloalkenyl, or an optionally substituted aryl residue, Z is selected from H, pyridyl or optionally substituted phenyl, optionally substituted alkyl groups, alkoxy groups, halogens, nitro, cyano and carboxy groups, W is selected from H, pyridyl or optionally substituted phenyl, optionally substituted alkyl groups, alkoxy groups, halogens, nitro, cyano and carboxy groups, $W^1$ is H or optionally substituted alkyl, alkoxy or optionally substituted phenyl, and $Z^1$ is H, or optionally substituted alkyl, $R^3$ and $R^4$ are independently H, hydroxy, alkyl, alkoxy, aralkoxy, nitro, cyano or halogen, D is an optionally substituted compound of the formula

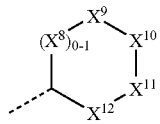

which can be saturated, or can have one, two or three double bonds, wherein $X^8$ to $X^{11}$ are independently CH, N, $N^+(R^7)$, or $CR^8$, if unsaturated, or $X^8$ to $X^{11}$ are independently $CH_2$, NH, $NH^+(R^7)$, O, or S if saturated, $X^{12}$ is CHA, NA, $CH_2$, NH, $NH^+(R^7)$, or $CHR^8$, if saturated or $X^{12}$ is CA, $NA^+$, CH, N, $N^+(R^7)$, or $CR^8$, if unsaturated and A is H or an isoster of a carboxylic acid such as CN, $SO_3H$, CONOH, $PO_3R^5R^6$, a tetrazole, an amide, an ester or an acid anhydride.

Throughout the application, D contains preferably at most two, further preferred at most one hetero atom in the ring.

According to preferred embodiments of the present invention, D stands for optionally substituted $C_4$-$C_7$ cycloalkyl, preferably $C_4$-$C_6$ cycloalkyl, optionally substituted $C_4$-$C_7$ cycloalkenyl, or optionally substituted (hetero)cycloalkyl of the formulae

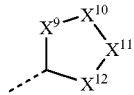

wherein the residues are as defined above, or

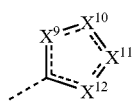

that is, a five-membered ring containing one or two double bonds in the ring, wherein the residues are as defined above, or

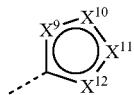

wherein the residues are as defined above,
or

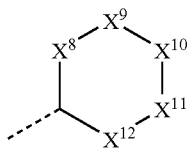

wherein the residues are as defined above,
or

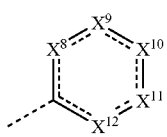

that is a six-membered ring containing one or two double bonds in the ring,
wherein the residues are as defined above,
or

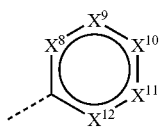

wherein the residues are as defined above.

According to a preferred embodiment, B has the following formula:

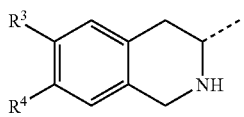

wherein the residues are as defined above.

According to another preferred embodiment, B has the following formula:

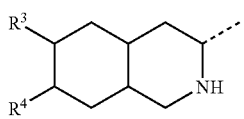

wherein the residues are as defined above.

Preferred compounds according to formula (5) are
1-cyclopentyl-3-methyl-1-oxo-2-pentanaminium chloride,
1-cyclopentyl-3-methyl-1-oxo-2-butanaminium chloride,
1-cyclopentyl-3,3-dimethyl-1-oxo-2-butanaminium chloride,
1-cyclohexyl-3,3-dimethyl-1-oxo-2-butanaminium chloride,
3-(cyclopentylcarbonyl)-1,2,3,4-tetrahydroisoquinolinium chloride, and
N-(2-cyclopentyl-2-oxoethyl)cyclohexanaminium chloride.

Because of the wide distribution of the protein in the body and the wide variety of mechanisms involving DP IV, DP IV-activity and DP IV-related proteins, systemic therapy (enteral or parenteral administration) with DP IV-inhibitors can result in a series of undesirable side-effects.

The problem to be solved was therefore moreover, to provide DP IV-inhibitors that can be used in combination therapy of neuronal diseases, for targeted influencing of locally limited patho-physiological and physiological processes. The problem of the invention especially consists in obtaining locally limited and highly specific inhibition of DP IV or DP IV-analogous activity for the purpose of targeted intervention in the regulation of the activity of locally active substrates.

This problem is solved according to the invention by the use of the DP IV-inhibitors of the general formula (6):

wherein
A is an amino acid having at least one functional group in the side chain,
B is a chemical compound covalently bound to at least one functional group of the side chain of A,
C is a thiazolidine, pyrrolidine, cyanopyrrolidine, hydroxyproline, dehydroproline or piperidine group amide-bonded to A.

In accordance with a preferred embodiment of the invention, pharmaceutical compositions are used comprising at least one compound of the general formula (5) and at least one customary adjuvant appropriate for the site of action.

Preferably A is an α-amino acid, especially a natural α-amino acid having one, two or more functional groups in the side chain, preferably threonine, tyrosine, serine, arginine, lysine, aspartic acid, glutamic acid or cysteine.

Preferably B is an oligopeptide having a chain length of up to 20 amino acids, a polyethylene glycol having a molar mass of up to 20 000 g/mol, an optionally substituted organic amine, amide, alcohol, acid or aromatic compound having from 8 to 50 C atoms.

Despite an extended side chain function, the compounds of formula (6) can still bind to the active centre of the enzyme dipeptidyl peptidase IV and analogous enzymes but are no longer actively transported by the peptide transporter PepT1. The resulting reduced or greatly restricted transportability of the compounds according to the invention leads to local or site directed inhibition of DP IV and DP IV-like enzyme activity.

By extending/expanding the side chain modifications, for example beyond a number of seven carbon atoms, it is accordingly possible to obtain a dramatic reduction in transportability. With increasing spatial size of the side chains, there is a reduction in the transportability of the substances. By spatially and sterically expanding the side chains, for example beyond the atom group size of a monosubstituted phenyl radical, hydroxylamine radical or amino acid residue, it is possible according to the invention to modify or suppress the transportability of the target substances.

Preferred compounds of formula (6) are compounds, wherein the oligopeptides have chain lengths of from 3 to 15, especially from 4 to 10, amino acids, and/or the polyethylene glycols have molar masses of at least 250 g/mol, preferably of at least 1500 g/mol and up to 15 000 g/mol, and/or the optionally substituted organic amines, amides, alcohols, acids or aromatic compounds have at least 12 C atoms and preferably up to 30 C atoms.

Pharmaceutical Compositions

To prepare the pharmaceutical compositions of this invention, at least one effector of QC optionally in combination with at least one PEP-inhibitor and/or at least one DP IV-inhibitor and/or at least one NPY-receptor-ligand and/or at least one ACE-inhibitor, can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds of the present invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using conventional methods known from the art.

The method of treating neuronal disorders as described in the present invention, may also be carried out using a pharmaceutical composition comprising at least one effector of QC optionally in combination with at least one PEP-inhibitor and/or at least one DP IV-inhibitor and/or at least one NPY-receptor-ligand and/or at least one ACE-inhibitor or any other of the compounds as defined herein and a pharmaceutically acceptable carrier. The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

Suitably, the particularly beneficial effect provided by the treatment of the invention is an improved therapeutic ratio for the combination of the invention relative to the therapeutic ratio for one compound of the combination when used alone and at a dose providing an equivalent efficacy to the combination of the invention.

In a preferred aspect, the particularly beneficial effect provided by the treatment of the invention is indicated to be a synergistic effect relative to the control expected from the effects of the individual active agents.

In a further aspect of the invention, combining doses of at least one QC-inhibitor with at least one PEP-inhibitor and/or at least one DP IV-inhibitor and/or at least one NPY-receptor-ligand will produce a greater beneficial effect than can be achieved for either agent alone at a dose twice that used for that agent in the combination.

In a preferred aspect, the dosage level of each of the active agents when used in accordance with the treatment of the invention will be less than would have been required from a purely additive effect upon the neuronal condition.

It is also considered that the treatment of the invention will effect an improvement, relative to the individual agents, in decreasing the intracellular deposition of pGlu-amyloid-β-peptides and thereby dramatically slowing down the plaque formation in the brain of a mammal, preferably in human brain.

In a further aspect, the invention also provides a process for preparing a pharmaceutical composition comprising at least one at least one effector of QC optionally in combination with at least one PEP-inhibitor and/or at least one DP IV-inhibitor and/or at least one NPY-receptor-ligand and/or at least one ACE-inhibitor and a pharmaceutically acceptable carrier therefor, which process comprises admixing the QC effector and/or DP IV-inhibitor and/or the PEP-inhibitor and/or the NPY-receptor-ligand and/or the ACE-inhibitor and a pharmaceutically acceptable carrier.

The compositions are preferably in a unit dosage form in an amount appropriate for the relevant daily dosage.

Suitable dosages, including especially unit dosages, of the QC-inhibitor, the PEP-inhibitor, the DP IV-inhibitor and the NPY-receptor-ligand include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES OF THE INVENTION

Example 1

Solid-Phase Synthesis of Peptides

The peptides used herein were synthesized with an automated synthesizer SYMPHONY (RAININ) using a modified Fmoc-protocol. Cycles were modified by using double couplings from the 15$^{th}$ amino acid from the C-terminus of the peptide with five-fold excess of Fmoc-amino acids and coupling reagent. The peptide couplings were performed by TBTU/NMM-activation using a 0.23 mmol substituted NovaSyn TGR-resin or the corresponding preloaded Wang-resin at 25 µmol scale. The cleavage from the resin was carried out by a cleavage-cocktail consisting of 94.5% TFA, 2.5% water, 2.5% EDT and 1% TIS.

Analytical and preparative HPLC were performed by using different gradients on the LiChrograph HPLC system of Merck-Hitachi. The gradients were made up from two solvents: (A) 0.1% TFA in $H_2O$ and (B) 0.1% TFA in acetonitrile. Analytical HPLC were performed under the following conditions: solvents were run (1 ml/min) through a 125-4 Nucleosil RP18-column, over a gradient from 5%-50% B over 15 min and then up to 95% B until 20 min, with UV detection ($\lambda$=220 nm). Purification of the peptides was carried out by preparative HPLC on either a 250-20 Nucleosil 100 RP8-column or a 250-10 LiChrospher 300 RP18-column (flow rate 6 ml/min, 220 nm) under various conditions depending on peptide chain length.

For the identification of the peptides and peptide analogues, laser desorption mass spectrometry was employed using the HP G2025 MALDI-TOF system of Hewlett-Packard.

Example 2

Determination of $IC_{50}$-Values of DP IV-Inhibitors

100 µl inhibitor stock solution were mixed with 100 µl buffer (HEPES pH 7.6) and 50 µl substrate (Gly-Pro-pNA, final concentration 0.4 mM) and preincubated at 30° C. Reaction was started by addition of 20 µl purified porcine DP IV. Formation of the product pNA was measured at 405 nm over 10 min using the HTS 7000Plus plate reader (Perkin Elmer) and slopes were calculated. The final inhibitor concentrations ranged between 1 mM and 30 nM.

For calculation of $IC_{50}$-values GraFit 4.0.13 (Erithacus Software) was used.

Example 3

Determination of $K_i$-Values of DP IV-Inhibitors

For determination of the $K_i$-values DP IV activity was measured in the same way as described in example 2 at final substrate concentrations of 0.05, 0.1, 0.2, and 0.4 mM and further 7 inhibitor concentrations covering the $IC_{50}$ concentration. Calculations were performed using the GraFit Software.

Example 4

Prolyl Endopeptidase (PEP) Enzymatic Activity Assays

The enzymatic activity of PEP was quantified as described recently (Schulz et al., 2002, Modulation of inositol 1,4,5-triphosphate concentration by prolyl endopeptidase inhibition. Eur J Biochem 269: 5813-5820). Cellular extracts as described above were incubated in the assay buffer using the fluorogenic substrate Z-Gly-Pro-NHMec (10 µM; Bachem, Heidelberg, Germany) on a spectrofluorimeter SFM 25 (excitation wavelength 380 nm, emission wavelength 460 nm, Kontron, Neufahrn, Germany) equipped with a four-cell changer and controlled by an IBM-compatible personal computer. The data obtained were analyzed with the software FLUCOL (Machleidt et al., 1995).

Example 5

Assays for Glutaminyl Cyclase Activity

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, HØrsholm, Denmark) in 0.2 M Tris/HCl, pH 8.0 containing 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-βNA from H-Gln-βNA per minute under the described conditions.

In a second fluorometric assay, QC was activity was determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit sofware.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 µl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Example 6

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. Samples (5 µl) were mixed with equal volumes of the matrix solution. For matrix solution we used DHAP/DAHC, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of $Glu^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC was added all 24 hours. In case of Aβ(3-21)a, the assays contained 1% DMSO. At different times, samples were removed from the assay tube, peptides extracted using ZipTips (Millipore) according to the manufacturer's recommendations, mixed with matrix solution (1:1 v/v) and subsequently the mass spectra recorded. Negative controls did either contain no QC or heat deactivated enzyme. For the inhibitor studies the sample composition was the same as described above, with exception of the inhibitory compound added (5 mM benzimidazole or 2 mM 1,10-phenanthroline).

The first QC inhibitors are disclosed in WO 200409859. There are no other potent QC inhibitors known in the art.

The same holds true for combinations and compositions for the treatment of neuronal diseases comprising QC inhibitors. Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugsor be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned above are herein incorporated in their entirety by reference.

The invention embraces all combinations of preferred and more preferred groups and embodiments of groups recited above.

The invention claimed is:

1. A compound of formula 1 including all stereoisomers or pharmaceutically acceptable salts thereof:

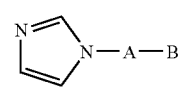

formula 1 wherein:
A is either:
an alkyl chain, an alkenyl chain, an alkynyl chain, or a group selected from formulae (I) to (V):

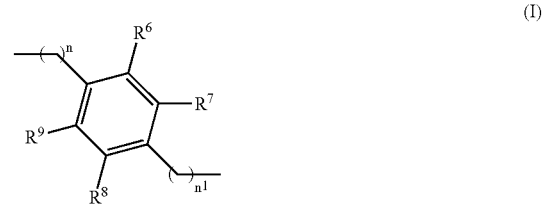

(I)

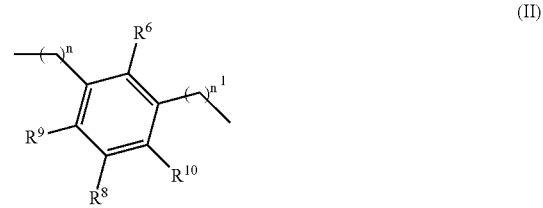

(II)

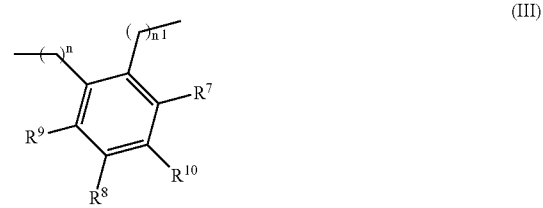

(III)

-continued

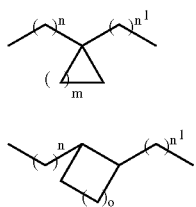
(IV)

(V)

wherein:
$R^6$, $R^7$, $R^8$, $R^9$ and $R^{10}$ are independently H or an alkyl chain, an alkenyl chain, an alkynyl chain, a cycloalkyl, a carbocycle, an aryl, a heteroaryl, or a heterocycle;
n and $n^1$ are independently 1-5;
m is 1-5;
o is 0-4; and
B is a group selected from formulae (VI), (VIa), (VIb) and (VII);

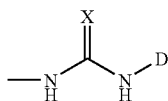
(VI)

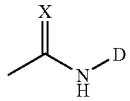
(VIa)

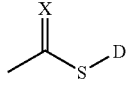
(VIb)

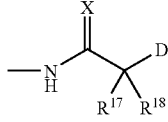
(VII)

wherein:
D represents an alkyl chain, an alkenyl chain, an alkynyl chain, a cycloalkyl, a carbocycle, an aryl, an alkylaryl, a heteroaryl, an alkylheteroaryl, an acyl, or a heterocycle;
wherein if D is an alkyl, the alkyl is selected from the group consisting of ethyl, propyl, n-butyl, tert-butyl, sec-butyl, pentyl, hexyl, heptyl, octyl, or alkoxy;
wherein if D is an aryl, the aryl is selected from the group consisting of phenyl, substituted phenyl; naphthyl, pentalene, pyridin-3-yl, trityl, 4-anilinyl-, 2-biphenylyl-, 3-biphenylyl-, 4-biphenylyl-, indenyl-, 1-anthracenyl-, 2-anthracenyl-, 3-anthracenyl-, and bicyclo[2.2.1]hept-5-en-2-yl;
wherein if D is an aryl, and the aryl is a substituted phenyl, the substituted phenyl is selected from the group consisting of 4-fluoro-phenyl, 3-fluoro-phenyl, pentafluoro-phenyl, 4-hydroxyphenyl-, 4-(methyl)-phenyl, 3-nitro-phenyl-, -2-(methoxy-carbonyl)-phenyl, 2,3,4-(trimethoxy)-phenyl, 2,3-(dimethoxy)-phenyl, 2,4-(dimethoxy)-phenyl, 2,5-(dimethoxy)-phenyl, 3-(cylopentyloxy)-4-(methoxy)-phenyl, 2-(methoxy)-phenyl, 3-(methoxy)-phenyl, 4-(methoxy)-phenyl, 3,4-(dimethoxy)-phenyl, 3,4,5-(trimethoxy)-phenyl, 3,5-(dimethoxy)-phenyl, 4-(pyrazol-1-yl)-phenyl, 4-(acetyl)-phenyl, 4-(benzyloxy)-phenyl, 4-(butoxy)-phenyl, 4-(cyano)-phenyl, 4-(dimethylamino)-phenyl, 4-(ethoxy)-phenyl, 4-(ethyl)-phenyl, 4-(heptyloxy)-phenyl, 4-(iodo)-phenyl, 4-(bromo)-phenyl, 4-(chloro)-phenyl, 4-(isopropyl)-phenyl, 4-(methoxy-carbonyl)-phenyl, 4-(methylsulfanyl)-phenyl, 4-(methylthio)-phenyl, 4-(morpholin-4-yl)-phenyl, 4-(nitro)-phenyl, 4-(oxazol-5-yl)-phenyl, 4-(oxazol-5yl)-phenyl, 4-(piperidine-1-sulfonyl)-phenyl, 4-(piperidinosulfonyl)-phenyl, 4-(pyrazol-1-yl)-phenyl, 4-(trifluoromethoxy)-phenyl, and 4-(trifluoromethyl)-phenyl;
wherein if D is an alkylaryl, the alkylaryl is selected from the group consisting of phenylethyl, 2-phenyleth-1-yl, p-tolyl-methyl-, p-tolyl-ethyl-, m-tolyl-methyl-, m-tolyl-ethyl-, o-tolyl-methyl-, o-tolyl-ethyl-, 2-(4-ethyl-phenyl)-eth-1-yl-, 2,3-dimethyl-phenyl-methyl-, 2,4-dimethyl-phenyl-methyl-, 2,5-dimethyl-phenyl-methyl-, 2,6-dimethyl-phenyl-methyl-, 3,4-dimethyl-phenyl-methyl-, 3,5-dimethyl-phenyl-methyl-, 2,4,6-trimethyl-phenyl-methyl-, 2,3-dimethyl-phenyl-ethyl-, 2,4-dimethyl-phenyl-ethyl-, 2,5-dimethyl-phenyl-ethyl-, 2,6-dimethyl-phenyl-ethyl-, 3,4-dimethyl-phenyl-ethyl-, 3,5-dimethyl-phenyl-ethyl-, 2,4,6-trimethyl-phenyl-ethyl-, diphenyl-methyl, diphenyl-ethyl, triphenyl-methyl, triphenyl-ethyl, α-styryl, β-styryl, cumyl, 2-ethyl-phenyl-methyl-, 3-ethyl-phenyl-methyl-, 4-ethyl-phenyl-methyl-, 2-ethyl-phenyl-ethyl-, 3-ethyl-phenyl-ethyl-, 4-ethyl-phenyl-ethyl-, 2-fluoro-benzyl, 1-methyl-2-fluoro-phen-6-yl-methyl-, 1-methyl-2-fluoro-phen-4-yl-methyl-, 1-methyl-2-fluoro-phen-6-yl-ethyl-, 1-methyl-2-fluoro-phen-4-yl-ethyl-, 1H-indenyl-methyl-, 2H-indenyl-methyl-, 1H-indenyl-ethyl-, 2H-indenyl-ethyl-, indanyl-methyl-, indan-1-on-2-yl-methyl-, indan-1-on-2-yl-ethyl-, tetralinyl-methyl-, tetralinyl-ethyl-, fluorenyl-methyl-, fluorenyl-ethyl-, (3-phenyl)-cyclopent-1-yl, dihydronaphthalinyl-methyl-, dihydronaphthalinyl-ethyl-, or (4-cyclohexyl)-phenyl-methyl- and (4-cyclohexyl)-phenyl-ethyl-;
wherein if D is an alkylheteroaryl, the alkylheteroaryl is selected from the group consisting of pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, tetrahydroisochinolinyl-methyl-, tetrahydroisochinolinyl-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl, 4-methyl-pyridin-3-ethyl, (benzo[d][1,3]dioxol-6yl)-methyl, (furan-2-yl)-methyl, 2-(methoxy-carbonyl)-4-(methyl)-thiophene-3-yl, 3,5-(dimethyl)-isooxazol-4-yl and 5-(methyl)-3-(phenyl)-isooxazol-4-yl;

X represents $CR^{20}R^{21}$, or S;

$R^{20}$ and $R^{21}$ are independently selected from H, alkyl, cycloalkyl, heterocycle, aryl, heteroaryl, -oxyalkyl, -oxyaryl, carbonyl, amido, $NO_2$, $NH_2$, CN, and $CF_3$;

Y is O or S, with the proviso that Y may not be O when the carbocycle formed by $R^{17}$ and $R^{18}$ has 3 members in the ring;

$R^{17}$ and $R^{18}$ are independently selected from H or an alkyl chain, alkenyl chain, a alkynyl chain, a carbocycle, aryl, heteroaryl, heteroalkyl, or can be connected to form a carbocycle with up to 6 ring atoms;

n is 0 or 1;

with the proviso that the following compounds:

(a)
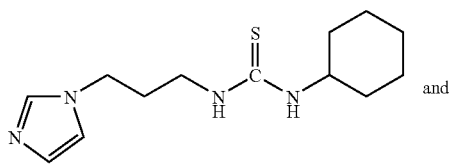 and (b)
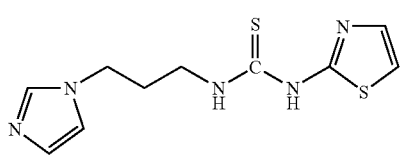

are excluded from formula 1.

2. The compound according to claim 1, wherein A is an unbranched $C_3$ alkyl chain.

3. The compound according to claim 1, wherein A is a group of formula (I), (II) or (III), and n and $n^1$ are each 1.

4. The compound according to any claim 1, wherein B is group (VI).

5. The compound according to claims 1, wherein B is group (VIa).

6. The compound according to claim 1, wherein X represents S.

7. The compound according to claim 1, wherein B is group (VII).

8. The compound according to claim 7, wherein Y represents S.

9. The compound according to claim 7, wherein one of $R^{17}$ and $R^{18}$ is H and the other is Me.

10. The compound according to claim 8, wherein one of $R^{17}$ and $R^{18}$ is H and the other is Me.

11. The compound according to claim 7, wherein one of $R^{17}$ and $R^{18}$ is H and the other is phenyl.

12. The compound according to claim 8, wherein one of $R^{17}$ and $R^{18}$ is H and the other is phenyl.

13. The compound according to claim 7, wherein $R^{17}$ and $R^{18}$ are connected to form a carbocycle with up to 6 ring atoms.

14. The compound according to claim 8, wherein $R^{17}$ and $R^{18}$ are connected to form a carbocycle with up to 6 ring atoms.

15. The compound according to claim 1, wherein D represents a substituted phenyl selected from the group consisting of 4-fluoro-phenyl, 3-fluoro-phenyl, pentafluoro-phenyl, 4-hydroxyphenyl-, 4-(methyl)-phenyl, 3-nitro-phenyl-, 4-(trifluoromethyl)-phenyl, -2-(methoxy-carbonyl)-phenyl, 2,3,4-(trimethoxy)-phenyl, 2,3-(dimethoxy)-phenyl, 2,4-(dimethoxy)-phenyl, 2,5-(dimethoxy)-phenyl, 3-(cylo-pentyloxy)-4-(methoxy)-phenyl, 2-(methoxy)-phenyl, 3-(methoxy)-phenyl, 4-(methoxy)-phenyl, 3,4-(dimethoxy)-phenyl, 3,4,5-(trimethoxy)-phenyl, 3,5-(dimethoxy)-phenyl, 4-(pyrazol-1-yl)-phenyl, 4-(acetyl)-phenyl, 4-(benzyloxy)-phenyl, 4-(butoxy)-phenyl, 4-(cyano)-phenyl, 4-(dimethylamino)-phenyl, 4-(ethoxy)-phenyl, 4-(ethyl)-phenyl, 4-(heptyloxy)-phenyl, 4-(iodo)-phenyl, 4-(bromo)-phenyl, 4-(chloro)-phenyl, 4-(isopropyl)-phenyl, 4-(methoxy-carbonyl)-phenyl, 4-(methylsulfanyl)-phenyl, 4-(methylthio)-phenyl, 4-(morpholin-4-yl)-phenyl, 4-(nitro)-phenyl, 4-(oxazol-5-yl)-phenyl, 4-(oxazol-5yl)-phenyl, 4-(piperidine-1-sulfonyl)-phenyl, 4-(piperidinosulfonyl)-phenyl, 4-(pyrazol-1-yl)-phenyl, 4-(trifluoromethoxy)-phenyl and 4-(trifluoromethyl)-phenyl.

16. The compound according to claim 1, wherein D represents 3,4-dimethoxyphenyl.

17. The compound according to claim 1 corresponding to either formula 1a:

(1a)
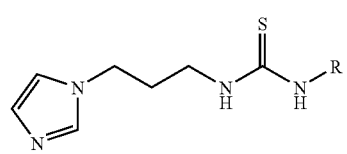

wherein R is selected from:

| R |
|---|
| tert-Butyl |
| Benzyl |
| Phenyl |
| 4-(fluoro)-phenyl |
| 4-(ethyl)-phenyl |
| 4-(trifluoromethyl)-phenyl |
| 4-(acetyl)-phenyl |
| 4-(methoxy)-phenyl |
| bicyclo[2.2.1]hept-5-en-2-yl |
| 3,4-(dimethoxy)-phenyl |
| 2,4-(dimethoxy)-phenyl |
| 3,5-(dimethoxy)-phenyl |
| 2-(methoxy-carbonyl)-phenyl |
| 4-(oxazol-5-yl)-phenyl |
| 4-(pyrazol-1-yl)-phenyl |
| 4-(isopropyl)-phenyl |
| 4-(piperidine-1-sulfonyl)-phenyl |
| 4-(morpholin-4-yl)-phenyl |
| 4-(cyano)-phenyl |
| 2,3-dihydro-benzo[1,4]dioxin-6-yl |
| benzo[1,3]dioxol-5-yl |
| 3,4,5(trimethoxy)-phenyl |
| 3-(methoxy)-phenyl |
| 4-(ethoxy)-phenyl |
| 4-(benzyloxy)-phenyl |
| 4-(iodo)-phenyl |
| 4-(bromo)-phenyl |
| 4-(methyl)-phenyl |
| Naphthalen-1-yl |
| 4-(nitro)-phenyl |
| Butyl |
| Cyclooctyl |
| Furan-2-ylmethyl |
| Tetrahydrofuran-2-ylmethyl |
| Benzo[1,3]dioxol-5-ylmethyl |
| 2-(morpholin-4-yl)-ethyl |
| 4-(methylsulfanyl)-phenyl |

-continued

| R |
|---|
| 4-(dimethylamino)-phenyl |
| 4-(trifluoromethoxy)-phenyl |
| Benzoyl |
| Pyridin-4-yl | or formula 1g:

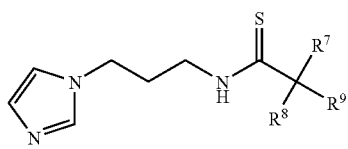
(1g)

wherein R⁷ R⁸ and R⁹ are:

| R⁷ | R⁸ | R⁹ |
|---|---|---|
| 3,4-(dimethoxy)-phenyl | H | H | or formula 1i:

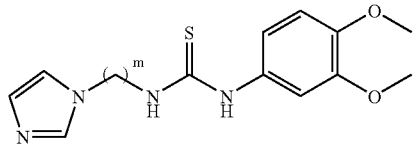
(1i)

wherein m is 2;

or a pharmaceutically acceptable salt or stereoisomer thereof.

18. The compound according to claim 1 corresponding to either formula 1a

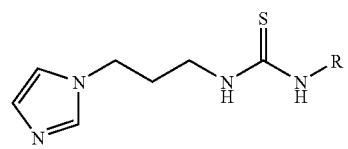
(1a)

wherein R is selected from:

| 4-(methoxy)-benzyl |
| 3,4-(dimethoxy)-benzyl |
| Benzo[c][1,2,5]thiadiazol-4-yl |
| Benzo[c][1,2,5]thiadiazol-5-yl |
| 5-(methyl)-3-(phenyl)-isooxazol-4-yl |
| 3,5-(dimethyl)-isooxazol-4-yl | or formula 1e:

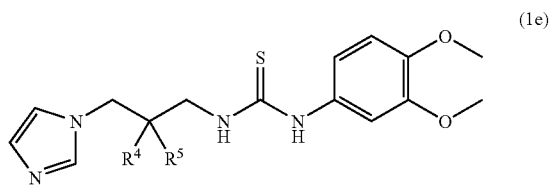
(1e)

wherein R⁴ and R⁵ are selected from:

| R⁴ | R⁵ |
|---|---|
| H | Methyl |
| Methyl | H |
| Methyl | Methyl |
| —CH₂—CH₂— | | or formula 1f:

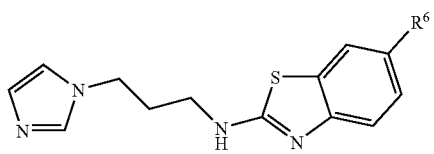
(1f)

wherein R⁶ is:

| H |
| Chloro |
| Methoxy | or formula 1g:

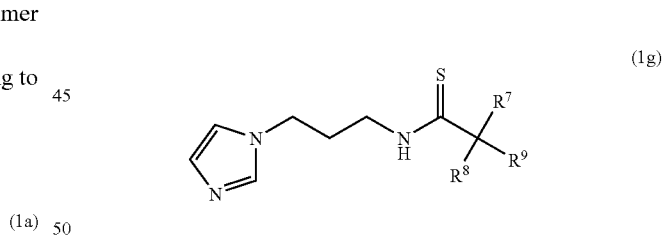
(1g)

wherein R⁷, R⁸ and R⁹ are selected from:

| R⁷ | R⁸ | R⁹ |
|---|---|---|
| Phenyl | H | H |
| Phenyl | Methyl | H |
| Phenyl | H | Methyl |
| Phenyl | H | Ethyl |
| Phenyl | H | Phenyl |
| 3,4-(dimethoxy)-phenyl | Methyl | Methyl |
| 4-(methoxy)-phenyl | —CH₂—C₃H₆—CH₂— | |
| 4-(methoxy)-phenyl | —CH₂—CH₂— | |
| 3,4-(dimethoxy)-phenyl | —CH₂—CH₂— | |
| 3,4,5-(trimethoxy)-phenyl | —CH₂—CH₂— | |

-continued

| R⁷ | R⁸ | R⁹ |
|---|---|---|
| 2,3,4-(trimethoxy)-phenyl | —CH₂—CH₂— | |
| 2,3-(dimethoxy)-phenyl | —CH₂—CH₂— | |
| 2,5-(dimethoxy)-phenyl | —CH₂—CH₂— | | or formula 1h:

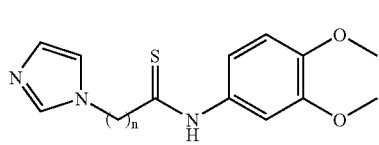

(1h)

wherein n is 4;

or a pharmaceutically acceptable salt or stereoisomer thereof.

19. The compound according to claim 1 corresponding to either formula 1a:

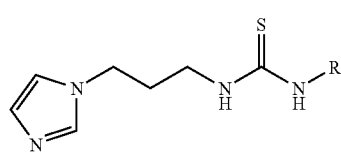

(1a)

wherein R is 4-(methoxy-carbonyl)-phenyl;

formula 1g:

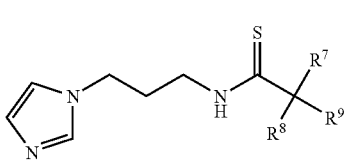

(1g)

wherein R⁷, R⁸ and R⁹ are selected from:

| R⁷ | R⁸ | R⁹ |
|---|---|---|
| 4-(chloro)-phenyl | —CH₂—CH₂—CH₂— | |
| 4-(chloro)-phenyl | —CH₂—C₂H₄—CH₂— | | or formula 1i:

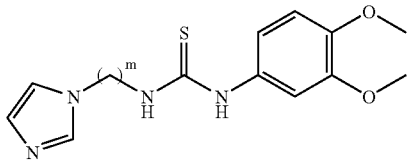

(1i)

wherein m is 4;

or a pharmaceutically acceptable salt or stereoisomer thereof.

20. The compound according to claim 1 corresponding to either formula 1a:

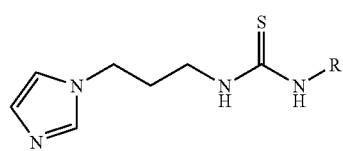

(1a)

wherein R is:

| R |
|---|
| 2-(methoxy-carbonyl)-thiophene-3-yl |
| 3-(ethoxy-carbonyl)-4,5,6,7-tetrahydrobenzo[b]thio-phene2-yl |
| 2-(methoxy-carbonyl)-4-(methyl)-thiophene-3-yl | or formula 1g:

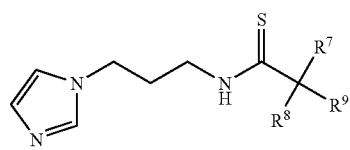

(1g)

wherein R⁷, R⁸ and R⁹ are selected from:

| R⁷ | R⁸ | R⁹ |
|---|---|---|
| Thiophen-2-yl | H | H |
| 2-(methoxy)-phenyl | —CH₂—CH₂— | |
| 3-(methoxy)-phenyl | —CH₂—CH₂— | |
| 3,5-(dimethoxy)-phenyl | —CH₂—CH₂— | | or formula 1h:

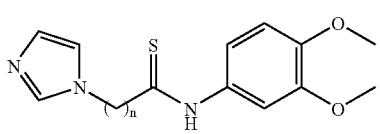

(1h)

wherein n is 3 or 5;

or a pharmaceutically acceptable salt or stereoisomer thereof.

21. The compound according to claim 1 corresponding to formula 1a,

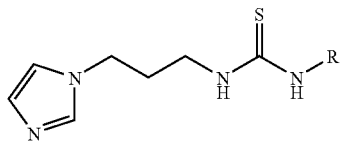

(1a)

wherein R is 3,4-(dimethoxy)-phenyl;
or a pharmaceutically acceptable salt or stereoisomer thereof.

22. The compound according to claim 1 corresponding to formula 1g,

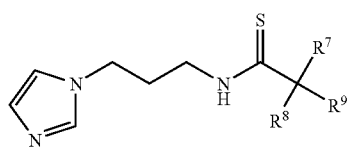

(1g)

wherein $R^7$ $R^8$ and $R^9$ are:

| $R^7$ | $R^8$ | $R^9$ |
|---|---|---|
| 3,4-(dimethoxy)-phenyl | H | H | or a pharmaceutically acceptable salt or stereoisomer thereof.

23. The compound according to claim 1 corresponding to formula 1g,

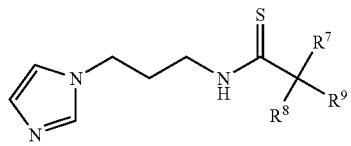

(1g)

wherein $R^7$ $R^8$ and $R^9$ are:

| $R^7$ | $R^8$ | $R^9$ |
|---|---|---|
| 3,4-(dimethoxy)-phenyl | —CH$_2$—CH$_2$— | | or a pharmaceutically acceptable salt or stereoisomer thereof.

24. A pharmaceutical composition comprising at least one compound according to claim 1 optionally in combination with a therapeutically acceptable carrier and/or excipient.

25. The pharmaceutical composition according to claim 24 for parenteral, enteral or oral administration.

26. A pharmaceutical composition comprising:
(i) at least one compound of formula 1 including all stereoisomers or pharmaceutically acceptable salts thereof:

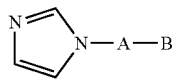

formula 1 wherein:
A is either:
an alkyl chain, an alkenyl chain, an alkynyl chain or is a group selected from formulae (I) to (V):

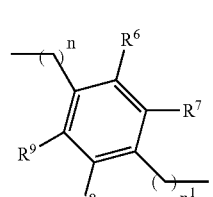

(I)

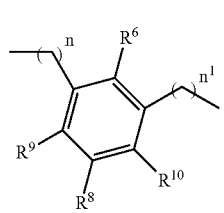

(II)

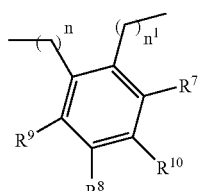

(III)

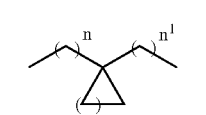

(IV)

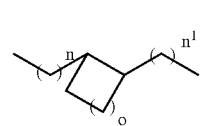

(V)

wherein:
$R^6$, $R^7$, $R^8$, $R^9$ and $R^{10}$ are independently H or an alkyl chain, an alkenyl chain, an alkynyl chain, a cycloalkyl, a carbocycle, an aryl, a heteroaryl, or a heterocycle;
n and $n^1$ are independently 1-5;
m is 1-5;
o is 0-4; and
B is a group selected from formulae (VI), (VIa), (VIb), and (VII):

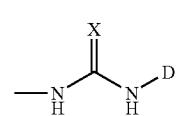

(VI)

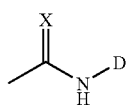 (VIa)

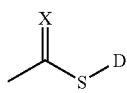 (VIb)

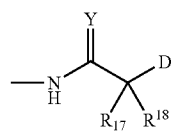 (VII)

wherein:

D represents an alkyl chain, alkenyl chain, alkynyl chain, a cycloalkyl, carbocycle, aryl, -alkylaryl, heteroaryl, -alkylheteroaryl, acyl, a heterocycle;

X represents $CR^{20}R^{21}$, O, S, or $NR^{19}$;

$R^{20}$ and $R^{21}$ are independently selected from H, alkyl, cycloalkyl, heterocycle, aryl, heteroaryl, -oxyalkyl, -oxyaryl, carbonyl, amido, $NO_2$, $NH_2$, CN, $CF_3$;

Y is O or S;

$R^{17}$ and $R^{18}$ are independently selected from H or an alkyl chain, alkenyl chain, an alkynyl chain, a carbocycle, aryl, heteroaryl, heteroalkyl, or can be connected to form a carbocycle with up to 6 ring atoms; and n is 0 or 1; and (ii) at least one compound selected from the group consisting of PEP-inhibitors, LiCl, inhibitors of dipeptidyl aminopeptidases, preferably inhibitors of DP IV or DP IV-like enzymes, NPY-receptor ligands, NPY agonists, ACE inhibitors, PIMT enhancers, inhibitors of beta secretases, inhibitors of gamma secretases, inhibitors of neutral endopeptidase, PDE-4 inhibitors, MAO inhibitors, TNFalpha inhibitors, amyloid protein or amyloid peptide deposition inhibitors, sigma-1 receptor inhibitors and histamine H3 antagonists;

optionally in combination with a therapeutically acceptable carrier and/or excipient.

27. The pharmaceutical composition according to claim 26, wherein said inhibitor of DP V/DP IV-like enzymes is selected from the group consisting of L-threo-isoleucyl pyrrolidide, L-allo-isoleucyl thiazolidide, L-allo-isoleucyl pyrrolidide and salts thereof, valine pyrrolidide, BMS-477118, CP-867534-01, LAF-237, PHX-1004, SSR-162369, SYR-322, TSL-225, FE-999011 GW-229A, 815541, K-579, MK-431, PT-100 and one of

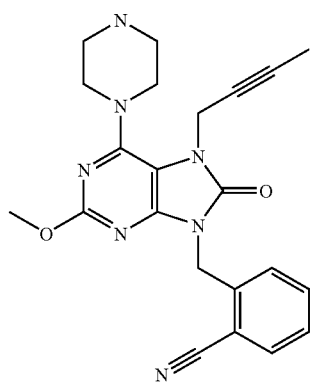

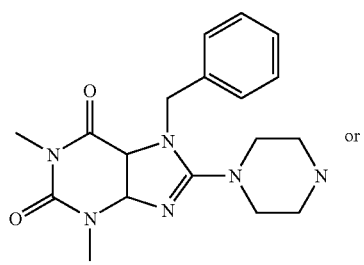 or

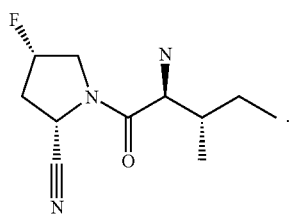

28. The pharmaceutical composition according to claim 26, wherein said NPY antagonist is selected from 3a,4,5,9b-tetrahydro-1h-benz[e]indol-2-yl amine, BIBP3226 and (R)-N2-(diphenylacetyl)-(R)-N-[1-(4-hydroxy-phenyl) ethyl]arginine amide.

29. The pharmaceutical composition according to claim 26, wherein said PEP-inhibitor is selected from the group consisting of chemical derivatives of proline or small peptides containing terminal prolines, benzyloxycarbonyl-prolyl-prolinal, N-terminal substituted L-proline, L-prolylpyrrolidine, substituted N-benzyloxycarbonyl (Z) dipeptides containing prolinal at the carboxy terminus, substituted thioprolines, substituted thiazolidines, substituted oxopyrrolidines, carboxy terminal modified prolines including fluorinated ketone derivatives, chloromethyl ketone derivatives of acyl-proline or acylpeptide-proline (Z-Gly-Pro-$CH_2$Cl) and 2-acylpyrrolidine derivatives.

30. The pharmaceutical composition according to claim 26, wherein said PEP-inhibitor is selected from the group consisting of Fmoc-Ala-Pyrr-CN, Z-321, ONO-1603, JTP-4819 and S17092.

31. The pharmaceutical composition according to claim 26, wherein said PEP-inhibitor is

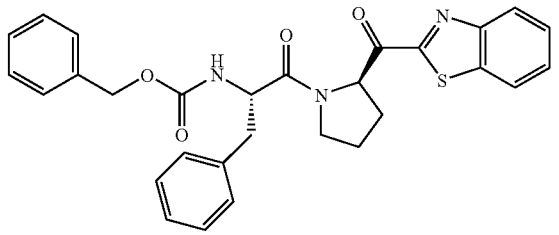

32. The pharmaceutical composition according to claim 26, wherein said ACE-inhibitor is SDZ ENA 713 (rivastigmine (+)-(S)-N-ethyl-3-[(1-dimethylamino)ethyl]-N-methyl phenylcarbamate hydrogen tartrate.

33. The pharmaceutical composition according to claim 26, wherein said PDE-4 inhibitor is selected from the group consisting of Rolipram, CC-002, L-826141, Sch-351591 (D-4396), OS-0217, IBFB-130011, IBFB-150007, IBFB-130020, IBFB-140301, IC-485, VMX-554, VMX-565, MEM-1414, MEM-1018, MEM-1091, MEM-1145, CI-1044, BHN, ZK-117137 and SB-207499 or analogs thereof.

34. The pharmaceutical composition according to claim 26, wherein said PIMT enhancer is a 10-aminoaliphatyl-dibenz[b,f]oxepine of the general formula

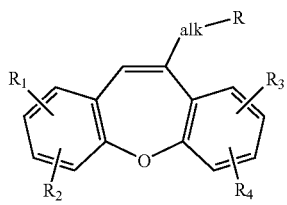

wherein alk is a divalent aliphatic radical, R is an amino group that is unsubstituted or mono- or di-substituted by monovalent aliphatic and/or araliphatic radicals or disubstituted by divalent aliphatic radicals, and R₁, R₂, R₃ and R₄ are each, independently of the others, hydrogen, lower alkyl, lower alkoxy, halogen or trifluoromethyl.

35. The pharmaceutical composition according to claim 26, wherein said gamma secretase inhibitor is

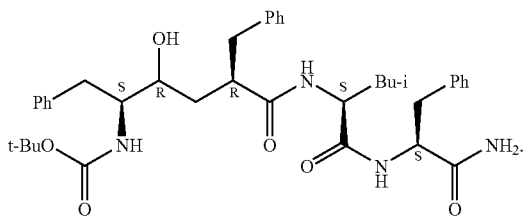

36. The pharmaceutical composition according to claim 26, wherein said beta secretase inhibitor is

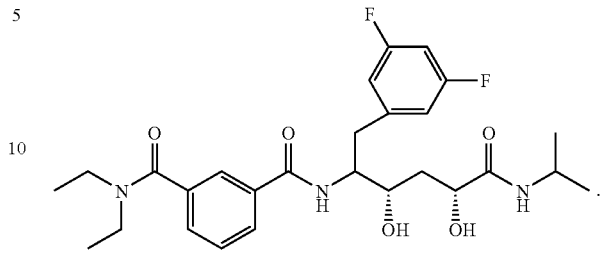

37. The pharmaceutical composition according to claim 26, wherein said MAO inhibitor is ladostigil of the formula

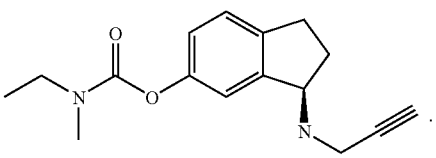

38. The pharmaceutical composition according to claim 26, wherein said histamine H3 antagonist is a compound selected from the group consisting of A-331440, A-349821, 3874-H1, UCL-2173, UCL-1470, DWP-302, GSK-189254A, GSK-207040A, cipralisant, GT-2203, 1S,2S)-2-(2-Aminoethyl)-1-(1H-imidazol-4-yl)cyclopropane, JNJ-5207852, NNC-0038-0000-1049, dual H1/H3, Sch-79687 and one of

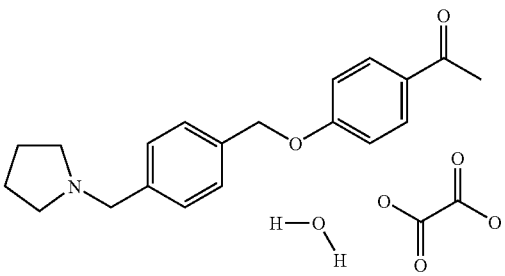

or

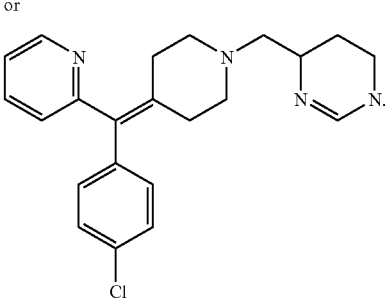

* * * * *